(12) United States Patent
Burgeson et al.

(10) Patent No.: US 6,682,911 B1
(45) Date of Patent: Jan. 27, 2004

(54) LAMININS AND USES THEREOF

(75) Inventors: Robert E. Burgeson, Marblehead, MA (US); Marie-France Champliaud, Sumerville, MA (US); Pamela Olson, Brookline, MA (US); Manuel Koch, Cambridge, MA (US); William Brunken, Canton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/561,709

(22) Filed: May 1, 2000

Related U.S. Application Data

(63) Continuation-in-part of application No. 09/168,949, filed on Oct. 9, 1998, now abandoned.
(60) Provisional application No. 60/061,609, filed on Oct. 10, 1997.

(51) Int. Cl.$^7$ .......................... C12P 21/02; C12P 21/04; A61K 38/17; C07H 21/04
(52) U.S. Cl. ...................... 435/69.8; 435/70.1; 530/353; 536/23.5
(58) Field of Search ................................. 530/350, 353; 536/23.1, 23.5; 435/69.8, 70.1

(56) References Cited

U.S. PATENT DOCUMENTS 5,660,982 A    8/1997   Tryggvason et al.

FOREIGN PATENT DOCUMENTS

WO    WO 99 19348    * 4/1999

OTHER PUBLICATIONS

Aumailley et al, Laminins: A Family of Diverse Multifunctional Molecules of Basement Membranes. The Journal of Investigative Dermatology. Feb. 1996, vol. 106, pp. 209–214.

Engvall, "Laminin Variants: Why, Where and When? Kidney International". Sep. 1993, vol. 43, pp. 2–6.

Olsen et al, Cloning and characterization of the human laminin beta–4 chain. Laminin beta–4 chain precursor. Genbank PID g4003505. Publicly available on Dec. 2, 1997.

Togel et al. J. Bio. Chem. 269(17):12993–8 (1994).

Ngo et al., in The Protein Folding Problem and Tertiary Structure Prediction,1994, Merz et al., (ed.), Birkhauser, Boston, MA, p. 433 and 492–495.*

Skolnick et al. in Trends in Biotechnology, 2000, 18(1):34–39,.*

* cited by examiner

Primary Examiner—Christina Chan
Assistant Examiner—Maher Haddad
(74) Attorney, Agent, or Firm—Fish & Richardson P.C.

(57) ABSTRACT

The present invention is based on the discovery of a novel member of the laminin family, laminin 12. Accordingly, the present invention features a purified or isolated preparation or a recombinant preparation of laminin 12 which includes an α2 subunit, β1 subunit and a γ3 subunit.

9 Claims, 21 Drawing Sheets cDNA sequence encoding laminin α2 subunit

```
   1 cagcgactcc tctggctccc gagaagtgga tccggtcgcg gccactacga tgccgggagc
  61 cgccggggtc ctcctccttc tgctgctctc cggaggcctc gggggcgtac aggcgcagcg
 121 gccgcagcag cagcggcagt cacaggcaca tcagcaaaga ggtttattcc ctgctgtcct
 181 gaatcttgct tctaatgctc ttatcacgac caatgcaaca tgtggagaaa aaggacctga
 241 aatgtactgc aaattggtag aacatgtccc tgggcagcct gtgaggaacc cgcagtgtcg
 301 aatctgcaat caaaacagca gcaatccaaa ccagagacac ccgattacaa atgctattga
 361 tggaaagaac acttggtggc agagtcccag tattaagaat ggaatcgaat accattatgt
 421 gacaattaca ctggatttac agcaggtgtt ccagatcgcg tatgtgattg tgaaggcagc
 481 taactccccc cggcctggaa actggatttt ggaacgctct cttgatgatg ttgaatacaa
 541 gccctggcag tatcatgctg tgacagacac ggagtgccta acgctttaca atatttatcc
 601 ccgcactggg ccaccgtcat atgccaaaga tgatgaggtc atctgcactt cattttactc
 661 caagatacac ccattagaaa atggagagat tcacatctct ttaatcaatg ggagaccaag
 721 tgccgatgat ccttctccag aactgctaga atttacctcc gctcgctata ttcgcctgag
 781 atttcagagg atccgcacac tgaatgctga cttgatgatg tttgctcaca aagacccaag
 841 agaaattgac cccattgtca ccagaagata ttactactcg gtcaaggata tttcagttgg
 901 agggatgtgc atctgctatg gtcatgccag ggcttgtcca cttgatccag cgacaaataa
 961 atctcgctgt gagtgtgagc ataacacatg tggcgatagc tgtgatcagt gctgtccagg
1021 attccatcag aaaccctgga gagctggaac ttttctaact aaaactgaat gtgaagcatg
1081 caattgtcat ggaaaagctg aagaatgcta ttatgatgaa aatgttgcca aagaaatct
1141 gagtttgaat atacgtggaa agtacattgg aggggtgtc tgcattaatt gtacccaaaa
1201 cactgctggt ataaactgcg agacatgtac agatggcttc tcagaccca aagggggtatc
1261 tccaaattat ccaaggccat gccagccatg tcattgcgat ccaattggtt ccttaaatga
1321 agtctgtgtc aaggatgaga acatgctcg acgaggtttg gcacctggat cctgtcattg
1381 caaaactggt tttggaggtg tgagctgtga tcggtgtgcc aggggctaca ctggctaccc
1441 ggactgcaaa gcctgtaact gcagtgggtt agggagcaaa aatgaggatc cttgttttgg
1501 cccctgtatc tgcaaggaaa atgttgaagg aggagactgt agtcgttgca aatccggctt
1561 cttcaatttg caagaggata attggaaagg ctgcgatgag tgtttctgtt cagggggtttc
1621 aaacagatgt cagagttcct actggaccta tggcaaaata caagatatga gtggctggta
1681 tctgactgac cttcctggcc gcattcgagt ggctccccag caggacgact tggactcacc
1741 tcagcagatc agcatcagta acgcggaggc ccggcaagcc ctgccgcaca gctactactg
1801 gagcgcgccg gctccctatc tgggaaacaa actcccagca gtaggaggac agttgacatt
1861 taccatatca tatgaccttg aagaagagga agaagataca gaacgtgttc tccagcttat
1921 gattatctta gagggtaatg acttgagcat cagcacagcc caagatgagg tgtacctgca
1981 cccatctgaa gaacatacta atgtattgtt acttaaagaa gaatcattta ccatacatgg
2041 cacacatttt ccagtccgta gaaaggaatt tatgacagtg cttgcgaatt tgaagagagt
2101 cctcctacaa atcacataca gctttgggat ggatgccatc ttcaggttga gctctgttaa
2161 ccttgaatcc gctgtctcct atcctactga tggaagcatt gcagcagctg tagaagtgtg
2221 tcagtgccca ccagggtata ctggctcctc ttgtgaatct tgttggccta ggcacaggcg
2281 agttaacggc actattttg gtggcatctg tgagccatgt cagtgctttg gtcatgcgga
2341 gtcctgtgat gacgtcactg gagaatgcct gaactgtaag gatcacacag gtggcccata
2401 ttgtgataaa tgtcttcctg gtttctatgg cgagcctact aaaggaacct ctgaagactg
2461 tcaaccctgt gcctgtccac tcaatatccc atccaataac tttagcccaa cgtgccattt
2521 agaccggagt cttggattga tctgtgatgg atgccctgtc gggtacacag gaccacgctg
2581 tgagaggtgt gcagaaggct attttggaca accctctgta cctggaggat catgtcagcc
2641 atgccaatgc aatgacaacc ttgacttctc catccctggc agctgtgaca gcttgtctgg
2701 ctcctgtctg atatgtaaac aggtacaaac aggccggtac tgtgagctct gtgctgatgg
```

FIG. 1A

```
2761 atattttgga gatgcagttg atgcgaagaa ctgtcagccc tgtcgctgta atgccggtgg
2821 ctctttctct gaggtttgcc acagtcaaac tggacagtgt gagtgcagag ccaacgttca
2881 gggtcagaga tgtgacaaat gcaaggctgg gaccttttggc ctacaatcag caagggggctg
2941 tgttccctgc aactgcaatt cttttgggtc taagtcattc gactgtgaag agagtggaca
3001 atgttggtgc caacctggag tcacagggaa gaaatgtgac cgctgtgccc acggctattt
3061 caacttccaa gaaggaggct gcacagcttg tgaatgttct catctgggta ataattgtga
3121 cccaaagact gggcgatgca tttgcccacc caataccatt ggagagaaat gttctaaatg
3181 tgcacccaat acctggggcc acagcattac cactggttgt aaggcttgta actgcagcac
3241 agtgggatcc ttggatttcc aatgcaatgt aaatacaggc caatgcaact gtcatccaaa
3301 attctctggt gcaaaatgta cagagtgcag tcgaggtcac tggaactacc ctcgctgcaa
3361 tctctgtgac tgcttcctcc ctgggacaga tgccacaacc tgtgattcag agactaaaaa
3421 atgctcctgt agtgatcaaa ctgggcagtg cacttgtaag gtgaatgtgg aaggcatcca
3481 ctgtgacaga tgccggcctg gcaaattcgg actcgatgcc aagaatccac ttggctgcag
3541 cagctgctat tgcttcggca ctactaccca gtgctctgaa gcaaaaggac tgatccggac
3601 gtgggtgact ctgaaggctg agcagaccat tctacccctg gtagatgagg ctctgcagca
3661 cacgaccacc aagggcattg ttttcaaca tccagagatt gttgcccaca tggacctgat
3721 gagagaagat ctccatttgg aaccttttta ttggaaactt ccagaacaat ttgaaggaaa
3781 gaagttgatg gcctatgggg gcaaactcaa gtatgcaatc tatttcgagg ctcgggaaaga
3841 aacaggtttc tctacatata atcctcaagt gatcattcga ggtgggacac ctactcatgc
3901 tagaattatc gtcaggcata tggctgctcc tctgattggc caattgacaa ggcatgaaat
3961 tgaaatgaca gagaaagaat ggaaatatta tggggatgat cctcgagtcc atagaactgt
4021 gacccgagaa gacttcttgg atatactata tgatattcat tacattctta tcaaagctac
4081 ttatggaaat ttcatgcgac aaagcaggat ttctgaaatc tcaatggagg tagctgaaca
4141 aggacgtgga acaacaatga ctcctccagc tgacttgatt gaaaaatgtg attgtcccct
4201 gggctattct ggcctgtcct gtgaggcatg cttgccggga ttttatcgac tgcgttctca
4261 accaggtggc cgcacccctg gaccaaccct gggcacctgt gttccatgtc aatgtaatgg
4321 acacagcagc ctgtgtgacc ctgaaacatc gatatgccag aattgtcaac atcacactgc
4381 tggtgacttc tgtgaacgat gtgctcttgg atactatgga attgtcaagg gattgccaaa
4441 tgactgtcag caatgtgcct gccctctgat ttcttccagt aacaatttca gcccctcttg
4501 tgtcgcagaa ggacttgacg actaccgctg cacggcttgt ccacggggat atgaaggcca
4561 gtactgtgaa aggtgtgccc ctggctatac tggcagtcca ggcaaccctg gaggctcctg
4621 ccaagaatgt gagtgtgatc cctatggctc actgcctgtg cctgtgacc ctgtcacagg
4681 attctgcacg tgccgacctg gagccacggg aaggaagtgt gacggctgca agcactggca
4741 tgcacgcgag ggctgggagt gtgttttttg tggagatgag tgcactggcc ttcttctcgg
4801 tgacttggct cgcctggagc agatggtcat gagcatcaac ctcactggtc cgctgcctgc
4861 gccatataaa atgctgtatg gtcttgaaaa tatgactcag gagctaaagc acttgctgtc
4921 acctcagcgg gccccagaga ggcttattca gctggcagag ggcaatctga atacactcgt
4981 gaccgaaatg aacgagctgc tgaccagggc taccaaagtg acagcagatg gcgagcagac
5041 cggacaggat gctgagagga ccaacacaag agcaaagtcc ctgggagaat tcattaagga
5101 gcttgcccgg gatgcagaag ctgtaaatga aaaagctata aaactaaatg aaactctagg
5161 aactcgagac gaggcctttg agagaaattt ggaagggctt cagaaagaga ttgaccagat
5221 gattaaagaa ctgaggagga aaaatctaga gacacaaaag gaaattgctg aagatgagtt
5281 ggtagctgca gaagcccttc tgaaaaaagt gaagaagctg tttggagagt cccggggggga
5341 aaatgaagaa atggagaagg atctccggga aaactggct gactacaaaa acaaagttga
5401 tgatgcttgg gacctttga gagaagccac agataaaaatc agagaagcta atcgcctatt
5461 tgcagtaaat cagaaaaaca tgactgcatt ggagaaaaag aaggaggctg ttgagagcgg
5521 caaacgacaa attgagaaca cttttaaaga aggcaatgac atactcgatg aagccaaccg
5581 tcttgcagat gaaatcaact ccatcataga ctatgttgaa gacatccaaa ctaaattgcc
```

FIG. 1B

```
5641 acctatgtct gaggagctta atgataaaat agatgacctc tcccaagaaa taaaggacag
5701 gaagcttgct gagaaggtgt cccaggctga gagccacgca gctcagttga atgactcatc
5761 tgctgtcctt gatggaatcc ttgatgaggc taaaaacatc tccttcaatg ccactgcagc
5821 cttcaaagct tacagcaata ttaaggacta tattgatgaa gctgagaaag ttgccaaaga
5881 agccaaagat cttgcacatg aagctacaaa actggcaaca ggtcctcggg gtttattaaa
5941 ggaagatgcc aaaggctgtc ttcagaaaag cttcaggatt cttaacgaag ccaagaagtt
6001 agcaaatgat gtaaaagaaa atgaagacca tctaaatggc ttaaaaacca ggatagaaaa
6061 tgctgatgct agaaatgggg atctcttgag aactttgaat gacactttgg gaaagttatc
6121 agctattcca aatgatacag ctgctaaact gcaagctgtt aaggacaaag ccagacaagc
6181 caacgacaca gctaaagatg tactggcaca gattacagag ctccaccaga acctcgatgg
6241 cctgaagaag aattacaata aactagcaga cagcgtcgcc aaaacgaatg ctgtggttaa
6301 agatccttcc aagaacaaaa tcattgccga tgcagatgcc actgtcaaaa atttagaaca
6361 ggaagctgac cggctaatag ataaactcaa acccatcaag gaacttgagg ataacctaaa
6421 gaaaaacatc tctgagataa aggaattgat aaaccaagct cggaaacaag ccaattctat
6481 caaagtatct gtgtcttcag gaggtgactg cattcgaaca tacaaaccag aaatcaagaa
6541 aggaagttac aataatattg ttgtcaacgt aaagacagct gttgctgata acctcctctt
6601 ttatcttgga agtgccaaat ttattgactt tctggctata gaaatgcgta aaggcaaagt
6661 cagcttcctc tgggatgttg atctggagt tggacgtgta gagtacccag atttgactat
6721 tgatgactca tattggtacc gtatcgtagc atcaagaact gggagaaatg gaactatttc
6781 tgtgagagcc ctggatggac ccaaagccag cattgtgccc agcacacacc attcgacgtc
6841 tcctccaggg tacacgattc tagatgtgga tgcaaatgca atgctgtttg ttggtggcct
6901 gactgggaaa ttaaagaagg ctgatgctgt acgtgtgatt acattcactg gctgcatggg
6961 agaaacatac tttgacaaca aacctatagg tttgtggaat ttccgagaaa agaaggtga
7021 ctgcaaagga tgcactgtca gtcctcaggt ggaagatagt gaggggacta ttcaatttga
7081 tggagaaggt tatgcattgg tcagccgtcc cattcgctgg taccccaaca tctccactgt
7141 catgttcaag ttcagaacat tttcttcgag tgctcttctg atgtatcttg ccacacgaga
7201 cctgagagat ttcatgagtg tggagctcac tgatgggcac ataaaagtca gttacgatct
7261 gggctcagga atggcttccg ttgtcagcaa tcaaaaccat aatgatggga aatggaaatc
7321 attcactctg tcaagaattc aaaaacaagc caatatatca attgtagata tagatactaa
7381 tcaggaggag aaatatagcaa cttcgtcttc tggaaacaac tttggtcttg acttgaaagc
7441 agatgacaaa atatattttg gtggcctgcc aacgctgaga aacttgagta tgaaagcaag
7501 gccagaagta aatctgaaga aatattccgg ctgcctcaaa gatattgaaa tttcaagaac
7561 tccgtacaat atactcagta gtcccgatta tgttggtgtt accaaaggat gttccctgga
7621 gaatgtttac acagttagct ttcctaagcc tggttttgtg gagctctccc ctgtgccaat
7681 tgatgtagga acagaaatca acctgtcatt cagcaccaag aatgagtccg gcatcattct
7741 ttttgggaagt ggagggacac cagcaccacc taggagaaaa cgaaggcaga ctggacaggc
7801 ctattatgta atactcctca acaggggccg tctggaagtg catctctcca caggggcacg
7861 aacaatgagg aaaattgtca tcagaccaga gccgaatctg tttcatgatg gaagagaaca
7921 ttccgttcat gtagagcgaa ctagaggcat cttacagtt caagtggatg aaaacagaag
7981 atacatgcaa aacctgacag ttgaacagcc tatcgaagtt aaaaagcttt tcgttggggg
8041 tgctccacct gaatttcaac cttccccact cagaaatatt cctccttttg aaggctgcat
8101 atggaatctt gttattaact ctgtccccat ggactttgca aggcctgtgt ccttcaaaaa
8161 tgctgacatt ggtcgctgtg cccatcagaa actccgtgaa gatgaagatg gagcagctcc
8221 agctgaaata gttatccagc ctgagccagt tcccacccca gcctttccta cgcccacccc
8281 agttctgaca catggtcctt gtgctgcaga atcagaacca gctctttga tagggagcaa
8341 gcagttcggg ctttcaagaa acagtcacat tgcaattgca tttgatgaca ccaaagttaa
8401 aaaccgtctc acaattgagt tggaagtaag aaccgaagct gaatccggct tgcttttta
8461 catggctgcg atcaatcatg ctgattttgc aacagttcag ctgagaaatg gattgcccta
```

FIG. 1C 8521 cttcagctat gacttgggga gtggggacac ccacaccatg atccccacca aaatcaatga
8581 tggccagtgg cacaagatta agataatgag aagtaagcaa gaaggaattc tttatgtaga
8641 tggggcttcc aacagaacca tcagtcccaa aaaagccgac atcctggatg tcgtgggaat
8701 gctgtatgtt ggtgggttac ccatcaacta cactacccga agaattggtc cagtgaccta
8761 tagcattgat ggctgcgtca ggaatctcca catggcagag gcccctgccg atctggaaca
8821 acccacctcc agcttccatg ttgggacatg ttttgcaaat gctcagaggg gaacatattt
8881 tgacggaacc ggttttgcca aagcagttgg tggattcaaa gtgggattgg accttcttgt
8941 agaatttgaa ttcgcgacaa ctacaacgac tggagttctt ctggggatca gtagtcaaaa
9001 aatggatgga atgggtattg aaatgattga tgaaaagttg atgtttcatg tggacaatgg
9061 tgcgggcaga ttcactgctg tctatgatgc tggggttcca gggcatttgt gtgatggaca
9121 atggcataaa gtcactgcca acaagatcaa acaccgcatt gagctcacag tcgatgggaa
9181 ccaggtggaa gcccaaagcc caaacccagc atctacatca gctgacacaa atgaccctgt
9241 gtttgttgga ggcttcccag atgacctcaa gcagtttggc ctaacaacca gtattccgtt
9301 ccgaggttgc atcagatccc tgaagctcac caaaggcaca gcaagccact ggaggttaat
9361 tttgccaagg ccctggaact gaggggcgtt caacctgtat catgcccagc caactaataa
9421 aaataagtgt aaccccagga agagtctgtc aaaacaagta tatcaagtaa aacaaacaaa
9481 tatattttac ctatatatgt taattaaact aatttgtgca tgtacataga attc

FIG. 1D amino acid sequence of laminin α2 subunit

MPGAAGVLLLLLLSGGLGGVQAQRPQQQRQSQAHQQRGLFPAVL

NLASNALITTNATCGEKGPEMYCKLVEHVPGQPVRNPQCRICNQNSSNPNQRHPITNA

IDGKNTWWQSPSIKNGIEYHYVTITLDLQQVFQIAYVIVKAANSPRPGNWILERSLDD

VEYKPWQYHAVTDTECLTLYNIYPRTGPPSYAKDDEVICTSFYSKIHPLENGEIHISL

INGRPSADDPSPELLEFTSARYIRLRFQRIRTLNADLMMFAHKDPREIDPIVTRRYYY

SVKDISVGGMCICYGHARACPLDPATNKSRCECEHNTCGDSCDQCCPGFHQKPWRAGT

FLTKTECEACNCHGKAEECYYDENVARRNLSLNIRGKYIGGGVCINCTQNTAGINCET

CTDGFFRPKGVSPNYPRPCQPCHCDPIGSLNEVCVKDEKHARRGLAPGSCHCKTGFGG

VSCDRCARGYTGYPDCKACNCSGLGSKNEDPCFGPCICKENVEGGDCSRCKSGFFNLQ

EDNWKGCDECFCSGVSNRCQSSYWTYGKIQDMSGWYLTDLPGRIRVAPQQDDLDSPQQ

ISISNAEARQALPHSYYWSAPAPYLGNKLPAVGGQLTFTISYDLEEEEDTERVLQLM

IILEGNDLSISTAQDEVYLHPSEEHTNVLLLKEESFTIHGTHFPVRRKEFMTVLANLK

RVLLQITYSFGMDAIFRLSSVNLESAVSYPTDGSIAAAVEVCQCPPGYTGSSCESCWP

RHRRVNGTIFGGICEPCQCFGHAESCDDVTGECLNCKDHTGGPYCDKCLPGFYGEPTK

GTSEDCQPCACPLNIPSNNFSPTCHLDRSLGLICDGCPVGYTGPRCERCAEGYFGQPS

VPGGSCQPCQCNDNLDFSIPGSCDSLSGSCLICKPGTTGRYCELCADGYFGDAVDAKN

CQPCRCNAGGSFSEVCHSQTGQCECRANVQGQRCDKCKAGTFGLQSARGCVPCNCNSF

GSKSFDCEESGQCWCQPGVTGKKCDRCAHGYFNFQEGGCTACECSHLGNNCDPKTGRC

ICPPNTIGEKCSKCAPNTWGHSITTGCKACNCSTVGSLDFQCNVNTGQCNCHPKFSGA

KCTECSRGHWNYPRCNLCDCFLPGTDATTCDSETKKCSCSDQTGQCTCKVNVEGIHCD

RCRPGKFGLDAKNPLGCSSCYCFGTTQCSEAKGLIRTWVTLKAEQTILPLVDEALQH

TTTKGIVFQHPEIVAHMDLMREDLHLEPFYWKLPEQFEGKKLMAYGGKLKYAIYFEAR

EETGFSTYNPQVIIRGGTPTHARIIVRHMAAPLIGQLTRHEIEMTEKEWKYYGDDPRV

FIG. 2A

HRTVTREDFLDILYDIHYILIKATYGNFMRQSRISEISMEVAEQGRGTTMTPPADLIE

KCDCPLGYSGLSCEACLPGFYRLRSQPGGRTPGPTLGTCVPCQCNGHSSLCDPETSIC

QNCQHHTAGDFCERCALGYYGIVKGLPNDCQQCACPLISSSNNFSPSCVAEGLDDYRC

TACPRGYEGQYCERCAPGYTGSPGNPGGSCQECECDPYGSLPVPCDPVTGFCTCRPGA

TGRKCDGCKHWHAREGWECVFCGDECTGLLLGDLARLEQMVMSINLTGPLPAPYKMLY

GLENMTQELKHLLSPQRAPERLIQLAEGNLNTLVTEMNELLTRATKVTADGEQTGQDA

ERTNTRAKSLGEFIKELARDAEAVNEKAIKLNETLGTRDEAFERNLEGLQKEIDQMIK

ELRRKNLETQKEIAEDELVAAEALLKKVKKLFGESRGENEEMEKDLREKLADYKNKVD

DAWDLLREATDKIREANRLFAVNQKNMTALEKKKEAVESGKRQIENTLKEGNDILDEA

NRLADEINSIIDYVEDIQTKLPPMSEELNDKIDDLSQEIKDRKLAEKVSQAESHAAQL

NDSSAVLDGILDEAKNISFNATAAFKAYSNIKDYIDEAEKVAKEAKDLAHEATKLATG

PRGLLKEDAKGCLQKSFRILNEAKKLANDVKENEDHLNGLKTRIENADARNGDLLRTL

NDTLGKLSAIPNDTAAKLQAVKDKARQANDTAKDVLAQITELHQNLDGLKKNYNKLAD

SVAKTNAVVKDPSKNKIIADADATVKNLEQEADRLIDKLKPIKELEDNLKKNISEIKE

LINQARKQANSIKVSVSSGGDCIRTYKPEIKKGSYNNIVVNVKTAVADNLLFYLGSAK

FIDFLAIEMRKGKVSFLWDVGSGVGRVEYPDLTIDDSYWYRIVASRTGRNGTISVRAL

DGPKASIVPSTHHSTSPPGYTILDVDANAMLFVGGLTGKLKKADAVRVITFTGCMGET

YFDNKPIGLWNFREKEGDCKGCTVSPQVEDSEGTIQFDGEGYALVSRPIRWYPNISTV

MFKFRTFSSSALLMYLATRDLRDFMSVELTDGHIKVSYDLGSGMASVVSNQNHNDGKW

KSFTLSRIQKQANISIVDIDTNQEENIATSSSGNNFGLDLKADDKIYFGGLPTLRNLS

MKARPEVNLKKYSGCLKDIEISRTPYNILSSPDYVGVTKGCSLENVYTVSFPKPGFVE

LSPVPIDVGTEINLSFSTKNESGIILLGSGGTPAPPRRKRRQTGQAYYVILLNRGRLE

VHLSTGARTMRKIVIRPEPNLFHDGREHSVHVERTRGIFTVQVDENRRYMQNLTVEQP

IEVKKLFVGGAPPEFQPSPLRNIPPFEGCIWNLVINSVPMDFARPVSFKNADIGRCAH

FIG. 2B

QKLREDEDGAAPAEIVIQPEPVPTPAFPTPTPVLTHGPCAAESEPALLIGSKQFGLSR

NSHIAIAFDDTKVKNRLTIELEVRTEAESGLLFYMAAINHADFATVQLRNGLPYFSYD

LGSGDTHTMIPTKINDGQWHKIKIMRSKQEGILYVDGASNRTISPKKADILDVVGMLY

VGGLPINYTTRRIGPVTYSIDGCVRNLHMAEAPADLEQPTSSFHVGTCFANAQRGTYF

DGTGFAKAVGGFKVGLDLLVEFEFATTTTTGVLLGISSQKMDGMGIEMIDEKLMFHVD

NGAGRFTAVYDAGVPGHLCDGQWHKVTANKIKHRIELTVDGNQVEAQSPNPASTSADT
NDPVFVGGFPDDLKQFGLTTSIPFRGCIRSLKLTKGTASHWRLILPRPWN

FIG. 2C cDNA sequence encoding laminin β1 subunit

```
   1 cccggagcag ggcgagagct cgcgtcgccg gaaaggaaga cgggaagaaa gggcaggcgg
  61 ctcggcgggc gtcttctcca ctcctctgcc gcgtccccgt ggctgcaggg agccggcatg
 121 gggcttctcc agttgctagc tttcagtttc ttagccctgt gcagagcccg agtgcgcgct
 181 caggaacccg agttcagcta cggctgcgca gaaggcagct gctatcccgc cacgggcgac
 241 cttctcatcg gccgagcaca gaagctttcg gtgacctcga cgtgcgggct gcacaagccc
 301 gaaccctact gtatcgtcag ccacttgcag gaggacaaaa aatgcttcat atgcaattcc
 361 caagatcctt atcatgagac cctgaatcct gacagccatc tcattgaaaa tgtggtcact
 421 acatttgctc caaaccgcct taagatttgg tggcaatctg aaaatggtgt ggaaaatgta
 481 actatccaac tggatttgga agcagaattc cattttactc atctcataat gactttcaag
 541 acattccgtc cagctgctat gctgatagaa cgatcgtccg actttgggaa aacctggggt
 601 gtgtatagat acttcgccta tgactgtgag gcctcgtttc aggcatttc aactggcccc
 661 atgaaaaaag tcgatgacat aatttgtgat tctcgatatt ctgacattga acctcaact
 721 gaaggagagg tgatatttcg tgctttagat cctgctttca aaatagaaga tccttatagc
 781 ccaaggatac agaatttatt aaaaattacc aacttgagaa tcaagtttgt gaaactgcat
 841 actttgggag ataaccttct ggattccagg atggaaatca gagaaaagta ttattatgca
 901 gtttatgata tggtggttcg aggaaattgc ttctgctatg gtcatgccag cgaatgtgcc
 961 cctgtggatg gattcaatga agaagtggaa ggaatggttc acggacactg catgtgcagg
1021 cataacacca agggcttaaa ctgtgaactc tgcatggatt tctaccatga tttaccttgg
1081 agacctgctg aaggccgaaa cagcaacgcc tgtaaaaaat gtaactgcaa tgaacattcc
1141 atctcttgtc actttgacat ggctgtttac ctggccacgg ggaacgtcag cggaggcgtg
1201 tgtgatgact gtcagcacaa caccatgggg cgcaactgtg agcagtgcaa gccgttttac
1261 taccagcacc cagagaggga catccgagat cctaatttct gtgaacgatg tacgtgtgac
1321 ccagctggct ctcaaaatga gggaatttgt gacagctata ctgattttc tactggtctc
1381 attgctggcc agtgtcggtg taaattaaat gtggaaggag aacattgtga tgtttgcaaa
1441 gaaggcttct atgatttaag cagtgaagat ccatttggtt gtaaatcttg tgcttgcaat
1501 cctctgggaa caattcctgg agggaatcct tgtgattccg agacaggtca ctgctactgc
1561 aagcgtctgg tgacaggaca gcattgtgac cagtgcctgc cagagcactg gggcttaagc
1621 aatgatttgg atggatgtcg accatgtgac tgtgaccttg ggggagcctt aaacaacagt
1681 tgctttgcgg agtcaggcca gtgctcatgc cggcctcaca tgattggacg tcagtgcaac
1741 gaagtggaac tggttacta ctttgccacc ctggatcact acctctatga gcggaggaa
1801 gccaacttgg ggcctggggt tagcatagtg agcggcaat atatccagga ccggattccc
1861 tcctggactg gagccggctt cgtccgagtg cctgaagggg cttatttgga gttttcatt
1921 gacaacatac catattccat ggagtacgac atcctaattc gctacgagcc acagctaccc
1981 gaccactggg aaaaagctgt catcacagtg cagcgacctg gaaggattcc aaccagcagc
2041 cgatgtggta ataccatccc gatgatgac aaccaggtgg tgtcattatc accaggctca
2101 agatatgtcg tccttcctcg gccggtgtgc tttgagaagg gaacaaacta cacggtgagg
2161 ttggagctgc ctcagtacac ctcctctgat agcgacgtgg agagccccta cacgctgatc
2221 gattctcttg ttctcatgcc atactgtaaa tcactggaca tcttcaccgt gggaggttca
2281 ggagatgggg tggtcaccaa cagtgcctgg gaaaccttc agagataccg atgtctagag
2341 aacagcagaa gcgttgtgaa acaccgatg acagatgttt gcagaaacat catctttagc
2401 atttctgccc tgttacacca gacaggcctg gcttgtgaat gcgaccctca gggttcgtta
2461 agttccgtgt gtgatcccaa cggaggccag tgccagtgcc ggcccaacgt ggttggaaga
2521 acctgcaaca gatgtgcacc tggaacttt ggctttggcc ccagtggatg caaaccttgt
2581 gagtgccatc tgcaaggatc tgtcaatgcc ttctgcaatc ccgtcactgg ccagtgccac
2641 tgtttccagg gagtgtatgc tcggcagtgt gatcggtgct acctgggca ctggggcttt
2701 ccaagttgcc agccctgcca gtgcaatggc cacgccgatg actgcgaccc agtgactggg
```

FIG. 3A

2761 gagtgcttga actgccagga ctacaccatg ggtcataact gtgaaaggtg cttggctggt
2821 tactatggcg acccatcat tgggtcaggt gatcactgcc gcccttgcc ttgcccagat
2881 ggtcccgaca gtggacgcca gtttgccagg agctgctacc aagatcctg tactttacag
2941 cttgcctgtg tttgtgatcc tggatacatt ggttccagat gtgacgactg tgcctcagga
3001 tactttggca atccatcaga agttgggggg tcgtgtcagc cttgccagtg tcacaacaac
3061 attgacacga cagacccaga agcctgtgac aaggagactg ggaggtgtct caagtgcctg
3121 taccacacgg aaggggaaca ctgtcagttc tgccggtttg gatactatgg tgatgccctc
3181 cggcaggact gtcgaaagtg tgtctgtaat tacctgggca ccgtgcaaga gcactgtaac
3241 ggctctgact gccagtgcga caaagccact ggtcagtgct tgtgtcttcc taatgtgatc
3301 gggcagaact gtgaccgctg tgcgcccaat acctggcagc tggccagtgg cactggctgt
3361 gacccatgca actgcaatgc tgctcattcc ttcgggccat cttgcaatga gttcacgggg
3421 cagtgccagt gcatgcctgg gtttggaggc cgcacctgca gcgagtgcca ggaactcttc
3481 tggggagacc ccgacgtgga gtgccagagcc tgtgactgtg accccagggg cattgagacg
3541 ccacagtgtg accagtccac gggccagtgt gtctgcgttg agggtgttga gggtccacgc
3601 tgtgacaagt gcacgcgagg gtactcgggg gtcttccctg actgcacacc ctgccaccag
3661 tgctttgctc tctgggatgt gatcattgcc gagctgacca acaggacaca cagattcctg
3721 gagaaagcca aggccttgaa gatcagtggt gtgatcgggc cttaccgtga gactgtggac
3781 tcggtggaga ggaaagtcag cgagataaaa gacatcctgg cgcagagccc cgcagcagag
3841 ccactgaaaa acattgggaa tctctttgag gaagcagaga aactgattaa agatgttaca
3901 gaaatgatgg ctcaagtaga agtgaaatta tctgacacaa cttcccaaag caacagcaca
3961 gccaaagaac tggattctct acagacagaa gccgaaagcc tagacaacac tgtgaaagaa
4021 cttgctgaac aactggaatt tatcaaaaac tcagatattc ggggtgcctt ggatagcatt
4081 accaagtatt tccagatgtc tcttgaggca gaggagaggg tgaatgcctc caccacagaa
4141 cccaacagca ctgtggagca gtcagccctc atgagagaca gagtagaaga cgtgatgatg
4201 gagcgagaat cccagttcaa ggaaaaacaa gaggagcagg ctcgcctcct tgatgaactg
4261 gcaggcaagc tacaaagcct agacctttca gccgctgccg aaatgacctg tggaacaccc
4321 ccagggggcct cctgttccga gactgaatgt ggcgggccaa actgcagaac tgacgaagga
4381 gagaggaagt gtgggggggcc tggctgtggt ggtctggtta ctgttgcaca caacgcctgg
4441 cagaaagcca tggacttgga ccaagatgtc ctgagtgccc tggctgaagt ggaacagctc
4501 tccaagatgg tctctgaagc aaaactgagg gcagatgagg caaaacaaag tgctgaagac
4561 attctgttga agacaaatgc taccaaagaa aaaatggaca agagcaatga ggagctgaga
4621 aatctaatca gcaaatcag aaactttttg acccaggata gtgctgattt ggacagcatt
4681 gaagcagttg ctaatgaagt attgaaaatg gagatgccta gcaccccaca gcagttacag
4741 aacttgacag aagatatacg tgaacgagtt gaaagccttt ctcaagtaga ggttattctt
4801 cagcatagtg ctgctgacat tgccagagct gagatgttgt tagaagaagc taaaagagca
4861 agcaaaagtg caacagatgt taaagtcact gcagatatgg taaaggaagc tctggaagaa
4921 gcagaaaagg cccaggtcgc agcagagaag gcaattaaac aagcagatga agacattcaa
4981 ggaacccaga acctgttaac ttcgattgag tctgaaacag cagcttctga ggaaaccttg
5041 ttcaacgcgt cccagcgcat cagcgagtta gagaggaatg tggaagaact taagcggaaa
5101 gctgccaaa actccggga ggcagaatat attgaaaaag tagtatatac tgtgaagcaa
5161 agtgcagaag atgttaagaa gactttagat ggtgaacttg atgaaaagta taaaaagta
5221 gaaaatttaa ttgccaaaaa aactgaagag tcagctgatg ccagaaggaa agccgaaatg
5281 ctacaaaatg aagcaaaaac tcttttagct caagcaaata gcaagctgca actgctcaaa
5341 gattagaaa gaaatatga agacaatcaa agatacttag aagataaagc tcaagaatta
5401 gcaagactgg aaggagaagt ccgttcactc ctaaaggata taagccagaa agttgctgtg
5461 tatagcacat gcttgtaaca gaggagaata aaaatggct gaggtgaaca aggtaaaaca
5521 actacattt aaaaactgac ttaatgctct tcaaaataaa acatcaccta tttaatgttt
5581 ttaatcacat tttgtatgag ttaaataaag ccc

FIG. 3B amino acid sequence of laminin β1 subunit

MGLLQLLAFSFLALCRARVRAQEPEFSYGCAEGSCYPATGDLLI

GRAQKLSVTSTCGLHKPEPYCIVSHLQEDKKCFICNSQDPYHETLNPDSHLIENVVTT

FAPNRLKIWWQSENGVENVTIQLDLEAEFHFTHLIMTFKTFRPAAMLIERSSDFGKTW

GVYRYFAYDCEASFPGISTGPMKKVDDIICDSRYSDIEPSTEGEVIFRALDPAFKIED

PYSPRIQNLLKITNLRIKFVKLHTLGDNLLDSRMEIREKYYYAVYDMVVRGNCFCYGH

ASECAPVDGFNEEVEGMVHGHCMCRHNTKGLNCELCMDFYHDLPWRPAEGRNSNACKK

CNCNEHSISCHFDMAVYLATGNVSGGVCDDCQHNTMGRNCEQCKPFYYQHPERDIRDP

NFCERCTCDPAGSQNEGICDSYTDFSTGLIAGQCRCKLNVEGEHCDVCKEGFYDLSSE

DPFGCKSCACNPLGTIPGGNPCDSETGHCYCKRLVTGQHCDQCLPEHWGLSNDLDGCR

PCDCDLGGALNNSCFAESGQCSCRPHMIGRQCNEVEPGYYFATLDHYLYEAEEANLGP

GVSIVERQYIQDRIPSWTGAGFVRVPEGAYLEFFIDNIPYSMEYDILIRYEPQLPDHW

EKAVITVQRPGRIPTSSRCGNTIPDDDNQVVSLSPGSRYVVLPRPVCFEKGTNYTVRL

ELPQYTSSDSDVESPYTLIDSLVLMPYCKSLDIFTVGGSGDGVVTNSAWETFQRYRCL

ENSRSVVKTPMTDVCRNIIFSISALLHQTGLACECDPQGSLSSVCDPNGGQCQCRPNV

VGRTCNRCAPGTFGFGPSGCKPCECHLQGSVNAFCNPVTGQCHCFQGVYARQCDRCLP

GHWGFPSCQPCQCNGHADDCDPVTGECLNCQDYTMGHNCERCLAGYYGDPIIGSGDHC

RPCPCPDGPDSGRQFARSCYQDPVTLQLACVCDPGYIGSRCDDCASGYFGNPSEVGGS

CQPCQCHNNIDTTDPEACDKETGRCLKCLYHTEGEHCQFCRFGYYGDALRQDCRKCVC

NYLGTVQEHCNGSDCQCDKATGQCLCLPNVIGQNCDRCAPNTWQLASGTGCDPCNCNA

AHSFGPSCNEFTGQCQCMPGFGGRTCSECQELFWGDPDVECRACDCDPRGIETPQCDQ

STGQCVCVEGVEGPRCDKCTRGYSGVFPDCTPCHQCFALWDVIIAELTNRTHRFLEKA

KALKISGVIGPYRETVDSVERKVSEIKDILAQSPAAEPLKNIGNLFEEAEKLIKDVTE

MMAQVEVKLSDTTSQSNSTAKELDSLQTEAESLDNTVKELAEQLEFIKNSDIRGALDS

FIG. 4A

ITKYFQMSLEAEERVNASTTEPNSTVEQSALMRDRVEDVMMERESQFKEKQEEQARLL

DELAGKLQSLDLSAAAEMTCGTPPGASCSETECGGPNCRTDEGERKCGGPGCGGLVTV

AHNAWQKAMDLDQDVLSALAEVEQLSKMVSEAKLRADEAKQSAEDILLKTNATKEKMD

KSNEELRNLIKQIRNFLTQDSADLDSIEAVANEVLKMEMPSTPQQLQNLTEDIRERVE

SLSQVEVILQHSAADIARAEMLLEEAKRASKSATDVKVTADMVKEALEEAEKAQVAAE

KAIKQADEDIQGTQNLLTSIESETAASEETLFNASQRISELERNVEELKRKAAQNSGE

AEYIEKVVYTVKQSAEDVKKTLDGELDEKYKKVENLIAKKTEESADARRKAEMLQNEA

KTLLAQANSKLQLLKDLERKYEDNQRYLEDKAQELARLEGEVRSLLKDISQKVAVYST

FIG. 4B

```
shortb4           MQFQLTLF LHLGWLSYSK AQDDCNRGAC
   b4pep          MQFQLTLF LHLGWLSYSK AQDDCNRGAC b3pep  .......... .....MRPFF LLCFALPGL. ...LHAQQ.. ...ACSRGAC b2pep  MELTSTERGR GQPLPWELRL PLLLSVLAAT LAQAPAPDVP ...GCSRGSC b1pep  .......... .....MGLLQ LLAFSFLALC RARVRAQEPE FSYGCAEGSC beta  .......... ......m.l.. lLm..ql.lf l.lgwa.ysk ....C.rGaC 51                                                100
shortb4    HPTTGDLLVG RNTQLMASST CGLSRAQKYC ILSYLEG.EQ KCSICDSRFP b4pep   HPTTGDLLVG RNTQLMASST CGLSRAQKYC ILSYLEG.EQ KCSICDSRFP b3pep   YPPVGDLLVG RTRFLRASST CGLTKPETYC ..TQYGEWQM KCCKCDSRQP b2pep   YPATADLLVG RADRLTASST CGLNGRQPYC IVSHLQD.EK KCFLCDSRRP b1pep   YPATGDLLIG RAQKLSVTST CGLHKPEPYC IVSHLQE.DK KCFICNSQDP beta   yP.tgDLLvG R.tqLmasST CGLs..q.YC i.s.l...e. KC.iCdSrfP 101                                               150
shortb4    YDPYDQPNSH TIENVTVSFE PDREKKWWQS ENGLDHVSIR LDLEALFRFS b4pep   YDPYDQPNSH TIENVTVSFE PDREKKWWQS ENGLDHVSIR LDLEALFRFS b3pep   H....NYYSH RVENVASSSG PMR...WWQS QNDVNPVSLQ LDLDRRFQLQ b2pep   FSARDNPHTH RIQNVVTSFA PQRRAAWWQS QNGIPAVTIQ LDLEAFHFT b1pep   YHETLNPDSH LIENVVTTFA PNRLKIWWQS ENGVENVTIQ LDLEAEFHFT beta   ydpydnpnsH .ieNV..sf. PdRekkWWQS eNg.dhVsiq LDLea.F.f.

151                                               200
shortb4    HLILTFKTFR PAAMLVERST DYGHNWKVFK YFAKDCATSF PNITSGQAQG b4pep   HLILTFKTFR PAAMLVERST DYGHNWKVFK YFAKDCATSF PNITSGQAQG b3pep   EVMMEFRGPM PAGMLIERSS DFGKTWRVYQ YLAADCTSTF PRVRQGRPQS   VI b2pep   HLIMTFKTFR PAAMLVERSA DFGRTWHVYR YFSYHCGADF PGVPLAPPRH b1pep   HLIMTFKTFR PAAMLIERSS DFGKTWGVYR YFAYDCEASF PGISTGPMKK beta   hlimtFktfr PAaMLvERS. DfG.tWkVy. Yfa.dCa.sF P.itsg..qg
```

FIG. 5A

```
          201                                                      250
shortb4  VGDIVCDS.K  YSDIEPSTGG  EVVLKVLDPS  FEIENPYSPY  IQDLVTLTNL b4pep  VGDIVCDS.K  YSDIEPSTGG  EVVLKVLDPS  FEIENPYSPY  IQDLVTLTNL b3pep  WQDVRCQSLP  QRPNARLNGG  KVQLNLMDLV  SGIPATQSQK  IQEVGEITNL b2pep  WDDVVCES.R  YSEIEPSTEG  EVIYRVLDPA  IPIPDPYSSR  IQNLLKITNL b1pep  VDDIICDS.R  YSDIEPSTEG  EVIFRALDPA  FKIEDPYSPR  IQNLLKITNL beta  v.DivCdS..  ysdiepstgG  eV.l.vlDp.  feIe.pySp.  IQ.l..iTNL 251                                                      300
shortb4  RINFTKLHTL  GDALLGRRQN  DSLDKYYYAL  YEMIVRGSCF  CNGHASECRP b4pep  RINFTKLHTL  GDALLGRRQN  DSLDKYYYAL  YEMIVRGSCF  CNGHASECRP b3pep  RVNFTRLAPV  PQRGYHPPS.  .....AYYAV  SQLRLQGSCF  CHGHADRCAP b2pep  RVNLTRLHTL  GDNLLDPRR.  EIREKYYYAL  YELVVRGNCF  CYGHASECAP b1pep  RIKFVKLHTL  GDNLLDSRM.  EIREKYYYAV  YDMVVRGNCF  CYGHASECAP beta  RinftkLhtl  gd.ll..rq.  ....kyYYAl  yem.vrGsCF  C.GHAseCaP 301                                                      350
shortb4  MQKMRGDVFS  PPGMVHGQCV  CQHNTDGPNC  ERCKDFFQDA  PWRPAADLQD b4pep  MQKMRGDVFS  PPGMVHGQCV  CQHNTDGPNC  ERCKDFFQDA  PWRPAADLQD b3pep  KPGASAGSTA  V..QVHDVCV  CQHNTAGPNC  ERCAPFYNNR  PWRPAEGQDA  V b2pep  APGAPAHA..  .EGMVHGACI  CKHNTRGLNC  EQCQDFYRDL  PWRPAEDGHS b1pep  VDGFNEEV..  .EGMVHGHCM  CRHNTKGLNC  ELCMDFYHDL  PWRPAEGRNS beta  m.g.r.dv..  ..gmVHgqCv  CqHNTdGpNC  ErCkdFyqd.  PWRPAedlq.

351                                                      400
shortb4  NACRSCSCNS  HSSRCHFDMT  TYLASGGLSG  GVCEDCQHNT  EGQHCDRCRP b4pep  NACRSCSCNS  HSSRCHFDMT  TYLASGGLSG  GVCEDCQHNT  EGQHCDRCRP b3pep  HECQRCDCNG  HSETCHFDPA  VFAASQGAYG  GVCDNCRDHT  EGKNCERCQL b2pep  HACRKCDRHG  HTHSCHFDMA  VYLGSGNVSG  GVCDGCQHNT  AWRHCELCRP b1pep  NACKKCNCNE  HSISCHFDMA  VYLATGNVSG  GVCDDCQHNT  MGRNCEQCKP beta  naCr.C.cn.  Hss.CHFDma  vylasgg.sG  GVCddCqhnT  eg.hCerCrp
```

FIG. 5B

```
              401                                                    450
shortb4   LFYRDPLKTI SDPYACIPCE CDPDGTISGG ICVSHSDPAL GSVAGQCLCK b4pep   LFYRDPLKTI SDPYACIPCE CDPDGTISGG ICVSHSDPAL GSVAGQCLCK b3pep   HYFRNRRPGA SIQETCISCE CDPDGAVAGA PCDP....... ..VTGQCVCK b2pep   FFYRDPTKDL RDPAVCRSCD CDPMGSQDGG RCDSHDDPAL GLVSGQCRCK b1pep   FYYQHPERDI RDPNFCERCT CDPAGSQNEG ICDSYTDFST GLIAGQCRCK beta   .fyrdplk.i sdpyaCi.Ce CDPdG..sgg iCdshsdpal g.vaGQC.CK 451                                                    500
shortb4   ENVEGAKCDQ CKPNHYGLSA TDPLGCQPCD CNPLGSLPFL T.CDVDTGQC b4pep   ENVEGAKCDQ CKPNHYGLSA TDPLGCQPCD CNPLGSLPFL T.CDVDTGQC b3pep   EHVQGERCDL CKPGFTGLTY ANPRRCHRCD CNIL...... ..........

b2pep   EHVVGTRCQQ CRDGFFGLSI SDPSGCRRCQ CNARGTVPGS TPCDPNSGSC b1pep   LNVEGEHCDV CKEGFYDLSS EDPFGCKSCA CNPLGTIPGG NPCDSETGHC beta   enVeG..Cdq CkpgfygLsa tdPlgCq.Cd CNplg.lp.l t.cdvdtgqc 501                                                    550
shortb4   LCLSYVTGAH CEECTVGYWG LGNHLHGCSP CDCDIGGAYS NVCSPKNGQC b4pep   LCLSYVTGAH CEECTVGYWG LGNHLHGCSP CDCDIGGAYS NVCSPKNGQC b3pep   .......... .......... .......... .......... ..........

b2pep   YCKRLVTGRG CDRCLPGHWG LSLDLLGCRP CDCDVGGALD PQCDEGTGQC b1pep   YCKRLVTGQH CDQCLPEHWG LSNDLDGCRP CDCDLGGALN NSCFAESGQC beta   .c...vtgah c.ec..g.wg l.n.lhgc.p cdcdigga.s nvcspkngqc 551                                                    600
shortb4   ECRPHVTGRS CSEPAPGYFF APLNFYLYEA EEATTLQGLA PLGSETFGQS b4pep   ECRPHVTGRS CSEPAPGYFF APLNFYLYEA EEATTLQGLA PLGSETFGQS b3pep   .......... .......... .......... .......... ..........

b2pep   HCRQHMVGRR CEQVQPGYFR PFLDHLIWEA ENTR...... .........G b1pep   SCRPHMIGRQ CNEVEPGYYF ATLDHYLYEA EEANL..... .........G beta   ecrph.tgrs cse.apgyff apl..ylyea eeat...... ..........
```

FIG. 5C

```
           601                                                    650
shortb4  PAVHVVLGEP VPGNPVTWTG PGFARVLPGA GLRFAVNNIP FPVDFTIAIH
                                                                     IV
   b4pep  PAVHVVLGEP VPGNPVTWTG PGFARVLPGA GLRFAVNNIP FPVDFTIAIH b3pep  .......... .......... .......... .......... ..........

b2pep  QVLDVVERLV TPGETPSWTG SGFVRLQEGQ TLEFLVASVP NAMDYDLLLR b1pep  PGVSIVERQY IQDRIPSWTG AGFVRVPEGA YLEFFIDNIP YSMEYDILIR beta  pavhvv..ep vpgnp..wtg pgf.rvl.ga gl.favnnip fp.d..i.i.

651                                                    700
shortb4  YETQSAADWT VQIV.VNPPG G...SEHCIP KTLQSKPQSF ALPAATRIML b4pep  YETQSAADWT VQIV.VNPPG G...SEHCIP KTLQSKPQSF ALPAATRIML b3pep  .......... .......... ...GSR.... .......... .........E b2pep  LEPQVPEQWA ELELIVQRPG PVPAHSLCGH LVPRDDRIQG TLQPHARYLI b1pep  YEPQLPDHWE KAVITVQRPG RIPTSSRCGN TIPDDDNQVV SLSPGSRYVV
    beta  ye.qs.adwt vqiv.v..pg g...s.hc.p kt.q..pqsf alp.atr.ml 701                                                    750
shortb4  LPTPICLEPD VQYSIDVYFS QPLQGESHAH S.....HVLV DSLGLIPQIN b4pep  LPTPICLEPD VQYSIDVYFS QPLQGESHAH S.....HVLV DSLGLIPQIN b3pep  MP........ .......... .......... .......... ..........

b2pep  FPNPVCLEPG ISYKLHLKLV R.TGGSAQPE TPYSGPGLLI DSLVLLPRVL b1pep  LPRPVCFEKG TNYTVRLELP QYTSSDSDVE SPYT....LI DSLVLMPYCK beta  lPtp.clep. vqysid.y.s q..qgesha. s.......l. dsl.lipqin 751                                                    800
shortb4  SLENF..... ....CSKQDL DEYQLHNCVE IASAMGPQVL PGACERLIIS b4pep  SLENF..... ....CSKQDL DEYQLHNCVE IASAMGPQVL PGACERLIIS b3pep  .......... .......... .......... .......... ..........

b2pep  VLEMF....S GGDAAALERQ ATFERYQCHE EGLVPSKTSP SEACAPLLIS b1pep  SLDIFTVGGS GDGVVTNSAW ETFQRYRCLE NSRSVVKTPM TDVCRNIIFS beta  slenf..... ....cskqdl d..q..ncve iasamg..vl pgacerliis
```

FIG. 5D

```
         801                                                      850
shortb4  MSAKLHDGAV ACKCHPQGSV GSSCSRLGGQ CQCKPLVVGR CCDRCSTGSY b4pep    MSAKLHDGAV ACKCHPQGSV GSSCSRLGGQ CQCKPLVVGR CCDRCSTGSY b3pep    .......... .......... .......... .......... ..........

b2pep    LSTLIYNGAL PCQCNPQGSL SSECNPHGGQ CLCKPGVVGR RCDTCAPGYY b1pep    ISALLHQTGL ACECDPQGSL SSVCDPNGGQ CQCRPNVVGR TCNRCAPGTF beta     msa.lhdga. ackchpqgs. .sscs.lggq cqckplvvgr ccdrc..gsy 851                                                      900
shortb4  DLGHHGCHPC HCHPQGSKDT VCDQVTGQCP CHGEVSGRRC DRCLAGYFGF b4pep    DLGHHGCHPC HCHPQGSKDT VCDQVTGQCP CHGEVSGRRC DRCLAGYFGF b3pep    .......... .......... .......... .......... ..........

b2pep    GFGPTGCQAC QCSPRGALSS LCERTSGQCL CRTGAFGLRC DACQRGQWGF b1pep    GFGPSGCKPC ECHLQGSVNA FCNPVTGQCH CFGVYARQC  DRCLPGHWGF beta     ..g.hgchpc hchpqgskdt vcdqvtgqcp chg.vsgrrc drclagy.gf 901                                                      950
shortb4  PSCHPCPCNR FAELCDPETG SCFNCGGFTT GRNCERCIDG YYGNP..SSG b4pep    PSCHPCPCNR FAELCDPETG SCFNCGGFTT GRNCERCIDG YYGNP..SSG b3pep    .......... .......... .......... .......... ..........

b2pep    PSCRPCVCNG HADECNTHTG ACLGCRDLTG GEHCERCIAG FHGDPRLPYG b1pep    PSCQPCQCNG HADDCDPVTG ECLNCQDYTM GHNCERCLAG YYGDPIIGSG beta     pschpcpcn. .a.lcdpetg sc.ncg.ftt grncerci.g yyg.p..ssg 951                                                     1000
shortb4  QPCRPCLCPD DPSSNQYFAH SCYQNLWSSD VICNCLQGYT GTQCGECSTG b4pep    QPCRPCLCPD DPSSNQYFAH SCYQNLWSSD VICNCLQGYT GTQCGECSTG b3pep    .......... .......... .......... .......... ..........

b2pep    AQCRPCPCPE GPGSQRHFAT SCHQDEYSQQ IVCHCRAGYT GLRCEACAPG b1pep    DHCRPCPCPD GPDSGRQFAR SCYQDPVTLQ LACVCDPGYI GSRCDDCASG
```

FIG. 5E

```
    beta  qpcrpc.cpd .pssn.yfah scyq.lwss. vicnclqgyt gt.cgec.tg 1001                                              1050
shortb4  FYGNPRISGA PCQPCACNNN IDVTDPESCS RVTGECLRCL HNTQGANCQL b4pep  FYGNPRISGA PCQPCACNNN IDVTDPESCS RVTGECLRCL HNTQGANCQL b3pep  .......... .......... .......... .......... ..........

b2pep  QFGDPSRPGG RCQLCECSGN IDPMDPDACD PHPGQCLRCL HHTEGPHCAH
   b1pep  YFGNPSEVGG SCQPCQCHNN IDTTDPEACD KETGRCLKCL YHTEGEHCQF beta  f.gnp.isg. pcqpcacnnn idvtdpe.c. rvtgeclrcl h.t.ga.cql 1051                                              1100
shortb4  CKPGHYGSAL NQTCRRCSCH ASGVSPMECP PGGGACLCDP VTGACPCLPN b4pep  CKPGHYGSAL NQTCRRCSCH ASGVSPMECP PGGGACLCDP VTGACPCLPN b3pep  .......... .......... .......... ......CDE ESGRCLCLPN b2pep  SKPGFHGQAA RQSCHRCTCN LLGTNPQQCP SPD.QCHCDP SSGQCPCLPN
   b1pep  CRFGYYGDAL RQDCRKCVCN YLGTVQEHCN GSD..CQCDK ATGQCLCLPN beta  ckpghygsal .qtcrrcsc. a.g.spmecp pg...clCDp vtG.CpCLPN 1101                                              1150
shortb4  VTGLACDRCA DGYWNLVPGR GCQSCDCDPR TSQSSHCDQA RYFKAY b4pep  VTGLACDRCA DGYWNLVPGR GCQSCDCDPR TSQSSHCDQL TGQCPCKLGY b3pep  VVGPKCDQCA PYHWKLASGQ GCEPCACDPH NSLSPQCNQF TGQCPCREGF b2pep  VQALAVDRCA PNFWNLTSGH GCQPCACLPS PEEGPTCNEF TGQCHCLCGF
   b1pep  VIGQNCDRCA PNTWQLASGT GCDPCNCNAA HSFGPSCNEF TGQCQCMPGF beta  VtglacDrCA p.yWnL.sGr GCqpC.Cdpr tsqsphCnqf tgqcpc..Gf 1151                                              1200
   b4pep  GGKRCS.... .ECQENYYGD PPGRCIPCDC NRAGTQKPIC DPDTGMCRCR b3pep  GGLMCSAAAI RQCPDRTYGD VATGCRACDC DFRGTEGPGC DKASGRCLCR b2pep  GGRTCS.... .ECQELHWGD PGLQCHACDC DSRGIDTPQC HRFTGHCTCR
   b1pep  GGRTCS.... .ECQELFWGD PDVECRACDC DPRGIETPQC DQSTGQCVCV beta  GGrtCS.... .eCqel..GD p...CraCDC d.rG.etPqC d..tG.C.Cr
```

FIG. 5F

```
       1201                                                    1250
b4pep  EGVSGQRCDR CARGHSQEFP TCLQCHLCFD QWDHTISSLS KAVQGLMRLA
b3pep  PGLTGPRCDQ CQRGYCNRYP VCVACHPCFQ TYDADLREQA LRFGRLPNAT
b2pep  PGVSGVRCDQ CARGFSGIFP ACHPCHACFG DWDRVVQDLA ARTQRLEQRA
b1pep  EGVEGPRCDK CTRGYSGVFP DCTPCHQCFA LWDVIIAELT NRTHRFLEKA
beta   .GvsGpRCDq CaRGysg.fP .C.pCH.CF. .wD..i.ela .rtqrl...a 1251                                                    1300
b4pep  ANMEDKRETL PVCEADFKDL RGNVSEIERI L......KHP VFPSGK.FLK    ||
b3pep  ASLWSGPGLE D.RGL.ASRI LDAKSKIEQI RAVLSSPAVT EQEVAQVASA
b2pep  QELQQTGVLG AFESS.FWHM QEKLGIVQGI VGARNTSAAS TAQLVEATEE
b1pep  KALKISGVIG PYRET.VDSV ERKVSEIKDI L.AQSPAAEP LKNIGNLFEE
beta   a.l...gvlg p.re..f... ..kvseie.I l.a.s..a.p ....g..fee 1301                                                    1350
b4pep  VKDYHDSVRR QIMQLNEQLK .AVYEFQDLK DTIERAKNEA DLLLEDLQEE
b3pep  ILSLRRTLQG L..QLDLPLE EET...LSLP RDLESLDRSF NGLLTMYQRK
b2pep  LRREIGEATE HLTQLEADLT DVQDENFNAN HALSGLERDR LALNLTLRQL
b1pep  AEKLIKDVTE MMAQVEVKLS DTTSQSNSTA KELDSLQTEA ESLDNTVKEL
beta   ...li..vte ...Qle..L. d.t.e..sl. ..lesl.rea ..Ll.tlqel 1351                                                    1400
b4pep  IDLQSSVLNA SIADSSENIK KYYHISSSAE KKIN....ET SSTINTSANT
b3pep  REQFEKISSA DPSGAFRMLS TAYEQSAQAA QQVS...... .....DSSRL
b2pep  DQHLDLLKHS NFLGAYDSIR HAHSQSAEAE RRANTSALAV PSPVSNSASA
b1pep  AEQLEFIKNS DIRGALDSIT KYFQMSLEAE ERVNASTTEP NSTVEQSALM
beta   .eqle.ikn. di.ga.dsi. k.y.qSaeAe .rvn....e. .stv...Sa..

1401                                                    1450
b4pep  RNDLLTIL.. ......DTLT SKGNLSLERL KQIKIPDIQI LNEKV.....    α
b3pep  LDQLRDSRRE AERLVRQAGG GGGTGSPKLV A..LRLEMSS LPDLTPTFNK
```

FIG. 5G

```
b2pep  RHRTEALMDA QKEDFNSKHM ANQRALGKLS AHTHTLSLTD INELV.....
b1pep  RDRVEDVMME RESQFKEKQE EQARLLDELA GKLQSLDLSA AAEMT.....
beta   rdrled.m.e .e..f..k.. ..grl...1. a....ldls. lnel......

1451                                              1500
b4pep  .CGDPGNVPC VPLPCGGALC TGRKGHRKCR GPGCHGSLTL STNALQKAQE
b3pep  LCGNSRQMAC TPISCPGELC PQDNG.TAC. ASRCRGVLPR AGGAFLMAGQ
b2pep  .CGAQGLHHD RTSPCGGAGC RDEDGQPRCG GLSCNGAAAT ADLALGRARH
b1pep  .CGTPPGASC SETECGGPNC RTDEGERKCG GPGCGGLVTV AHNAWQKAMD
beta   .CG.pg...c .p.pCgGalC r.d.G.rkCg gpgC.G.lt. a.nAlqkA..

1501                                              1550
b4pep  AKSIIRNLDK QVRGLKNQIE SISEQAEVSK NNALQLREKL GNIRNQSDSE
b3pep  VAEQLRGFNA QLQRTRQMIR AAEESASQIQ SSAQRLETQV SASRSQMEED
b2pep  TQAELQRALA EGGSILSRVA ETRRQASEAQ QRAQAALDKA NASRGQVEQA
b1pep  LDQDVLSALA EVEQLSKMVS EAKLRADEAK QSAEDILLKT NATKEKMDKS
beta   ....lr.ala .v..l..m.. ea.eqAsea. qsAq.ll.k. nasr.qm...

1551                                              1600
b4pep  EENINLFIKK VKNFLLEENV PPEDIEKVAN GVLDIHLPIP SQNLTDELVK
b3pep  VRRTRLLIQQ VRDFLTDPDT DAATIQEVSE AVLALWLPTD SATVLQKMNE
b2pep  NQELQELIQS VKDFLNQEGA DPDSIEMVAT RVLELSIPAS AEQIQHLAGA
b1pep  NEELRNLIKQ IRNFLTQDSA DLDSIEAVAN EVLKMEMPST PQQLQNLTED
beta   neelrlll.q v..FLtqe.a dpdsIe.Van .VL.l.lP.. sqqlq.l...

1601                                              1650
b4pep  IQKHMQLCED YRTDENRSNE EADGAQKLLV KAKAAEKAA. NILLNLDKTL
b3pep  IQAIAARLPN VDLVLSQTKQ DIARARRLQA EAEEEARSRAH AVEGQVEDVV
b2pep  IAERVRSLAD VDAILARTVG DVRRAEQLLQ DARRARSWAE DEKQKAETVQ
b1pep  IRERVESLSQ VEVILQHSAA DIARAEMLLE EAKRASKSAT DVKVTADMVK
beta   Iqerv.sl.d vd.il.r... diarAe.Ll. eAkrAr...A. dvk...a...v.
```

FIG. 5H

```
          1651                                                    1700
b4pep  NQLQQAQITQ GRANSTITQL TANITKIKKN VLQAENQTRE MKSELELAKQ
b3pep  GNLRQGTVAL QEAQDTMQGT SRSLRLIQDR VAEVQQVLRP AEKLVTSMTK
b2pep  AALEEAQRAQ GIAQGAIRGA VADTRDTEQT LYQVQERMAG AERALSSAGE
b1pep  EALEEAEKAQ VAAEKAIKQA DEDIQGTQNL LTSIESETAA SEETLFNASQ
beta   .aLe.aq.aq g.Aq..i...a .adir..q.. ..qv...t.. ae..l.sa.q 1701                                                    1750
b4pep  R.SGLEDGLS LLQTKLQRHQ DHAVNAKVQA ESAQHQAGSL EKEF.VELKK
b3pep  QLGDFWTRME ELRHQARQQG AEAVQAQQLA EGASEQALSA QEGFE.RIKQ
b2pep  RARQLDALLE ALKLKRAGNS LAASTAEETA GSAQGRAQEA EQLLRGPLGD
b1pep  RISELERNVE ELKRKAAQNS GEAEYIEKVV YTVKQSAEDV KKTLDGELDE
beta   r.s.le..le eLk.kaaqns .eAv.ae..a esaq.qA.sa ek...gelk.

1751                                                    1800
b4pep  QYAILQRK.T STTGLTKETL GKVKQLKDAA EKLAGDTEAK IRRITDLERK
b3pep  KYAELKDRLG QSSMLGEQGA R.IQSVKTEA EELFGETMEM MDRMKDMELE
b2pep  QYQTVKALAE RKAQGVLAAQ ARAEQLPDEA RDLLQAAQDK LQRLQELEGT
b1pep  KYKKVENLIA KKTEESADAR RKAEMLQNEA KTLLAQANSK LQLLKDLERK
beta   .Ya..k.l.. .kt.l...a. rkaeqlkdeA e.Llg....k lqrlkdlErk 1801                                        1841
b4pep  IQDLNLSRQA KADQLRILED QVVAIKNEIV EQEKKYARCY S
b3pep  LLRGSQAIML RSADLTGLEK RVEQIRDHIN GRVLYYATCK
b2pep  YEENERALES KAAQLDGLEA RMRSVLQAIN LQVQIYNTCQ
b1pep  YEDNQRYLED KAQELARLEG EVRSLLKDIS QKVAVYSTCL
beta   yedn.rale. kaaqL.gLE. rvrsil..In .qv..YatC. S
```

FIG. 5I

SEQUENCE LISTING

<160> NUMBER OF SEQ ID NOS: 13

<210> SEQ ID NO 1
<211> LENGTH: 1761
<212> TYPE: PRT
<213> ORGANISM: Homo sapiens

<400> SEQUENCE: 1

```
Met Gln Phe Gln Leu Thr Leu Phe Leu His Leu Gly Trp Leu Ser Tyr
 1               5                  10                  15

Ser Lys Ala Gln Asp Asp Cys Asn Arg Gly Ala Cys His Pro Thr Thr
            20                  25                  30

Gly Asp Leu Leu Val Gly Arg Asn Thr Gln Leu Met Ala Ser Ser Thr
        35                  40                  45

Cys Gly Leu Ser Arg Ala Gln Lys Tyr Cys Ile Leu Ser Tyr Leu Glu
    50                  55                  60

Gly Glu Gln Lys Cys Ser Ile Cys Asp Ser Arg Phe Pro Tyr Asp Pro
65                  70                  75                  80

Tyr Asp Gln Pro Asn Ser His Thr Ile Glu Asn Val Thr Val Ser Phe
                85                  90                  95

Glu Pro Asp Arg Glu Lys Lys Trp Trp Gln Ser Glu Asn Gly Leu Asp
            100                 105                 110

His Val Ser Ile Arg Leu Asp Leu Glu Ala Leu Phe Arg Phe Ser His
        115                 120                 125

Leu Ile Leu Thr Phe Lys Thr Phe Arg Pro Ala Ala Met Leu Val Glu
    130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
        195                 200                 205

Ile Glu Asn Pro Tyr Ser Pro Tyr Ile Gln Asp Leu Val Thr Leu Thr
```

```
              210                 215                 220
Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Tyr Ala Leu
                245                 250                 255

Tyr Glu Met Ile Val Arg Gly Ser Cys Phe Cys Asn Gly His Ala Ser
                260                 265                 270

Glu Cys Arg Pro Met Gln Lys Met Arg Gly Asp Val Phe Ser Pro Pro
                275                 280                 285

Gly Met Val His Gly Gln Cys Val Cys Gln His Asn Thr Asp Gly Pro
290                 295                 300

Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
                325                 330                 335

His Ser Ser Arg Cys His Phe Asp Met Thr Thr Tyr Leu Ala Ser Gly
                340                 345                 350

Gly Leu Ser Gly Gly Val Cys Glu Asp Cys Gln His Asn Thr Glu Gly
                355                 360                 365

Gln His Cys Asp Arg Cys Arg Pro Leu Phe Tyr Arg Asp Pro Leu Lys
                370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
                405                 410                 415

Gly Ser Val Ala Gly Gln Cys Leu Cys Lys Glu Asn Val Glu Gly Ala
                420                 425                 430

Lys Cys Asp Gln Cys Lys Pro Asn His Tyr Gly Leu Ser Ala Thr Asp
                435                 440                 445

Pro Leu Gly Cys Gln Pro Cys Asp Cys Asn Pro Leu Gly Ser Leu Pro
450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
                485                 490                 495

Gly Asn His Leu His Gly Cys Ser Pro Cys Asp Cys Asp Ile Gly Gly
                500                 505                 510

Ala Tyr Ser Asn Val Cys Ser Pro Lys Asn Gly Gln Cys Glu Cys Arg
                515                 520                 525

Pro His Val Thr Gly Arg Ser Cys Ser Glu Pro Ala Pro Gly Tyr Phe
                530                 535                 540

Phe Ala Pro Leu Asn Phe Tyr Leu Tyr Glu Ala Glu Ala Thr Thr
545                 550                 555                 560

Leu Gln Gly Leu Ala Pro Leu Gly Ser Glu Thr Phe Gly Gln Ser Pro
                565                 570                 575

Ala Val His Val Val Leu Gly Glu Pro Val Pro Gly Asn Pro Val Thr
                580                 585                 590

Trp Thr Gly Pro Gly Phe Ala Arg Val Leu Pro Gly Ala Gly Leu Arg
                595                 600                 605

Phe Ala Val Asn Asn Ile Pro Phe Pro Val Asp Phe Thr Ile Ala Ile
                610                 615                 620

His Tyr Glu Thr Gln Ser Ala Ala Asp Trp Thr Val Gln Ile Val Val
625                 630                 635                 640
```

-continued

Asn Pro Pro Gly Gly Ser Glu His Cys Ile Pro Lys Thr Leu Gln Ser
            645                 650                 655

Lys Pro Gln Ser Phe Ala Leu Pro Ala Ala Thr Arg Ile Met Leu Leu
            660                 665                 670

Pro Thr Pro Ile Cys Leu Glu Pro Asp Val Gln Tyr Ser Ile Asp Val
            675                 680                 685

Tyr Phe Ser Gln Pro Leu Gln Gly Glu Ser His Ala His Ser His Val
        690                 695                 700

Leu Val Asp Ser Leu Gly Leu Ile Pro Gln Ile Asn Ser Leu Glu Asn
705                 710                 715                 720

Phe Cys Ser Lys Gln Asp Leu Asp Glu Tyr Gln Leu His Asn Cys Val
                725                 730                 735

Glu Ile Ala Ser Ala Met Gly Pro Gln Val Leu Pro Gly Ala Cys Glu
                740                 745                 750

Arg Leu Ile Ile Ser Met Ser Ala Lys Leu His Asp Gly Ala Val Ala
            755                 760                 765

Cys Lys Cys His Pro Gln Gly Ser Val Gly Ser Ser Cys Ser Arg Leu
770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
            805                 810                 815

Cys His Cys His Pro Gln Gly Ser Lys Asp Thr Val Cys Asp Gln Val
            820                 825                 830

Thr Gly Gln Cys Pro Cys His Gly Glu Val Ser Gly Arg Arg Cys Asp
            835                 840                 845

Arg Cys Leu Ala Gly Tyr Phe Gly Phe Pro Ser Cys His Pro Cys Pro
850                 855                 860

Cys Asn Arg Phe Ala Glu Leu Cys Asp Pro Glu Thr Gly Ser Cys Phe
865                 870                 875                 880

Asn Cys Gly Gly Phe Thr Thr Gly Arg Asn Cys Glu Arg Cys Ile Asp
            885                 890                 895

Gly Tyr Tyr Gly Asn Pro Ser Ser Gly Gln Pro Cys Arg Pro Cys Leu
        900                 905                 910

Cys Pro Asp Asp Pro Ser Ser Asn Gln Tyr Phe Ala His Ser Cys Tyr
        915                 920                 925

Gln Asn Leu Trp Ser Ser Asp Val Ile Cys Asn Cys Leu Gln Gly Tyr
        930                 935                 940

Thr Gly Thr Gln Cys Gly Glu Cys Ser Thr Gly Phe Tyr Gly Asn Pro
945                 950                 955                 960

Arg Ile Ser Gly Ala Pro Cys Gln Pro Cys Ala Cys Asn Asn Asn Ile
            965                 970                 975

Asp Val Thr Asp Pro Glu Ser Cys Ser Arg Val Thr Gly Glu Cys Leu
            980                 985                 990

Arg Cys Leu His Asn Thr Gln Gly Ala Asn Cys Gln Leu Cys Lys Pro
        995                 1000                1005

Gly His Tyr Gly Ser Ala Leu Asn Gln Thr Cys Arg Arg Cys Ser Cys
    1010                1015                1020

His Ala Ser Gly Val Ser Pro Met Glu Cys Pro Pro Gly Gly Gly Ala
1025                1030                1035                1040

Cys Leu Cys Asp Pro Val Thr Gly Ala Cys Pro Cys Leu Pro Asn Val
            1045                1050                1055

```
Thr Gly Leu Ala Cys Asp Arg Cys Ala Asp Gly Tyr Trp Asn Leu Val
            1060                1065                1070

Pro Gly Arg Gly Cys Gln Ser Cys Asp Cys Asp Pro Arg Thr Ser Gln
            1075                1080                1085

Ser Ser His Cys Asp Gln Leu Thr Gly Gln Cys Pro Cys Lys Leu Gly
            1090                1095                1100

Tyr Gly Gly Lys Arg Cys Ser Glu Cys Gln Glu Asn Tyr Tyr Gly Asp
1105                1110                1115                1120

Pro Pro Gly Arg Cys Ile Pro Cys Asp Cys Asn Arg Ala Gly Thr Gln
            1125                1130                1135

Lys Pro Ile Cys Asp Pro Asp Thr Gly Met Cys Arg Cys Arg Glu Gly
            1140                1145                1150

Val Ser Gly Gln Arg Cys Asp Arg Cys Ala Arg Gly His Ser Gln Glu
            1155                1160                1165

Phe Pro Thr Cys Leu Gln Cys His Leu Cys Phe Asp Gln Trp Asp His
            1170                1175                1180

Thr Ile Ser Ser Leu Ser Lys Ala Val Gln Gly Leu Met Arg Leu Ala
1185                1190                1195                1200

Ala Asn Met Glu Asp Lys Arg Glu Thr Leu Pro Val Cys Glu Ala Asp
            1205                1210                1215

Phe Lys Asp Leu Arg Gly Asn Val Ser Glu Ile Glu Arg Ile Leu Lys
            1220                1225                1230

His Pro Val Phe Pro Ser Gly Lys Phe Leu Lys Val Lys Asp Tyr His
            1235                1240                1245

Asp Ser Val Arg Arg Gln Ile Met Gln Leu Asn Glu Gln Leu Lys Ala
            1250                1255                1260

Val Tyr Glu Phe Gln Asp Leu Lys Asp Thr Ile Glu Arg Ala Lys Asn
1265                1270                1275                1280

Glu Ala Asp Leu Leu Leu Glu Asp Leu Gln Glu Glu Ile Asp Leu Gln
            1285                1290                1295

Ser Ser Val Leu Asn Ala Ser Ile Ala Asp Ser Ser Glu Asn Ile Lys
            1300                1305                1310

Lys Tyr Tyr His Ile Ser Ser Ala Glu Lys Lys Ile Asn Glu Thr
            1315                1320                1325

Ser Ser Thr Ile Asn Thr Ser Ala Asn Thr Arg Asn Asp Leu Leu Thr
            1330                1335                1340

Ile Leu Asp Thr Leu Thr Ser Lys Gly Asn Leu Ser Leu Glu Arg Leu
1345                1350                1355                1360

Lys Gln Ile Lys Ile Pro Asp Ile Gln Ile Leu Asn Glu Lys Val Cys
            1365                1370                1375

Gly Asp Pro Gly Asn Val Pro Cys Val Pro Leu Pro Cys Gly Gly Ala
            1380                1385                1390

Leu Cys Thr Gly Arg Lys Gly His Arg Lys Cys Arg Gly Pro Gly Cys
            1395                1400                1405

His Gly Ser Leu Thr Leu Ser Thr Asn Ala Leu Gln Lys Ala Gln Glu
            1410                1415                1420

Ala Lys Ser Ile Ile Arg Asn Leu Asp Lys Gln Val Arg Gly Leu Lys
1425                1430                1435                1440

Asn Gln Ile Glu Ser Ile Ser Glu Gln Ala Glu Val Ser Lys Asn Asn
            1445                1450                1455

Ala Leu Gln Leu Arg Glu Lys Leu Gly Asn Ile Arg Asn Gln Ser Asp
            1460                1465                1470

Ser Glu Glu Glu Asn Ile Asn Leu Phe Ile Lys Lys Val Lys Asn Phe
```

```
              1475              1480              1485
Leu Leu Glu Glu Asn Val Pro Pro Glu Asp Ile Glu Lys Val Ala Asn
    1490              1495              1500

Gly Val Leu Asp Ile His Leu Pro Ile Pro Ser Gln Asn Leu Thr Asp
1505              1510              1515              1520

Glu Leu Val Lys Ile Gln Lys His Met Gln Leu Cys Glu Asp Tyr Arg
            1525              1530              1535

Thr Asp Glu Asn Arg Ser Asn Glu Glu Ala Asp Gly Ala Gln Lys Leu
    1540              1545              1550

Leu Val Lys Ala Lys Ala Ala Glu Lys Ala Ala Asn Ile Leu Leu Asn
    1555              1560              1565

Leu Asp Lys Thr Leu Asn Gln Leu Gln Gln Ala Gln Ile Thr Gln Gly
    1570              1575              1580

Arg Ala Asn Ser Thr Ile Thr Gln Leu Thr Ala Asn Ile Thr Lys Ile
1585              1590              1595              1600

Lys Lys Asn Val Leu Gln Ala Glu Asn Gln Thr Arg Glu Met Lys Ser
            1605              1610              1615

Glu Leu Glu Leu Ala Lys Gln Arg Ser Gly Leu Glu Asp Gly Leu Ser
    1620              1625              1630

Leu Leu Gln Thr Lys Leu Gln Arg His Gln Asp His Ala Val Asn Ala
    1635              1640              1645

Lys Val Gln Ala Glu Ser Ala Gln His Gln Ala Gly Ser Leu Glu Lys
    1650              1655              1660

Glu Phe Val Glu Leu Lys Lys Gln Tyr Ala Ile Leu Gln Arg Lys Thr
1665              1670              1675              1680

Ser Thr Thr Gly Leu Thr Lys Glu Thr Leu Gly Lys Val Lys Gln Leu
            1685              1690              1695

Lys Asp Ala Ala Glu Lys Leu Ala Gly Asp Thr Glu Ala Lys Ile Arg
    1700              1705              1710

Arg Ile Thr Asp Leu Glu Arg Lys Ile Gln Asp Leu Asn Leu Ser Arg
    1715              1720              1725

Gln Ala Lys Ala Asp Gln Leu Arg Ile Leu Glu Asp Gln Val Val Ala
    1730              1735              1740

Ile Lys Asn Glu Ile Val Glu Gln Glu Lys Lys Tyr Ala Arg Cys Tyr
1745              1750              1755              1760

Ser

<210> SEQ ID NO 2
<211> LENGTH: 5874
<212> TYPE: DNA
<213> ORGANISM: Homo sapiens
<220> FEATURE:
<221> NAME/KEY: CDS
<222> LOCATION: (81)...(5363)

<400> SEQUENCE: 2
acatgccccg tttgctgcct gaacctctcc acaaagactc ccagatcctg aattgaattt    60
aatcatctcc tgacaaaaga atg caa ttt caa ctg acc ctt ttt ttg cac ctt   113
                      Met Gln Phe Gln Leu Thr Leu Phe Leu His Leu
                       1               5                  10 ggg tgg ctc agt tac tca aaa gct caa gat gac tgc aac agg ggt gcc    161
Gly Trp Leu Ser Tyr Ser Lys Ala Gln Asp Asp Cys Asn Arg Gly Ala
         15                  20                  25 tgt cat ccc acc act ggt gat ctc ctg gtg ggc agg aac acg cag ctt    209
Cys His Pro Thr Thr Gly Asp Leu Leu Val Gly Arg Asn Thr Gln Leu
     30                  35                  40
```

-continued

```
atg gct tct tct acc tgt ggg ctg agc aga gcc cag aaa tac tgc atc      257
Met Ala Ser Ser Thr Cys Gly Leu Ser Arg Ala Gln Lys Tyr Cys Ile
    45                  50                  55 ctc agt tac ctg gag ggg gaa caa aaa tgc tcc atc tgt gac tct aga      305
Leu Ser Tyr Leu Glu Gly Glu Gln Lys Cys Ser Ile Cys Asp Ser Arg
60                  65                  70                  75 ttt cca tat gat ccg tat gac caa ccc aac agc cac acc att gag aat      353
Phe Pro Tyr Asp Pro Tyr Asp Gln Pro Asn Ser His Thr Ile Glu Asn
                80                  85                  90 gtc act gta agt ttt gaa cca gac aga gaa aag aaa tgg tgg caa tct      401
Val Thr Val Ser Phe Glu Pro Asp Arg Glu Lys Lys Trp Trp Gln Ser
            95                  100                 105 gaa aat ggt ctt gat cat gtc agc atc aga ctg gac tta gag gca tta      449
Glu Asn Gly Leu Asp His Val Ser Ile Arg Leu Asp Leu Glu Ala Leu
        110                 115                 120 ttt cgg ttc agc cac ctt atc ctg acc ttt aag act ttt cgg cct gct      497
Phe Arg Phe Ser His Leu Ile Leu Thr Phe Lys Thr Phe Arg Pro Ala
    125                 130                 135 gca atg tta gtt gaa cgt tcc aca gac tat gga cac aac tgg aaa gtg      545
Ala Met Leu Val Glu Arg Ser Thr Asp Tyr Gly His Asn Trp Lys Val
140                 145                 150                 155 ttc aaa tat ttt gca aaa gac tgt gcc act tcc ttt cct aac atc aca      593
Phe Lys Tyr Phe Ala Lys Asp Cys Ala Thr Ser Phe Pro Asn Ile Thr
                160                 165                 170 tct ggc cag gcc cag gga gtg gga gac att gtt tgt gac tcc aaa tac      641
Ser Gly Gln Ala Gln Gly Val Gly Asp Ile Val Cys Asp Ser Lys Tyr
            175                 180                 185 tcg gat att gaa ccc tca aca ggt gga gag gtt gtt tta aaa gtt ttg      689
Ser Asp Ile Glu Pro Ser Thr Gly Gly Glu Val Val Leu Lys Val Leu
        190                 195                 200 gat ccc agt ttt gaa att gaa aac cct tat agc ccc tac atc caa gac      737
Asp Pro Ser Phe Glu Ile Glu Asn Pro Tyr Ser Pro Tyr Ile Gln Asp
    205                 210                 215 ctt gtg aca ttg aca aac ctg agg ata aac ttt acc aag ctc cac acc      785
Leu Val Thr Leu Thr Asn Leu Arg Ile Asn Phe Thr Lys Leu His Thr
220                 225                 230                 235 ctt ggg gat gct ttg ctt gga agg agg caa aat gat tcc ctt gat aaa      833
Leu Gly Asp Ala Leu Leu Gly Arg Arg Gln Asn Asp Ser Leu Asp Lys
                240                 245                 250 tac tac tat gct ctg tac gag atg att gtt cgg gga agc tgc ttt tgc      881
Tyr Tyr Tyr Ala Leu Tyr Glu Met Ile Val Arg Gly Ser Cys Phe Cys
            255                 260                 265 aat ggc cat gct agc gaa tgt cgc cct atg cag aag atg cgg gga gat      929
Asn Gly His Ala Ser Glu Cys Arg Pro Met Gln Lys Met Arg Gly Asp
        270                 275                 280 gtt ttc agc cct cct gga atg gtt cac ggt cag tgt gtg tgt cag cac      977
Val Phe Ser Pro Pro Gly Met Val His Gly Gln Cys Val Cys Gln His
    285                 290                 295 aat aca gat ggt ccg aac tgt gag aga tgc aag gac ttc ttc cag gat    1025
Asn Thr Asp Gly Pro Asn Cys Glu Arg Cys Lys Asp Phe Phe Gln Asp
300                 305                 310                 315 gct cct tgg agg cca gct gca gac ctc cag gac aac gct tgc aga tcg    1073
Ala Pro Trp Arg Pro Ala Ala Asp Leu Gln Asp Asn Ala Cys Arg Ser
                320                 325                 330 tgc agc tgt aat agc cac tcc agc cgc tgt cac ttt gac atg act acg    1121
Cys Ser Cys Asn Ser His Ser Ser Arg Cys His Phe Asp Met Thr Thr
            335                 340                 345 tac ctg gca agc ggt ggc ctc agc ggg ggc gtg tgt gaa gac tgc cag    1169
Tyr Leu Ala Ser Gly Gly Leu Ser Gly Gly Val Cys Glu Asp Cys Gln
```

|  |  |
|---|---|
| cac aac act gag ggg cag cac tgc gac cgc tgc aga ccc ctc ttc tac<br>His Asn Thr Glu Gly Gln His Cys Asp Arg Cys Arg Pro Leu Phe Tyr<br>365               370               375 | 1217 |
| agg gac ccg ctc aag acc atc tca gat ccc tac gcg tgc att cct tgt<br>Arg Asp Pro Leu Lys Thr Ile Ser Asp Pro Tyr Ala Cys Ile Pro Cys<br>380               385               390               395 | 1265 |
| gaa tgt gac ccc gat ggg acc ata tct ggt ggc att tgt gtg agc cac<br>Glu Cys Asp Pro Asp Gly Thr Ile Ser Gly Gly Ile Cys Val Ser His<br>                        400               405               410 | 1313 |
| tct gat cct gcc tta ggg tct gtg gcc ggc cag tgc ctt tgt aaa gag<br>Ser Asp Pro Ala Leu Gly Ser Val Ala Gly Gln Cys Leu Cys Lys Glu<br>                 415               420               425 | 1361 |
| aac gtg gaa gga gcc aaa tgc gac cag tgc aaa ccc aac cac tac gga<br>Asn Val Glu Gly Ala Lys Cys Asp Gln Cys Lys Pro Asn His Tyr Gly<br>          430               435               440 | 1409 |
| cta agc gcc acc gac ccc ctg ggc tgc cag ccc tgc gac tgt aac ccc<br>Leu Ser Ala Thr Asp Pro Leu Gly Cys Gln Pro Cys Asp Cys Asn Pro<br>445               450               455 | 1457 |
| ctt ggg agt ctg cca ttc ttg acc tgt gat gtg gat aca ggc caa tgc<br>Leu Gly Ser Leu Pro Phe Leu Thr Cys Asp Val Asp Thr Gly Gln Cys<br>460               465               470               475 | 1505 |
| ttg tgc ctg tca tat gtc acc gga gca cac tgc gaa gaa tgc act gtt<br>Leu Cys Leu Ser Tyr Val Thr Gly Ala His Cys Glu Glu Cys Thr Val<br>                        480               485               490 | 1553 |
| gga tac tgg ggc ctg gga aat cat ctc cat ggg tgt tct ccc tgt gac<br>Gly Tyr Trp Gly Leu Gly Asn His Leu His Gly Cys Ser Pro Cys Asp<br>               495               500               505 | 1601 |
| tgt gat att gga ggt gct tat tct aac gtg tgc tca ccc aag aat ggg<br>Cys Asp Ile Gly Gly Ala Tyr Ser Asn Val Cys Ser Pro Lys Asn Gly<br>          510               515               520 | 1649 |
| cag tgt gaa tgc cgc cca cat gtc act ggc cgt agc tgc tct gaa cca<br>Gln Cys Glu Cys Arg Pro His Val Thr Gly Arg Ser Cys Ser Glu Pro<br>525               530               535 | 1697 |
| gcc cct ggc tac ttc ttt gct cct ttg aat ttc tat ctc tac gag gca<br>Ala Pro Gly Tyr Phe Phe Ala Pro Leu Asn Phe Tyr Leu Tyr Glu Ala<br>540               545               550               555 | 1745 |
| gag gaa gcc aca aca ctc caa gga ctg gcg cct ttg ggc tcg gag acg<br>Glu Glu Ala Thr Thr Leu Gln Gly Leu Ala Pro Leu Gly Ser Glu Thr<br>                        560               565               570 | 1793 |
| ttt ggc cag agt cct gct gtt cac gtt gtt tta gga gag cca gtt cct<br>Phe Gly Gln Ser Pro Ala Val His Val Val Leu Gly Glu Pro Val Pro<br>               575               580               585 | 1841 |
| ggg aac cct gtt aca tgg act gga cct gga ttt gcc agg gtt ctc cct<br>Gly Asn Pro Val Thr Trp Thr Gly Pro Gly Phe Ala Arg Val Leu Pro<br>          590               595               600 | 1889 |
| ggg gct ggc ttg aga ttt gct gtc aac aac att ccc ttt cct gtg gac<br>Gly Ala Gly Leu Arg Phe Ala Val Asn Asn Ile Pro Phe Pro Val Asp<br>605               610               615 | 1937 |
| ttc acc att gcc att cac tat gaa acc cag tct gca gct gac tgg act<br>Phe Thr Ile Ala Ile His Tyr Glu Thr Gln Ser Ala Ala Asp Trp Thr<br>620               625               630               635 | 1985 |
| gtc cag att gtg gtg aac ccc cct gga ggg agt gag cac tgc ata ccc<br>Val Gln Ile Val Val Asn Pro Pro Gly Gly Ser Glu His Cys Ile Pro<br>                        640               645               650 | 2033 |
| aag act cta cag tca aag cct cag tct ttt gcc tta cca gcg gct acg<br>Lys Thr Leu Gln Ser Lys Pro Gln Ser Phe Ala Leu Pro Ala Ala Thr<br>               655               660               665 | 2081 |
| aga atc atg ctg ctt ccc aca ccc atc tgt tta gaa cca gat gta caa | 2129 |

-continued

```
Arg Ile Met Leu Leu Pro Thr Pro Ile Cys Leu Glu Pro Asp Val Gln
            670             675             680 tat tcc ata gat gtc tat ttt tct cag cct ttg caa gga gag tcc cac    2177
Tyr Ser Ile Asp Val Tyr Phe Ser Gln Pro Leu Gln Gly Glu Ser His
685             690             695 gct cat tca cat gtc ctg gtg gac tct ctt ggc ctt att ccc caa atc    2225
Ala His Ser His Val Leu Val Asp Ser Leu Gly Leu Ile Pro Gln Ile
700             705             710             715 aat tca ttg gag aat ttc tgc agc aag cag gac tta gat gag tat cag    2273
Asn Ser Leu Glu Asn Phe Cys Ser Lys Gln Asp Leu Asp Glu Tyr Gln
                720             725             730 ctt cac aac tgt gtt gaa att gcc tca gca atg gga cct caa gtg ctc    2321
Leu His Asn Cys Val Glu Ile Ala Ser Ala Met Gly Pro Gln Val Leu
            735             740             745 ccg ggt gcc tgt gaa agg ctg atc atc agc atg tct gcc aag ctg cat    2369
Pro Gly Ala Cys Glu Arg Leu Ile Ile Ser Met Ser Ala Lys Leu His
        750             755             760 gat ggg gct gtg gcc tgc aag tgt cac ccc cag ggc tca gtc gga tcc    2417
Asp Gly Ala Val Ala Cys Lys Cys His Pro Gln Gly Ser Val Gly Ser
765             770             775 agc tgc agc cga ctt gga ggc cag tgc cag tgt aaa cct ctt gtg gtc    2465
Ser Cys Ser Arg Leu Gly Gly Gln Cys Gln Cys Lys Pro Leu Val Val
780             785             790             795 ggg cgc tgc tgt gac agg tgc tca act gga agc tat gat ttg ggg cat    2513
Gly Arg Cys Cys Asp Arg Cys Ser Thr Gly Ser Tyr Asp Leu Gly His
                800             805             810 cac ggc tgt cac cca tgt cac tgc cat cct caa gga tca aag gac act    2561
His Gly Cys His Pro Cys His Cys His Pro Gln Gly Ser Lys Asp Thr
            815             820             825 gta tgt gac caa gta aca gga cag tgc ccc tgc cat gga gag gtg tct    2609
Val Cys Asp Gln Val Thr Gly Gln Cys Pro Cys His Gly Glu Val Ser
        830             835             840 ggc cgc cgc tgt gat cgc tgc ctg gca ggc tac ttt gga ttt ccc agc    2657
Gly Arg Arg Cys Asp Arg Cys Leu Ala Gly Tyr Phe Gly Phe Pro Ser
845             850             855 tgc cac cct tgc cct tgt aat agg ttt gct gaa ctt tgt gat cct gag    2705
Cys His Pro Cys Pro Cys Asn Arg Phe Ala Glu Leu Cys Asp Pro Glu
860             865             870             875 aca ggg tca tgc ttc aat tgt gga ggc ttt aca act ggc aga aac tgt    2753
Thr Gly Ser Cys Phe Asn Cys Gly Gly Phe Thr Thr Gly Arg Asn Cys
                880             885             890 gaa agg tgt att gat ggt tac tat gga aat cct tct tca gga cag ccc    2801
Glu Arg Cys Ile Asp Gly Tyr Tyr Gly Asn Pro Ser Ser Gly Gln Pro
            895             900             905 tgt cgt cct tgc ctg tgt cca gat gat ccc tca agc aat cag tat ttt    2849
Cys Arg Pro Cys Leu Cys Pro Asp Asp Pro Ser Ser Asn Gln Tyr Phe
        910             915             920 gcc cat tcc tgt tat cag aat ctg tgg agc tca gat gta atc tgc aat    2897
Ala His Ser Cys Tyr Gln Asn Leu Trp Ser Ser Asp Val Ile Cys Asn
925             930             935 tgt ctt caa ggt tat acg ggt act cag tgt gga gaa tgc tct act ggt    2945
Cys Leu Gln Gly Tyr Thr Gly Thr Gln Cys Gly Glu Cys Ser Thr Gly
940             945             950             955 ttc tat gga aat cca aga att tca gga gca cct tgc caa cca tgt gcc    2993
Phe Tyr Gly Asn Pro Arg Ile Ser Gly Ala Pro Cys Gln Pro Cys Ala
                960             965             970 tgc aac aac aac ata gat gta acc gat cca gag tcc tgc agc cgg gta    3041
Cys Asn Asn Asn Ile Asp Val Thr Asp Pro Glu Ser Cys Ser Arg Val
            975             980             985
```

```
aca ggg gag tgc ctt cga tgt ttg cac aac act cag ggc gca aac tgc      3089
Thr Gly Glu Cys Leu Arg Cys Leu His Asn Thr Gln Gly Ala Asn Cys
        990                 995                 1000 cag ctc tgc aaa cca ggt cac tat gga tca gcc ctc aat cag acc tgc      3137
Gln Leu Cys Lys Pro Gly His Tyr Gly Ser Ala Leu Asn Gln Thr Cys
    1005                1010                1015 aga aga tgc tcc tgc cat gct tcc ggc gtg agt ccc atg gag tgt ccc      3185
Arg Arg Cys Ser Cys His Ala Ser Gly Val Ser Pro Met Glu Cys Pro
1020                1025                1030                1035 cct ggt ggg gga gct tgc ctc tgt gac cct gtc act ggt gca tgt cct      3233
Pro Gly Gly Gly Ala Cys Leu Cys Asp Pro Val Thr Gly Ala Cys Pro
                1040                1045                1050 tgt ctg ccg aat gtc aca ggc ctg gcc tgt gac cgt tgt gct gat gga      3281
Cys Leu Pro Asn Val Thr Gly Leu Ala Cys Asp Arg Cys Ala Asp Gly
            1055                1060                1065 tac tgg aat ctg gtc cct ggc aga gga tgt cag tca tgt gac tgt gac      3329
Tyr Trp Asn Leu Val Pro Gly Arg Gly Cys Gln Ser Cys Asp Cys Asp
        1070                1075                1080 cct agg acc tct caa agt agc cac tgt gac cag ctt aca ggc cag tgt      3377
Pro Arg Thr Ser Gln Ser Ser His Cys Asp Gln Leu Thr Gly Gln Cys
    1085                1090                1095 ccg tgt aaa tta ggt tac ggc ggg aaa cgt tgc agt gag tgc cag gaa      3425
Pro Cys Lys Leu Gly Tyr Gly Gly Lys Arg Cys Ser Glu Cys Gln Glu
1100                1105                1110                1115 aat tat tat ggt gat cca cct ggg cga tgc att cca tgt gat tgt aac      3473
Asn Tyr Tyr Gly Asp Pro Pro Gly Arg Cys Ile Pro Cys Asp Cys Asn
                1120                1125                1130 agg gca ggt acc cag aag ccc atc tgt gat cca gac aca ggc atg tgc      3521
Arg Ala Gly Thr Gln Lys Pro Ile Cys Asp Pro Asp Thr Gly Met Cys
            1135                1140                1145 cgc tgc cgg gag ggt gtc agc ggc cag aga tgt gat cgc tgt gcc cgg      3569
Arg Cys Arg Glu Gly Val Ser Gly Gln Arg Cys Asp Arg Cys Ala Arg
        1150                1155                1160 gga cac agc cag gaa ttc cct act tgt ctt caa tgt cac ttg tgc ttt      3617
Gly His Ser Gln Glu Phe Pro Thr Cys Leu Gln Cys His Leu Cys Phe
    1165                1170                1175 gat caa tgg gac cac acc att tct tcc ctc tcc aaa gcg gtg caa ggg      3665
Asp Gln Trp Asp His Thr Ile Ser Ser Leu Ser Lys Ala Val Gln Gly
1180                1185                1190                1195 tta atg aga ctg gct gct aac atg gaa gat aaa aga gag acc ctg cct      3713
Leu Met Arg Leu Ala Ala Asn Met Glu Asp Lys Arg Glu Thr Leu Pro
                1200                1205                1210 gtc tgt gag gca gac ttc aaa gac ctc aga ggg aac gtg tct gaa ata      3761
Val Cys Glu Ala Asp Phe Lys Asp Leu Arg Gly Asn Val Ser Glu Ile
            1215                1220                1225 gaa agg att ttg aaa cat cct gtt ttc cca tct ggg aaa ttc tta aaa      3809
Glu Arg Ile Leu Lys His Pro Val Phe Pro Ser Gly Lys Phe Leu Lys
        1230                1235                1240 gtc aag gat tat cat gac tct gtt aga aga caa atc atg cag cta aat      3857
Val Lys Asp Tyr His Asp Ser Val Arg Arg Gln Ile Met Gln Leu Asn
    1245                1250                1255 gaa caa ctg aaa gca gtg tat gaa ttt caa gat ctg aaa gat aca ata      3905
Glu Gln Leu Lys Ala Val Tyr Glu Phe Gln Asp Leu Lys Asp Thr Ile
1260                1265                1270                1275 gaa aga gca aag aat gaa gca gac ctc tta ctt gaa gac ctt cag gaa      3953
Glu Arg Ala Lys Asn Glu Ala Asp Leu Leu Leu Glu Asp Leu Gln Glu
                1280                1285                1290 gaa att gat ttg caa tcc agt gtc ctt aat gca agc att gcg gac tcc      4001
Glu Ile Asp Leu Gln Ser Ser Val Leu Asn Ala Ser Ile Ala Asp Ser
            1295                1300                1305
```

-continued

```
tca gaa aac atc aag aaa tat tat cac ata tca tca tct gct gaa aag    4049
Ser Glu Asn Ile Lys Lys Tyr Tyr His Ile Ser Ser Ser Ala Glu Lys
        1310            1315                1320 aaa att aat gaa act agt tcc acc att aat acc tct gca aat aca agg    4097
Lys Ile Asn Glu Thr Ser Ser Thr Ile Asn Thr Ser Ala Asn Thr Arg
1325                1330                1335 aat gac tta ctt acc atc tta gat aca cta acc tca aaa gga aac ttg    4145
Asn Asp Leu Leu Thr Ile Leu Asp Thr Leu Thr Ser Lys Gly Asn Leu
    1340                1345                1350            1355 tca ttg gaa aga tta aag cag att aag ata cca gat atc caa ata ttg    4193
Ser Leu Glu Arg Leu Lys Gln Ile Lys Ile Pro Asp Ile Gln Ile Leu
                1360                1365                1370 aat gaa aag gtg tgc gga gat cca gga aat gtg cca tgt gtg ccc ttg    4241
Asn Glu Lys Val Cys Gly Asp Pro Gly Asn Val Pro Cys Val Pro Leu
            1375                1380                1385 ccc tgt ggc ggt gct ctc tgc acg ggc cgg aag ggg cac agg aag tgt    4289
Pro Cys Gly Gly Ala Leu Cys Thr Gly Arg Lys Gly His Arg Lys Cys
        1390                1395                1400 agg ggt ccc ggc tgt cac ggc tcc ctg acc ctc tca acg aat gcc ctc    4337
Arg Gly Pro Gly Cys His Gly Ser Leu Thr Leu Ser Thr Asn Ala Leu
    1405                1410                1415 caa aaa gcc cag gaa gca aaa tcc att att cgt aat ttg gac aaa cag    4385
Gln Lys Ala Gln Glu Ala Lys Ser Ile Ile Arg Asn Leu Asp Lys Gln
1420                1425                1430                1435 gtt cgt ggg ttg aaa aat cag atc gaa agt ata agt gaa cag gca gaa    4433
Val Arg Gly Leu Lys Asn Gln Ile Glu Ser Ile Ser Glu Gln Ala Glu
            1440                1445                1450 gtc tcc aaa aac aat gcc tta cag ctg agg gaa aaa ctg gga aat ata    4481
Val Ser Lys Asn Asn Ala Leu Gln Leu Arg Glu Lys Leu Gly Asn Ile
        1455                1460                1465 aga aac caa agt gac tct gaa gaa gaa aac atc aat ctt ttc atc aaa    4529
Arg Asn Gln Ser Asp Ser Glu Glu Glu Asn Ile Asn Leu Phe Ile Lys
    1470                1475                1480 aaa gtg aaa aac ttt ttg tta gag gaa aac gtg cct cca gaa gac atc    4577
Lys Val Lys Asn Phe Leu Leu Glu Glu Asn Val Pro Pro Glu Asp Ile
1485                1490                1495 gag aag gtt gcg aat ggt gtg ctt gac att cac cta cca att cca tcc    4625
Glu Lys Val Ala Asn Gly Val Leu Asp Ile His Leu Pro Ile Pro Ser
1500                1505                1510                1515 caa aat cta acc gat gaa ctt gtc aaa ata cag aaa cat atg caa ctc    4673
Gln Asn Leu Thr Asp Glu Leu Val Lys Ile Gln Lys His Met Gln Leu
            1520                1525                1530 tgt gag gat tac agg aca gat gaa aac agg tca aat gaa gaa gca gat    4721
Cys Glu Asp Tyr Arg Thr Asp Glu Asn Arg Ser Asn Glu Glu Ala Asp
        1535                1540                1545 gga gcc caa aag ctt ttg gtg aag gcc aaa gca gct gag aaa gca gca    4769
Gly Ala Gln Lys Leu Leu Val Lys Ala Lys Ala Ala Glu Lys Ala Ala
    1550                1555                1560 aat att cta tta aat ctt gac aaa aca ttg aac cag tta caa caa gct    4817
Asn Ile Leu Leu Asn Leu Asp Lys Thr Leu Asn Gln Leu Gln Gln Ala
1565                1570                1575 caa atc act caa gga cgg gca aac tct acc att aca cag ctg act gcc    4865
Gln Ile Thr Gln Gly Arg Ala Asn Ser Thr Ile Thr Gln Leu Thr Ala
1580                1585                1590                1595 aat ata aca aaa ata aaa aag aat gtg ctg cag gct gaa aat caa acc    4913
Asn Ile Thr Lys Ile Lys Lys Asn Val Leu Gln Ala Glu Asn Gln Thr
            1600                1605                1610 agg gaa atg aag agt gag ctg gag tta gca aag cag cga tca ggg ctg    4961
Arg Glu Met Lys Ser Glu Leu Glu Leu Ala Lys Gln Arg Ser Gly Leu
```

-continued

```
                 1615            1620            1625
gag gat gga ctt tcc ctg ctg cag acc aag ttg caa agg cat caa gac      5009
Glu Asp Gly Leu Ser Leu Leu Gln Thr Lys Leu Gln Arg His Gln Asp
        1630            1635            1640 cac gct gtc aat gcg aaa gtt cag gct gaa tct gcc caa cac cag gct      5057
His Ala Val Asn Ala Lys Val Gln Ala Glu Ser Ala Gln His Gln Ala
    1645            1650            1655 ggg agt ctt gag aag gaa ttt gtt gag ctg aaa aaa caa tat gct att      5105
Gly Ser Leu Glu Lys Glu Phe Val Glu Leu Lys Lys Gln Tyr Ala Ile
1660            1665            1670            1675 ctc caa cgt aag aca agc act aca gga cta aca aag gag aca tta gga      5153
Leu Gln Arg Lys Thr Ser Thr Thr Gly Leu Thr Lys Glu Thr Leu Gly
            1680            1685            1690 aaa gtt aaa cag cta aaa gat gcg gca gaa aaa ttg gct gga gat aca      5201
Lys Val Lys Gln Leu Lys Asp Ala Ala Glu Lys Leu Ala Gly Asp Thr
        1695            1700            1705 gag gcc aag ata aga aga ata aca gat tta gaa agg aaa atc caa gat      5249
Glu Ala Lys Ile Arg Arg Ile Thr Asp Leu Glu Arg Lys Ile Gln Asp
    1710            1715            1720 ttg aat cta agt aga caa gca aaa gct gat caa ctg aga ata ttg gaa      5297
Leu Asn Leu Ser Arg Gln Ala Lys Ala Asp Gln Leu Arg Ile Leu Glu
    1725            1730            1735 gat caa gtt gtt gcc att aaa aat gaa att gtt gaa caa gaa aaa aaa      5345
Asp Gln Val Val Ala Ile Lys Asn Glu Ile Val Glu Gln Glu Lys Lys
1740            1745            1750            1755 tat gct agg tgc tat agc taggcagagt taaagagcaa aagcttgtgc             5393
Tyr Ala Arg Cys Tyr Ser
                1760 ctttgtttct ggtttctgat gtacaagccc ctggggctct gttgaacctg tgaaatactg    5453 acaatgtctt ctaccttcct tccccacacc ctgtccttat tagacacctg ctcagtgtgg    5513 ctggaggttg aaatgccacc aggaaaatgc cacttcataa ttgaaggggg aaagtaatga    5573 aattgtctct ggtttcagaa acttttcctc ttaccttcct ttctctttcc taacttaaaa    5633 ataacagttt ccatataaca agtagaaatt taagtaagta ctctactaac taataatcat    5693 ttcagtcaga taaacctaaa cattaaataa atatctccaa tattaggatg gaatacatat    5753 gtatggcatg tactagattg tcctatattt tatgtttatt tggatttgct tttatttgta    5813 aaattattct tttctgaata aactgcatac aattcaaaat ggaaaaaaaa aaaaaaaaa     5873 a                                                                    5874
```

<210> SEQ ID NO 3
<211> LENGTH: 1587
<212> TYPE: PRT
<213> ORGANISM: Homo sapiens

<400> SEQUENCE: 3

```
Met Ala Ala Ala Ala Leu Leu Leu Gly Leu Ala Leu Leu Ala Pro Arg
 1               5                  10                  15

Ala Ala Gly Ala Gly Met Gly Ala Cys Tyr Asp Gly Ala Gly Arg Pro
             20                  25                  30

Gln Arg Cys Leu Pro Val Phe Glu Asn Ala Ala Phe Gly Arg Leu Ala
         35                  40                  45

Gln Ala Ser His Thr Cys Gly Ser Pro Pro Glu Asp Phe Cys Pro His
     50                  55                  60

Val Gly Ala Ala Gly Ala Gly Ala His Cys Gln Arg Cys Asp Ala Ala
 65                  70                  75                  80
```

-continued

```
Asp Pro Gln Arg His His Asn Ala Ser Tyr Leu Thr Asp Phe His Ser
                85                  90                  95

Gln Asp Glu Ser Thr Trp Trp Gln Ser Pro Ser Met Ala Phe Gly Val
            100                 105                 110

Gln Tyr Pro Thr Ser Val Asn Ile Thr Leu Arg Leu Gly Lys Ala Tyr
        115                 120                 125

Glu Ile Thr Tyr Val Arg Leu Lys Phe His Thr Ser Arg Pro Glu Ser
    130                 135                 140

Phe Ala Ile Tyr Lys Arg Ser Arg Ala Asp Gly Pro Trp Glu Pro Tyr
145                 150                 155                 160

Gln Phe Tyr Ser Ala Ser Cys Gln Lys Thr Tyr Gly Arg Pro Glu Gly
                165                 170                 175

Gln Tyr Leu Arg Pro Gly Glu Asp Glu Arg Val Ala Phe Cys Thr Ser
            180                 185                 190

Glu Phe Ser Asp Ile Ser Pro Leu Ser Gly Gly Asn Val Ala Phe Ser
        195                 200                 205

Thr Leu Glu Gly Arg Pro Ser Ala Tyr Asn Phe Glu Glu Ser Pro Gly
    210                 215                 220

Leu Gln Glu Trp Val Thr Ser Thr Glu Leu Leu Ile Ser Leu Asp Arg
225                 230                 235                 240

Leu Asn Thr Phe Gly Asp Asp Ile Phe Lys Asp Pro Lys Val Leu Gln
                245                 250                 255

Ser Tyr Tyr Tyr Ala Val Ser Asp Phe Ser Val Gly Gly Arg Cys Lys
            260                 265                 270

Cys Asn Gly His Ala Ser Glu Cys Gly Pro Asp Val Ala Gly Gln Leu
        275                 280                 285

Ala Cys Arg Cys Gln His Asn Thr Gly Thr Asp Cys Glu Arg Cys
    290                 295                 300

Leu Pro Phe Phe Gln Asp Arg Pro Trp Ala Arg Gly Thr Ala Glu Ala
305                 310                 315                 320

Ala His Glu Cys Leu Pro Cys Asn Cys Ser Gly Arg Ser Glu Glu Cys
                325                 330                 335

Thr Phe Asp Arg Glu Leu Phe Arg Ser Thr Gly His Gly Gly Arg Cys
            340                 345                 350

His His Cys Arg Asp His Thr Ala Gly Pro His Cys Glu Arg Cys Gln
        355                 360                 365

Glu Asn Phe Tyr His Trp Asp Pro Arg Met Pro Cys Gln Pro Cys Asp
    370                 375                 380

Cys Gln Ser Ala Gly Ser Leu His Leu Gln Cys Asp Asp Thr Gly Thr
385                 390                 395                 400

Cys Ala Cys Lys Pro Thr Val Thr Gly Trp Lys Cys Asp Arg Cys Leu
                405                 410                 415

Pro Gly Phe His Ser Leu Ser Glu Gly Gly Cys Arg Pro Cys Thr Cys
            420                 425                 430

Asn Pro Ala Gly Ser Leu Asp Thr Cys Asp Pro Arg Ser Gly Arg Cys
        435                 440                 445

Pro Cys Lys Glu Asn Val Glu Gly Asn Leu Cys Asp Arg Cys Arg Pro
    450                 455                 460

Gly Thr Phe Asn Leu Gln Pro His Asn Pro Ala Gly Cys Ser Ser Cys
465                 470                 475                 480

Phe Cys Tyr Gly His Ser Lys Val Cys Ala Ser Thr Ala Gln Phe Gln
                485                 490                 495

Val His His Ile Leu Ser Asp Phe His Gln Gly Ala Glu Gly Trp Trp
```

-continued

```
            500                 505                 510
Ala Arg Ser Val Gly Gly Ser Glu His Ser Pro Gln Trp Ser Pro Asn
            515                 520                 525
Gly Val Leu Leu Ser Pro Glu Asp Glu Glu Leu Thr Ala Pro Gly
            530                 535             540
Lys Phe Leu Gly Asp Gln Arg Phe Ser Tyr Gly Gln Pro Leu Ile Leu
545                 550                 555                 560
Thr Phe Arg Val Pro Pro Gly Asp Ser Pro Leu Pro Val Gln Leu Arg
                    565                 570                 575
Leu Glu Gly Thr Gly Leu Ala Leu Ser Leu Arg His Ser Ser Leu Ser
                580                 585                 590
Gly Pro Gln Asp Ala Arg Ala Ser Gln Gly Gly Arg Ala Gln Val Pro
            595                 600                 605
Leu Gln Glu Thr Ser Glu Asp Val Ala Pro Leu Pro Pro Phe His
            610                 615                 620
Phe Gln Arg Leu Leu Ala Asn Leu Thr Ser Leu Arg Leu Arg Val Ser
625                 630                 635                 640
Pro Gly Pro Ser Pro Ala Gly Pro Val Phe Leu Thr Glu Val Arg Leu
                    645                 650                 655
Thr Ser Ala Arg Pro Gly Leu Ser Pro Pro Ala Ser Trp Val Glu Ile
                660                 665                 670
Cys Ser Cys Pro Thr Gly Tyr Thr Gly Gln Phe Cys Glu Ser Cys Ala
                675                 680                 685
Pro Gly Tyr Lys Arg Glu Met Pro Gln Gly Gly Pro Tyr Ala Ser Cys
            690                 695                 700
Val Pro Cys Thr Cys Asn Gln His Gly Thr Cys Asp Pro Asn Thr Gly
705                 710                 715                 720
Ile Cys Val Cys Ser His His Thr Glu Gly Pro Ser Cys Glu Arg Cys
                    725                 730                 735
Leu Pro Gly Phe Tyr Gly Asn Pro Phe Ala Gly Gln Ala Asp Asp Cys
                740                 745                 750
Gln Pro Cys Pro Cys Pro Gly Gln Ser Ala Cys Thr Thr Ile Pro Glu
            755                 760                 765
Ser Gly Glu Val Val Cys Thr His Cys Pro Pro Gly Gln Arg Gly Arg
            770                 775                 780
Arg Cys Glu Val Cys Asp Asp Gly Phe Phe Gly Asp Pro Leu Gly Leu
785                 790                 795                 800
Phe Gly His Pro Gln Pro Cys His Gln Cys Gln Cys Ser Gly Asn Val
                    805                 810                 815
Asp Pro Asn Ala Val Gly Asn Cys Asp Pro Leu Ser Gly His Cys Leu
                820                 825                 830
Arg Cys Leu His Asn Thr Thr Gly Asp His Cys Glu His Cys Gln Glu
                835                 840                 845
Gly Phe Tyr Gly Ser Ala Leu Ala Pro Arg Pro Ala Asp Lys Cys Met
            850                 855                 860
Pro Cys Ser Cys His Pro Gln Gly Ser Val Ser Glu Gln Met Pro Cys
865                 870                 875                 880
Asp Pro Val Thr Gly Gln Cys Ser Cys Leu Pro His Val Thr Ala Arg
                    885                 890                 895
Asp Cys Ser Arg Cys Tyr Pro Gly Phe Phe Asp Leu Gln Pro Gly Arg
                900                 905                 910
Gly Cys Arg Ser Cys Lys Cys His Pro Leu Gly Ser Gln Glu Asp Gln
            915                 920                 925
```

-continued

```
Cys His Pro Lys Thr Gly Gln Cys Thr Cys Arg Pro Gly Val Thr Gly
    930                 935                 940
Gln Ala Cys Asp Arg Cys Gln Leu Gly Phe Phe Gly Ser Ser Ile Lys
945                 950                 955                 960
Gly Cys Arg Ala Cys Arg Cys Ser Pro Leu Gly Ala Ala Ser Ala Gln
                965                 970                 975
Cys His Tyr Asn Gly Thr Cys Val Cys Arg Pro Gly Phe Glu Gly Tyr
            980                 985                 990
Lys Cys Asp Arg Cys His Tyr Asn Phe Phe Leu Thr Ala Asp Gly Thr
        995                 1000                1005
His Cys Gln Gln Cys Pro Ser Cys Tyr Ala Leu Val Lys Glu Glu Thr
    1010                1015                1020
Ala Lys Leu Lys Ala Arg Leu Thr Leu Thr Glu Gly Trp Leu Gln Gly
1025                1030                1035                1040
Ser Asp Cys Gly Ser Pro Trp Gly Pro Leu Asp Ile Leu Leu Gly Glu
                1045                1050                1055
Ala Pro Arg Gly Asp Val Tyr Gln Gly His His Leu Leu Pro Gly Ala
                1060                1065                1070
Arg Glu Ala Phe Leu Glu Gln Met Met Gly Leu Glu Gly Ala Val Lys
                1075                1080                1085
Ala Ala Arg Glu Gln Leu Gln Arg Leu Asn Lys Gly Ala Arg Cys Ala
    1090                1095                1100
Gln Ala Gly Ser Gln Lys Thr Cys Thr Gln Leu Ala Asp Leu Glu Ala
1105                1110                1115                1120
Val Leu Glu Ser Ser Glu Glu Ile Leu His Ala Ala Ala Ile Leu
                1125                1130                1135
Ala Ser Leu Glu Ile Pro Gln Glu Gly Pro Ser Gln Pro Thr Lys Trp
    1140                1145                1150
Ser His Leu Ala Ile Glu Ala Arg Ala Leu Ala Arg Ser His Arg Asp
        1155                1160                1165
Thr Ala Thr Lys Ile Ala Ala Thr Ala Trp Arg Ala Leu Leu Ala Ser
    1170                1175                1180
Asn Thr Ser Tyr Ala Leu Leu Trp Asn Leu Leu Glu Gly Arg Val Ala
1185                1190                1195                1200
Leu Glu Thr Gln Arg Asp Leu Glu Asp Arg Tyr Gln Glu Val Gln Ala
                1205                1210                1215
Ala Gln Lys Ala Leu Arg Thr Ala Val Ala Glu Val Leu Pro Glu Ala
                1220                1225                1230
Glu Ser Val Leu Ala Thr Val Gln Gln Val Gly Ala Asp Thr Ala Pro
    1235                1240                1245
Tyr Leu Ala Leu Leu Ala Ser Pro Gly Ala Leu Pro Gln Lys Ser Arg
    1250                1255                1260
Ala Glu Asp Leu Gly Leu Lys Ala Lys Ala Leu Glu Lys Thr Val Ala
1265                1270                1275                1280
Ser Trp Gln His Met Ala Thr Glu Ala Ala Arg Thr Leu Gln Thr Ala
                1285                1290                1295
Ala Gln Ala Thr Leu Arg Gln Thr Glu Pro Leu Thr Met Ala Arg Ser
                1300                1305                1310
Arg Leu Thr Ala Thr Phe Ala Ser Gln Leu His Gln Gly Ala Arg Ala
                1315                1320                1325
Ala Leu Thr Gln Ala Ser Ser Val Gln Ala Ala Thr Val Thr Val
                1330                1335                1340
```

-continued

```
Met Gly Ala Arg Thr Leu Leu Ala Asp Leu Glu Gly Met Lys Leu Gln
1345                1350                1355                1360

Phe Pro Arg Pro Lys Asp Gln Ala Ala Leu Gln Arg Lys Ala Asp Ser
            1365                1370                1375

Val Ser Asp Arg Leu Leu Ala Asp Thr Arg Lys Thr Lys Gln Ala
        1380                1385                1390

Glu Arg Met Leu Gly Asn Ala Ala Pro Leu Ser Ser Ala Lys Lys
    1395                1400                1405

Lys Gly Arg Glu Ala Glu Val Leu Ala Lys Asp Ser Ala Lys Leu Ala
1410                1415                1420

Lys Ala Leu Leu Arg Glu Arg Lys Gln Ala His Arg Ala Ser Arg
1425                1430                1435                1440

Leu Thr Ser Gln Thr Gln Ala Thr Leu Gln Gln Ala Ser Gln Gln Val
                1445                1450                1455

Leu Ala Ser Glu Ala Arg Arg Gln Glu Leu Glu Glu Ala Glu Arg Val
            1460                1465                1470

Gly Ala Gly Leu Ser Glu Met Glu Gln Gln Ile Arg Glu Ser Arg Ile
        1475                1480                1485

Ser Leu Glu Lys Asp Ile Glu Thr Leu Ser Glu Leu Leu Ala Arg Leu
    1490                1495                1500

Gly Ser Leu Asp Thr His Gln Ala Pro Ala Gln Ala Leu Asn Glu Thr
1505                1510                1515                1520

Gln Trp Ala Leu Glu Arg Leu Arg Leu Gln Leu Gly Ser Pro Gly Ser
                1525                1530                1535

Leu Gln Arg Lys Leu Ser Leu Leu Glu Gln Glu Ser Gln Gln Gln Glu
            1540                1545                1550

Leu Gln Ile Gln Gly Phe Glu Ser Asp Leu Ala Glu Ile Arg Ala Asp
        1555                1560                1565

Lys Gln Asn Leu Glu Ala Ile Leu His Ser Leu Pro Glu Asn Cys Ala
    1570                1575                1580

Ser Trp Gln
1585

<210> SEQ ID NO 4
<211> LENGTH: 5184
<212> TYPE: DNA
<213> ORGANISM: Homo sapiens
<220> FEATURE:
<221> NAME/KEY: CDS
<222> LOCATION: (98)...(4858)

<400> SEQUENCE: 4
ccccgcaggg gaaggcgggt cctggcggcc agcgcgcggt ccgcgcccac cctagccgac      60
ggggccggca gagcgcgcgg cgtcggtgcc cttgacc atg gcg gcg gct gcg ctt     115
                                        Met Ala Ala Ala Ala Leu
                                         1               5 ctg ctg ggg ctg gcg ctg ctg gca ccg cgg gcg gcc ggc gcg ggc atg     163
Leu Leu Gly Leu Ala Leu Leu Ala Pro Arg Ala Ala Gly Ala Gly Met
            10                  15                  20 ggc gcg tgc tat gac ggc gca ggg cgc ccg cag cgc tgc ctg ccg gtg     211
Gly Ala Cys Tyr Asp Gly Ala Gly Arg Pro Gln Arg Cys Leu Pro Val
        25                  30                  35 ttc gag aac gcg gcg ttt ggg cgg ctc gcc cag gcc tcg cac acg tgc     259
Phe Glu Asn Ala Ala Phe Gly Arg Leu Ala Gln Ala Ser His Thr Cys
    40                  45                  50 ggc agc ccg ccc gag gac ttc tgt ccc cac gtg ggc gcc gcg ggc gcg     307
Gly Ser Pro Pro Glu Asp Phe Cys Pro His Val Gly Ala Ala Gly Ala
```

-continued

```
                    55                      60                      65                      70
gggggctcattgccagcgctgcgacgccgccgacccccagcgccaccac              355
Gly Ala His Cys Gln Arg Cys Asp Ala Ala Asp Pro Gln Arg His His
                        75                      80                      85 aacgcctcctactcaccgacttccacagccaggacgagagcacctgg              403
Asn Ala Ser Tyr Leu Thr Asp Phe His Ser Gln Asp Glu Ser Thr Trp
                90                      95                      100 tggcagagcccgtccatggccttcggcgtgcagtaccccacctcggtc              451
Trp Gln Ser Pro Ser Met Ala Phe Gly Val Gln Tyr Pro Thr Ser Val
        105                     110                     115 aacatcaccctccgcctagggaaggcttatgagatcacgtatgtgagg              499
Asn Ile Thr Leu Arg Leu Gly Lys Ala Tyr Glu Ile Thr Tyr Val Arg
    120                     125                     130 ctgaagttccacaccagtcgccctgagagctttgccatctacaagcgc              547
Leu Lys Phe His Thr Ser Arg Pro Glu Ser Phe Ala Ile Tyr Lys Arg
135                     140                     145                     150 agccgcgccgacggcccatgggagccctaccagttctacagcgcctcc              595
Ser Arg Ala Asp Gly Pro Trp Glu Pro Tyr Gln Phe Tyr Ser Ala Ser
                        155                     160                     165 tgccagaagacctacggccggcccgagggccagtacctgcgccccggc              643
Cys Gln Lys Thr Tyr Gly Arg Pro Glu Gly Gln Tyr Leu Arg Pro Gly
                170                     175                     180 gaggacgagcgcgtggccttctgcacctctgagttcagcgacatctcc              691
Glu Asp Glu Arg Val Ala Phe Cys Thr Ser Glu Phe Ser Asp Ile Ser
            185                     190                     195 ccgctgagtggcggcaacgtggccttctccaccctggagggccggccc              739
Pro Leu Ser Gly Gly Asn Val Ala Phe Ser Thr Leu Glu Gly Arg Pro
    200                     205                     210 agcgcctacaacttcgaggagagccctgggctgcaggagtggtcacc              787
Ser Ala Tyr Asn Phe Glu Glu Ser Pro Gly Leu Gln Glu Trp Val Thr
215                     220                     225                     230 agcaccgaactcctcatctctctagacggctcaacacgtttgggggac              835
Ser Thr Glu Leu Leu Ile Ser Leu Asp Arg Leu Asn Thr Phe Gly Asp
                        235                     240                     245 gacatcttcaaggaccccaaggtgctccagtcctactattatgccgtg              883
Asp Ile Phe Lys Asp Pro Lys Val Leu Gln Ser Tyr Tyr Tyr Ala Val
                250                     255                     260 tccgacttctctgtgggcggcaggtgcaagtgcaacgggcatgccagc              931
Ser Asp Phe Ser Val Gly Gly Arg Cys Lys Cys Asn Gly His Ala Ser
            265                     270                     275 gagtgcggccccgacgtggcaggccagttggcctgccggtgcagcac              979
Glu Cys Gly Pro Asp Val Ala Gly Gln Leu Ala Cys Arg Cys Gln His
    280                     285                     290 aacaccaccggcacagactgtgagcgctgcctgcccttcttccaggac              1027
Asn Thr Thr Gly Thr Asp Cys Glu Arg Cys Leu Pro Phe Phe Gln Asp
295                     300                     305                     310 cgcccgtgggccggggcaccgccgaggctgcccacgagtgtctgccc              1075
Arg Pro Trp Ala Arg Gly Thr Ala Glu Ala Ala His Glu Cys Leu Pro
                        315                     320                     325 tgcaactgcagtggccgctccgaggaatgcacgtttgatcgggagctc              1123
Cys Asn Cys Ser Gly Arg Ser Glu Glu Cys Thr Phe Asp Arg Glu Leu
                330                     335                     340 ttccgcagcacaggccacggggggcgctgtcaccactgccgtgaccac              1171
Phe Arg Ser Thr Gly His Gly Gly Arg Cys His His Cys Arg Asp His
            345                     350                     355 acagctgggccacactgtgagcgctgtcaggagaatttctatcactgg              1219
Thr Ala Gly Pro His Cys Glu Arg Cys Gln Glu Asn Phe Tyr His Trp
    360                     365                     370 gacccgcggatgccatgccagccctgtgactgcagtcggcaggctcc              1267
Asp Pro Arg Met Pro Cys Gln Pro Cys Asp Cys Gln Ser Ala Gly Ser
```

```
                                                            -continued

Asp Pro Arg Met Pro Cys Gln Pro Cys Asp Cys Gln Ser Ala Gly Ser
375                 380                 385                 390 cta cac ctc cag tgc gat gac aca ggc acc tgc gcc tgc aag ccc aca   1315
Leu His Leu Gln Cys Asp Asp Thr Gly Thr Cys Ala Cys Lys Pro Thr
                395                 400                 405 gtg act ggc tgg aag tgt gac cgc tgt ctg ccc ggg ttc cac tcg ctc   1363
Val Thr Gly Trp Lys Cys Asp Arg Cys Leu Pro Gly Phe His Ser Leu
            410                 415                 420 agt gag gga ggc tgc aga ccc tgc act tgc aat ccc gct ggc agc ctg   1411
Ser Glu Gly Gly Cys Arg Pro Cys Thr Cys Asn Pro Ala Gly Ser Leu
            425                 430                 435 gac acc tgt gac ccc cgc agt ggg cgc tgc ccc tgc aaa gag aat gtg   1459
Asp Thr Cys Asp Pro Arg Ser Gly Arg Cys Pro Cys Lys Glu Asn Val
        440                 445                 450 gaa ggc aac cta tgt gac aga tgt cgc ccg ggg acc ttt aac ctg cag   1507
Glu Gly Asn Leu Cys Asp Arg Cys Arg Pro Gly Thr Phe Asn Leu Gln
455                 460                 465                 470 ccc cac aat cca gct ggc tgc agc agc tgt ttc tgc tat ggc cac tcc   1555
Pro His Asn Pro Ala Gly Cys Ser Ser Cys Phe Cys Tyr Gly His Ser
                475                 480                 485 aag gtg tgc gcg tcc act gcc cag ttc cag gtg cat cac atc ctc agc   1603
Lys Val Cys Ala Ser Thr Ala Gln Phe Gln Val His His Ile Leu Ser
            490                 495                 500 gat ttc cac cag gga gcc gaa ggc tgg tgg gcc aga agt gtg ggg ggc   1651
Asp Phe His Gln Gly Ala Glu Gly Trp Trp Ala Arg Ser Val Gly Gly
            505                 510                 515 tct gag cac tcc cca caa tgg agc cca aat ggg gtc ctc ctg agc cca   1699
Ser Glu His Ser Pro Gln Trp Ser Pro Asn Gly Val Leu Leu Ser Pro
520                 525                 530 gaa gac gag gag gag ctc aca gca cca ggg aag ttc ctg gga gac cag   1747
Glu Asp Glu Glu Glu Leu Thr Ala Pro Gly Lys Phe Leu Gly Asp Gln
535                 540                 545                 550 cgg ttc agc tat ggg cag ccc ctc ata ctg acc ttc cgg gtg ccc ccc   1795
Arg Phe Ser Tyr Gly Gln Pro Leu Ile Leu Thr Phe Arg Val Pro Pro
                555                 560                 565 ggg gac tcc cca ctc cct gta cag ctg agg ctg gaa ggg aca ggc ttg   1843
Gly Asp Ser Pro Leu Pro Val Gln Leu Arg Leu Glu Gly Thr Gly Leu
            570                 575                 580 gcc ctg tcc ctg agg cac tct agc ctg tct ggc ccc cag gat gcc agg   1891
Ala Leu Ser Leu Arg His Ser Ser Leu Ser Gly Pro Gln Asp Ala Arg
            585                 590                 595 gca tcc cag gga ggt aga gct cag gtt cca ctg cag gag acc tcc gag   1939
Ala Ser Gln Gly Gly Arg Ala Gln Val Pro Leu Gln Glu Thr Ser Glu
        600                 605                 610 gac gtg gcc cct cca ctg ccc ccc ttc cac ttc cag cgg ctc ctc gcc   1987
Asp Val Ala Pro Pro Leu Pro Pro Phe His Phe Gln Arg Leu Leu Ala
615                 620                 625                 630 aac ctg acc agc ctc cgc ctc cgc gtc agt ccc ggc ccc agc cct gcc   2035
Asn Leu Thr Ser Leu Arg Leu Arg Val Ser Pro Gly Pro Ser Pro Ala
                635                 640                 645 ggt cca gtg ttc ctg act gag gtc cgg ctc aca tcc gcc cgg cca ggg   2083
Gly Pro Val Phe Leu Thr Glu Val Arg Leu Thr Ser Ala Arg Pro Gly
            650                 655                 660 ctt tcc ccg cca gcc tcc tgg gtg gag att tgt tca tgt ccc act ggc   2131
Leu Ser Pro Pro Ala Ser Trp Val Glu Ile Cys Ser Cys Pro Thr Gly
            665                 670                 675 tac acg ggc cag ttc tgt gaa tcc tgt gct ccg gga tac aag agg gag   2179
Tyr Thr Gly Gln Phe Cys Glu Ser Cys Ala Pro Gly Tyr Lys Arg Glu
        680                 685                 690
```

-continued

```
atg cca cag ggg ggt ccc tat gcc agc tgt gtc ccc tgc acc tgt aac       2227
Met Pro Gln Gly Gly Pro Tyr Ala Ser Cys Val Pro Cys Thr Cys Asn
695             700                 705                 710 cag cat ggc acc tgt gac ccc aac aca ggg atc tgt gtc tgc agc cac       2275
Gln His Gly Thr Cys Asp Pro Asn Thr Gly Ile Cys Val Cys Ser His
            715                 720                 725 cat acc gag ggc cca tcc tgt gaa cgc tgt ttg cca ggt ttc tat ggc       2323
His Thr Glu Gly Pro Ser Cys Glu Arg Cys Leu Pro Gly Phe Tyr Gly
        730                 735                 740 aac cct ttc gcg ggc caa gcc gac gac tgc cag ccc tgt ccc tgc cct       2371
Asn Pro Phe Ala Gly Gln Ala Asp Asp Cys Gln Pro Cys Pro Cys Pro
    745                 750                 755 ggc cag tcg gcc tgt acg acc atc cca gag agc ggg gag gtg gtg tgt       2419
Gly Gln Ser Ala Cys Thr Thr Ile Pro Glu Ser Gly Glu Val Val Cys
760                 765                 770 acc cac tgc ccc ccg ggc cag aga ggg cgg cgc tgt gag gtc tgt gat       2467
Thr His Cys Pro Pro Gly Gln Arg Gly Arg Arg Cys Glu Val Cys Asp
775                 780                 785                 790 gat ggc ttt ttt ggg gac ccg ctg ggg ctc ttt ggg cac ccc cag ccc       2515
Asp Gly Phe Phe Gly Asp Pro Leu Gly Leu Phe Gly His Pro Gln Pro
                795                 800                 805 tgc cac cag tgc cag tgt agc ggg aac gtg gac ccc aat gcc gtg ggc       2563
Cys His Gln Cys Gln Cys Ser Gly Asn Val Asp Pro Asn Ala Val Gly
            810                 815                 820 aac tgt gac ccc ctg tct ggc cac tgc ctg cgc tgc ctg cac aac acc       2611
Asn Cys Asp Pro Leu Ser Gly His Cys Leu Arg Cys Leu His Asn Thr
        825                 830                 835 acg ggt gac cac tgt gag cac tgt cag gaa ggc ttc tac ggg agc gcc       2659
Thr Gly Asp His Cys Glu His Cys Gln Glu Gly Phe Tyr Gly Ser Ala
    840                 845                 850 ctg gcc cct cga ccc gca gac aaa tgc atg cct tgc agc tgt cac cca       2707
Leu Ala Pro Arg Pro Ala Asp Lys Cys Met Pro Cys Ser Cys His Pro
855                 860                 865                 870 cag ggc tcg gtc agt gag cag atg ccc tgc gac cca gtg aca ggc caa       2755
Gln Gly Ser Val Ser Glu Gln Met Pro Cys Asp Pro Val Thr Gly Gln
                875                 880                 885 tgc tcc tgc ctg cct cat gtg act gca cgg gac tgc agc cgc tgc tac       2803
Cys Ser Cys Leu Pro His Val Thr Ala Arg Asp Cys Ser Arg Cys Tyr
            890                 895                 900 cct ggc ttc ttc gac ctc cag cct ggg agg ggc tgc cgg agc tgc aag       2851
Pro Gly Phe Phe Asp Leu Gln Pro Gly Arg Gly Cys Arg Ser Cys Lys
        905                 910                 915 tgt cac cca ctg ggc tcc cag gag gac cag tgc cat ccc aag act gga       2899
Cys His Pro Leu Gly Ser Gln Glu Asp Gln Cys His Pro Lys Thr Gly
    920                 925                 930 cag tgc acc tgc cgc cca ggt gtc aca ggc cag gcc tgt gac agg tgc       2947
Gln Cys Thr Cys Arg Pro Gly Val Thr Gly Gln Ala Cys Asp Arg Cys
935                 940                 945                 950 cag ctg ggt ttc ttc ggc tcc tca atc aag ggc tgc cgg gcc tgc agg       2995
Gln Leu Gly Phe Phe Gly Ser Ser Ile Lys Gly Cys Arg Ala Cys Arg
                955                 960                 965 tgc tcc cca ctg ggc gct gcc tcg gcc cag tgc cac tat aac ggc aca       3043
Cys Ser Pro Leu Gly Ala Ala Ser Ala Gln Cys His Tyr Asn Gly Thr
            970                 975                 980 tgc gtg tgc agg cct ggc ttc gag ggc tac aaa tgt gac cgc tgc cac       3091
Cys Val Cys Arg Pro Gly Phe Glu Gly Tyr Lys Cys Asp Arg Cys His
        985                 990                 995 tac aac ttc ttc ctc acg gca gac ggc aca cac tgc cag caa tgt ccg       3139
Tyr Asn Phe Phe Leu Thr Ala Asp Gly Thr His Cys Gln Gln Cys Pro
    1000                1005                1010
```

-continued

```
tcc tgc tac gcc ctg gtg aag gag gag aca gcc aag ctg aag gcc aga      3187
Ser Cys Tyr Ala Leu Val Lys Glu Glu Thr Ala Lys Leu Lys Ala Arg
1015                1020                1025                1030 ctg act ttg acg gag ggg tgg ctc caa ggg tcc gac tgt ggc agt ccc      3235
Leu Thr Leu Thr Glu Gly Trp Leu Gln Gly Ser Asp Cys Gly Ser Pro
                1035                1040                1045 tgg gga cca cta gac att ctg ctg gga gag gcc cca agg ggg gac gtc      3283
Trp Gly Pro Leu Asp Ile Leu Leu Gly Glu Ala Pro Arg Gly Asp Val
            1050                1055                1060 tac cag ggc cat cac ctg ctt cca ggg gct cgg gaa gcc ttc ctg gag      3331
Tyr Gln Gly His His Leu Leu Pro Gly Ala Arg Glu Ala Phe Leu Glu
        1065                1070                1075 cag atg atg ggc ctc gag ggt gct gtc aag gcc gcc cgg gag cag ctg      3379
Gln Met Met Gly Leu Glu Gly Ala Val Lys Ala Ala Arg Glu Gln Leu
    1080                1085                1090 cag agg ctg aac aag ggt gcc cgc tgt gcc cag gcc gga tcc cag aag      3427
Gln Arg Leu Asn Lys Gly Ala Arg Cys Ala Gln Ala Gly Ser Gln Lys
1095                1100                1105                1110 acc tgc acc cag ctg gca gac ctg gag gca gtg ctg gag tcc tcg gaa      3475
Thr Cys Thr Gln Leu Ala Asp Leu Glu Ala Val Leu Glu Ser Ser Glu
                1115                1120                1125 gag gag att ctg cat gca gct gcc att ctc gcg tct ctg gag att cct      3523
Glu Glu Ile Leu His Ala Ala Ala Ile Leu Ala Ser Leu Glu Ile Pro
            1130                1135                1140 cag gaa ggt ccc agt cag ccg acc aaa tgg agc cac ctg gcc ata gag      3571
Gln Glu Gly Pro Ser Gln Pro Thr Lys Trp Ser His Leu Ala Ile Glu
        1145                1150                1155 gcc cgt gcc ctc gcc agg agc cac aga gac acc gcc acc aag atc gca      3619
Ala Arg Ala Leu Ala Arg Ser His Arg Asp Thr Ala Thr Lys Ile Ala
    1160                1165                1170 gcc act gct tgg agg gcc ctg ctc gcc tcc aac acc agc tac gcg ctt      3667
Ala Thr Ala Trp Arg Ala Leu Leu Ala Ser Asn Thr Ser Tyr Ala Leu
1175                1180                1185                1190 ctc tgg aat ctg ctg gag gga agg gtg gcc cta gag acc cag cgg gac      3715
Leu Trp Asn Leu Leu Glu Gly Arg Val Ala Leu Glu Thr Gln Arg Asp
                1195                1200                1205 ctg gag gac agg tac cag gag gtc cag gcg gcc cag aaa gca ctg agg      3763
Leu Glu Asp Arg Tyr Gln Glu Val Gln Ala Ala Gln Lys Ala Leu Arg
            1210                1215                1220 acg gct gtg gca gag gtg ctg cct gaa gcg gaa agc gtg ttg gcc acc      3811
Thr Ala Val Ala Glu Val Leu Pro Glu Ala Glu Ser Val Leu Ala Thr
        1225                1230                1235 gtg cag caa gtt ggc gca gat aca gcc ccg tac ctg gcc ttg ctg gct      3859
Val Gln Gln Val Gly Ala Asp Thr Ala Pro Tyr Leu Ala Leu Leu Ala
    1240                1245                1250 tcc ccg gga gct ctg cct cag aag tcc cgg gct gaa gac ctg ggc ctg      3907
Ser Pro Gly Ala Leu Pro Gln Lys Ser Arg Ala Glu Asp Leu Gly Leu
1255                1260                1265                1270 aag gcg aag gcc ctg gag aag aca gtt gca tca tgg cag cac atg gcc      3955
Lys Ala Lys Ala Leu Glu Lys Thr Val Ala Ser Trp Gln His Met Ala
                1275                1280                1285 act gag gct gcc cga acc ctc cag act gct gcc cag gcg acg cta cgg      4003
Thr Glu Ala Ala Arg Thr Leu Gln Thr Ala Ala Gln Ala Thr Leu Arg
            1290                1295                1300 caa aca gaa ccc ctc aca atg gcg cga tct cgg ctc act gca acc ttt      4051
Gln Thr Glu Pro Leu Thr Met Ala Arg Ser Arg Leu Thr Ala Thr Phe
        1305                1310                1315 gcc tcc cag ctg cac cag ggg gcc aga gcc gcc ctg acc cag gct tcc      4099
Ala Ser Gln Leu His Gln Gly Ala Arg Ala Ala Leu Thr Gln Ala Ser
```

-continued

| | | |
|---|---|---|
| tca tct gtc cag gct gcg aca gtg act gtc atg gga gcc agg act ctg<br>Ser Ser Val Gln Ala Ala Thr Val Thr Val Met Gly Ala Arg Thr Leu<br>1335                  1340                  1345                  1350 | | 4147 |
| ctg gct gat ctg gaa gga atg aag ctg cag ttt ccc cgg ccc aag gac<br>Leu Ala Asp Leu Glu Gly Met Lys Leu Gln Phe Pro Arg Pro Lys Asp<br>                  1355                  1360                  1365 | | 4195 |
| cag gcg gca ttg cag agg aag gca gac tcc gtc agt gac aga ctc ctt<br>Gln Ala Ala Leu Gln Arg Lys Ala Asp Ser Val Ser Asp Arg Leu Leu<br>                  1370                  1375                  1380 | | 4243 |
| gca gac acg aga aag aag acc aag cag gcg gag agg atg ctg gga aac<br>Ala Asp Thr Arg Lys Lys Thr Lys Gln Ala Glu Arg Met Leu Gly Asn<br>1385                  1390                  1395 | | 4291 |
| gcg gcc cct ctt tcc tcc agt gcc aag aag aag ggc aga gaa gca gag<br>Ala Ala Pro Leu Ser Ser Ser Ala Lys Lys Lys Gly Arg Glu Ala Glu<br>                  1400                  1405                  1410 | | 4339 |
| gtg ttg gcc aag gac agt gcc aag ctt gcc aag gcc ttg ctg agg gag<br>Val Leu Ala Lys Asp Ser Ala Lys Leu Ala Lys Ala Leu Leu Arg Glu<br>1415                  1420                  1425                  1430 | | 4387 |
| cgg aaa cag gcg cac cgc cgt gcc agc agg ctc acc agc cag acg caa<br>Arg Lys Gln Ala His Arg Arg Ala Ser Arg Leu Thr Ser Gln Thr Gln<br>                  1435                  1440                  1445 | | 4435 |
| gcc acg ctc caa cag gcg tcc cag cag gtg ctg gcg tct gaa gca cgc<br>Ala Thr Leu Gln Gln Ala Ser Gln Gln Val Leu Ala Ser Glu Ala Arg<br>                  1450                  1455                  1460 | | 4483 |
| aga cag gag ctg gag gaa gct gag cgg gtg ggt gct ggg ctg agc gag<br>Arg Gln Glu Leu Glu Glu Ala Glu Arg Val Gly Ala Gly Leu Ser Glu<br>                  1465                  1470                  1475 | | 4531 |
| atg gag cag cag atc cgg gaa tcg cgt atc tca ctg gag aag gac atc<br>Met Glu Gln Gln Ile Arg Glu Ser Arg Ile Ser Leu Glu Lys Asp Ile<br>1480                  1485                  1490 | | 4579 |
| gag acc ttg tca gag ctg ctt gcc agg ctg ggg tcg ctg gac acc cat<br>Glu Thr Leu Ser Glu Leu Leu Ala Arg Leu Gly Ser Leu Asp Thr His<br>1495                  1500                  1505                  1510 | | 4627 |
| caa gcc cca gcc cag gcc ctg aac gag act cag tgg gca cta gaa cgc<br>Gln Ala Pro Ala Gln Ala Leu Asn Glu Thr Gln Trp Ala Leu Glu Arg<br>                  1515                  1520                  1525 | | 4675 |
| ctg agg ctg cag ctg ggc tcc ccg ggg tcc ttg cag agg aaa ctc agt<br>Leu Arg Leu Gln Leu Gly Ser Pro Gly Ser Leu Gln Arg Lys Leu Ser<br>                  1530                  1535                  1540 | | 4723 |
| ctg ctg gag cag gaa tcc cag cag cag gag ctg cag atc cag ggc ttc<br>Leu Leu Glu Gln Glu Ser Gln Gln Gln Glu Leu Gln Ile Gln Gly Phe<br>                  1545                  1550                  1555 | | 4771 |
| gag agt gac ctc gcc gag atc cgc gcc gac aaa cag aac ctg gag gcc<br>Glu Ser Asp Leu Ala Glu Ile Arg Ala Asp Lys Gln Asn Leu Glu Ala<br>1560                  1565                  1570 | | 4819 |
| att ctg cac agc ctg ccc gag aac tgt gcc agc tgg cag tgagggctgc<br>Ile Leu His Ser Leu Pro Glu Asn Cys Ala Ser Trp Gln<br>1575                  1580                  1585 | | 4868 |
| ccagatcccc ggcacacact cccccacctg ctgtttacat gacccagggg gtgcacacta | | 4928 |
| ccccacaggt gtgcccatac agacattccc cggagccggc tgctgtgaac tcgacccccgt | | 4988 |
| gtggatagtc acactccctg ccgattctgt ctgtggcttc ttccctgcca gcaggactga | | 5048 |
| gtgtgcgtac ccagttcacc tggacatgag tgcacactct caccccctgca catgcataaa | | 5108 |
| cgggcacacc ccagtgtcaa taacatacac acgtgagggt gcatgtctgt gtgtatgacc | | 5168 |
| caaataaaaa aaaaaa | | 5184 |

```
<210> SEQ ID NO 5
<211> LENGTH: 1101
<212> TYPE: PRT
<213> ORGANISM: Homo sapiens

<400> SEQUENCE: 5

Met Gln Phe Gln Leu Thr Leu Phe Leu His Leu Gly Trp Leu Ser Tyr
 1               5                  10                  15

Ser Lys Ala Gln Asp Asp Cys Asn Arg Gly Ala Cys His Pro Thr Thr
             20                  25                  30

Gly Asp Leu Leu Val Gly Arg Asn Thr Gln Leu Met Ala Ser Ser Thr
         35                  40                  45

Cys Gly Leu Ser Arg Ala Gln Lys Tyr Cys Ile Leu Ser Tyr Leu Glu
 50                  55                  60

Gly Glu Gln Lys Cys Ser Ile Cys Asp Ser Arg Phe Pro Tyr Asp Pro
 65                  70                  75                  80

Tyr Asp Gln Pro Asn Ser His Thr Ile Glu Asn Val Thr Val Ser Phe
                 85                  90                  95

Glu Pro Asp Arg Glu Lys Lys Trp Trp Gln Ser Glu Asn Gly Leu Asp
            100                 105                 110

His Val Ser Ile Arg Leu Asp Leu Glu Ala Leu Phe Arg Phe Ser His
            115                 120                 125

Leu Ile Leu Thr Phe Lys Thr Phe Arg Pro Ala Ala Met Leu Val Glu
130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
            195                 200                 205

Ile Glu Asn Pro Tyr Ser Pro Tyr Ile Gln Asp Leu Val Thr Leu Thr
        210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Tyr Ala Leu
                245                 250                 255

Tyr Glu Met Ile Val Arg Gly Ser Cys Phe Cys Asn Gly His Ala Ser
            260                 265                 270

Glu Cys Arg Pro Met Gln Lys Met Arg Gly Asp Val Phe Ser Pro Pro
        275                 280                 285

Gly Met Val His Gly Gln Cys Val Cys Gln His Asn Thr Asp Gly Pro
    290                 295                 300

Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
                325                 330                 335

His Ser Ser Arg Cys His Phe Asp Met Thr Thr Tyr Leu Ala Ser Gly
            340                 345                 350

Gly Leu Ser Gly Gly Val Cys Glu Asp Cys Gln His Asn Thr Glu Gly
        355                 360                 365

Gln His Cys Asp Arg Cys Arg Pro Leu Phe Tyr Arg Asp Pro Leu Lys
    370                 375                 380
```

-continued

```
Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
            405                 410                 415

Gly Ser Val Ala Gly Gln Cys Leu Cys Lys Glu Asn Val Glu Gly Ala
            420                 425                 430

Lys Cys Asp Gln Cys Lys Pro Asn His Tyr Gly Leu Ser Ala Thr Asp
            435                 440                 445

Pro Leu Gly Cys Gln Pro Cys Asp Cys Asn Pro Leu Gly Ser Leu Pro
450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
            485                 490                 495

Gly Asn His Leu His Gly Cys Ser Pro Cys Asp Cys Asp Ile Gly Gly
            500                 505                 510

Ala Tyr Ser Asn Val Cys Ser Pro Lys Asn Gly Gln Cys Glu Cys Arg
            515                 520                 525

Pro His Val Thr Gly Arg Ser Cys Ser Glu Pro Ala Pro Gly Tyr Phe
530                 535                 540

Phe Ala Pro Leu Asn Phe Tyr Leu Tyr Glu Ala Glu Ala Thr Thr
545                 550                 555                 560

Leu Gln Gly Leu Ala Pro Leu Gly Ser Glu Thr Phe Gly Gln Ser Pro
            565                 570                 575

Ala Val His Val Val Leu Gly Glu Pro Val Pro Gly Asn Pro Val Thr
            580                 585                 590

Trp Thr Gly Pro Gly Phe Ala Arg Val Leu Pro Gly Ala Gly Leu Arg
            595                 600                 605

Phe Ala Val Asn Asn Ile Pro Phe Pro Val Asp Phe Thr Ile Ala Ile
610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
            645                 650                 655

Lys Pro Gln Ser Phe Ala Leu Pro Ala Ala Thr Arg Ile Met Leu Leu
            660                 665                 670

Pro Thr Pro Ile Cys Leu Glu Pro Asp Val Gln Tyr Ser Ile Asp Val
            675                 680                 685

Tyr Phe Ser Gln Pro Leu Gln Gly Glu Ser His Ala His Ser His Val
            690                 695                 700

Leu Val Asp Ser Leu Gly Leu Ile Pro Gln Ile Asn Ser Leu Glu Asn
705                 710                 715                 720

Phe Cys Ser Lys Gln Asp Leu Asp Glu Tyr Gln Leu His Asn Cys Val
            725                 730                 735

Glu Ile Ala Ser Ala Met Gly Pro Gln Val Leu Pro Gly Ala Cys Glu
            740                 745                 750

Arg Leu Ile Ile Ser Met Ser Ala Lys Leu His Asp Gly Ala Val Ala
            755                 760                 765

Cys Lys Cys His Pro Gln Gly Ser Val Gly Ser Ser Cys Ser Arg Leu
            770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
```

```
            805                 810                 815
Cys His Cys His Pro Gln Gly Ser Lys Asp Thr Val Cys Asp Gln Val
            820                 825                 830
Thr Gly Gln Cys Pro Cys His Gly Glu Val Ser Gly Arg Arg Cys Asp
            835                 840                 845
Arg Cys Leu Ala Gly Tyr Phe Gly Phe Pro Ser Cys His Pro Cys Pro
    850                 855                 860
Cys Asn Arg Phe Ala Glu Leu Cys Asp Pro Glu Thr Gly Ser Cys Phe
865                 870                 875                 880
Asn Cys Gly Gly Phe Thr Thr Gly Arg Asn Cys Glu Arg Cys Ile Asp
                885                 890                 895
Gly Tyr Tyr Gly Asn Pro Ser Ser Gly Gln Pro Cys Arg Pro Cys Leu
            900                 905                 910
Cys Pro Asp Asp Pro Ser Ser Asn Gln Tyr Phe Ala His Ser Cys Tyr
            915                 920                 925
Gln Asn Leu Trp Ser Ser Asp Val Ile Cys Asn Cys Leu Gln Gly Tyr
        930                 935                 940
Thr Gly Thr Gln Cys Gly Glu Cys Ser Thr Gly Phe Tyr Gly Asn Pro
945                 950                 955                 960
Arg Ile Ser Gly Ala Pro Cys Gln Pro Cys Ala Cys Asn Asn Asn Ile
                965                 970                 975
Asp Val Thr Asp Pro Glu Ser Cys Ser Arg Val Thr Gly Glu Cys Leu
            980                 985                 990
Arg Cys Leu His Asn Thr Gln Gly Ala Asn Cys Gln Leu Cys Lys Pro
        995                 1000                1005
Gly His Tyr Gly Ser Ala Leu Asn Gln Thr Cys Arg Arg Cys Ser Cys
    1010                1015                1020
His Ala Ser Gly Val Ser Pro Met Glu Cys Pro Pro Gly Gly Gly Ala
1025                1030                1035                1040
Cys Leu Cys Asp Pro Val Thr Gly Ala Cys Pro Cys Leu Pro Asn Val
                1045                1050                1055
Thr Gly Leu Ala Cys Asp Arg Cys Ala Asp Gly Tyr Trp Asn Leu Val
            1060                1065                1070
Pro Gly Arg Gly Cys Gln Ser Cys Asp Cys Asp Pro Arg Thr Ser Gln
        1075                1080                1085
Ser Ser His Cys Asp Gln Ala Arg Tyr Phe Lys Ala Tyr
    1090                1095                1100

<210> SEQ ID NO 6
<211> LENGTH: 3754
<212> TYPE: DNA
<213> ORGANISM: Homo sapiens
<220> FEATURE:
<221> NAME/KEY: CDS
<222> LOCATION: (81)...(3383)

<400> SEQUENCE: 6
acatgccccg tttgctgcct gaacctctcc acaaagactc ccagatcctg aattgaattt    60
aatcatctcc tgacaaaaga atg caa ttt caa ctg acc ctt ttt ttg cac ctt   113
                        Met Gln Phe Gln Leu Thr Leu Phe Leu His Leu
                        1               5                   10 ggg tgg ctc agt tac tca aaa gct caa gat gac tgc aac agg ggt gcc   161
Gly Trp Leu Ser Tyr Ser Lys Ala Gln Asp Asp Cys Asn Arg Gly Ala
            15                  20                  25 tgt cat ccc acc act ggt gat ctc ctg gtg ggc agg aac acg cag ctt   209
Cys His Pro Thr Thr Gly Asp Leu Leu Val Gly Arg Asn Thr Gln Leu
```

-continued

|  |  |  |  |  |  |  |  |  |  |  |  |  |  |  |  |
|---|---|---|---|---|---|---|---|---|---|---|---|---|---|---|---|
|  |  |  | 30 |  |  |  | 35 |  |  |  | 40 |  |  |  |  |
| atg | gct | tct | tct | acc | tgt | ggg | ctg | agc | aga | gcc | cag | aaa | tac | tgc | atc | 257 |
| Met | Ala | Ser | Ser | Thr | Cys | Gly | Leu | Ser | Arg | Ala | Gln | Lys | Tyr | Cys | Ile |  |
|  | 45 |  |  |  | 50 |  |  |  | 55 |  |  |  |  |  |  |  |
| ctc | agt | tac | ctg | gag | ggg | gaa | caa | aaa | tgc | tcc | atc | tgt | gac | tct | aga | 305 |
| Leu | Ser | Tyr | Leu | Glu | Gly | Glu | Gln | Lys | Cys | Ser | Ile | Cys | Asp | Ser | Arg |  |
| 60 |  |  |  | 65 |  |  |  | 70 |  |  |  | 75 |  |  |  |  |
| ttt | cca | tat | gat | ccg | tat | gac | caa | ccc | aac | agc | cac | acc | att | gag | aat | 353 |
| Phe | Pro | Tyr | Asp | Pro | Tyr | Asp | Gln | Pro | Asn | Ser | His | Thr | Ile | Glu | Asn |  |
|  |  |  | 80 |  |  |  | 85 |  |  |  |  | 90 |  |  |  |  |
| gtc | act | gta | agt | ttt | gaa | cca | gac | aga | gaa | aag | aaa | tgg | tgg | caa | tct | 401 |
| Val | Thr | Val | Ser | Phe | Glu | Pro | Asp | Arg | Glu | Lys | Lys | Trp | Trp | Gln | Ser |  |
|  |  | 95 |  |  |  |  | 100 |  |  |  |  | 105 |  |  |  |  |
| gaa | aat | ggt | ctt | gat | cat | gtc | agc | atc | aga | ctg | gac | tta | gag | gca | tta | 449 |
| Glu | Asn | Gly | Leu | Asp | His | Val | Ser | Ile | Arg | Leu | Asp | Leu | Glu | Ala | Leu |  |
|  | 110 |  |  |  |  | 115 |  |  |  |  | 120 |  |  |  |  |  |
| ttt | cgg | ttc | agc | cac | ctt | atc | ctg | acc | ttt | aag | act | ttt | cgg | cct | gct | 497 |
| Phe | Arg | Phe | Ser | His | Leu | Ile | Leu | Thr | Phe | Lys | Thr | Phe | Arg | Pro | Ala |  |
|  | 125 |  |  |  |  | 130 |  |  |  |  | 135 |  |  |  |  |  |
| gca | atg | tta | gtt | gaa | cgt | tcc | aca | gac | tat | gga | cac | aac | tgg | aaa | gtg | 545 |
| Ala | Met | Leu | Val | Glu | Arg | Ser | Thr | Asp | Tyr | Gly | His | Asn | Trp | Lys | Val |  |
| 140 |  |  |  |  | 145 |  |  |  |  | 150 |  |  |  |  | 155 |  |
| ttc | aaa | tat | ttt | gca | aaa | gac | tgt | gcc | act | tcc | ttt | cct | aac | atc | aca | 593 |
| Phe | Lys | Tyr | Phe | Ala | Lys | Asp | Cys | Ala | Thr | Ser | Phe | Pro | Asn | Ile | Thr |  |
|  |  |  |  | 160 |  |  |  |  | 165 |  |  |  |  | 170 |  |  |
| tct | ggc | cag | gcc | cag | gga | gtg | gga | gac | att | gtt | tgt | gac | tcc | aaa | tac | 641 |
| Ser | Gly | Gln | Ala | Gln | Gly | Val | Gly | Asp | Ile | Val | Cys | Asp | Ser | Lys | Tyr |  |
|  |  | 175 |  |  |  |  | 180 |  |  |  |  | 185 |  |  |  |  |
| tcg | gat | att | gaa | ccc | tca | aca | ggt | gga | gag | gtt | gtt | tta | aaa | gtt | ttg | 689 |
| Ser | Asp | Ile | Glu | Pro | Ser | Thr | Gly | Gly | Glu | Val | Val | Leu | Lys | Val | Leu |  |
|  |  |  | 190 |  |  |  |  | 195 |  |  |  |  | 200 |  |  |  |
| gat | ccc | agt | ttt | gaa | att | gaa | aac | cct | tat | agc | ccc | tac | atc | caa | gac | 737 |
| Asp | Pro | Ser | Phe | Glu | Ile | Glu | Asn | Pro | Tyr | Ser | Pro | Tyr | Ile | Gln | Asp |  |
|  | 205 |  |  |  |  | 210 |  |  |  |  | 215 |  |  |  |  |  |
| ctt | gtg | aca | ttg | aca | aac | ctg | agg | ata | aac | ttt | acc | aag | ctc | cac | acc | 785 |
| Leu | Val | Thr | Leu | Thr | Asn | Leu | Arg | Ile | Asn | Phe | Thr | Lys | Leu | His | Thr |  |
| 220 |  |  |  |  | 225 |  |  |  |  | 230 |  |  |  |  | 235 |  |
| ctt | ggg | gat | gct | ttg | ctt | gga | agg | agg | caa | aat | gat | tcc | ctt | gat | aaa | 833 |
| Leu | Gly | Asp | Ala | Leu | Leu | Gly | Arg | Arg | Gln | Asn | Asp | Ser | Leu | Asp | Lys |  |
|  |  |  |  | 240 |  |  |  |  | 245 |  |  |  |  | 250 |  |  |
| tac | tac | tat | gct | ctg | tac | gag | atg | att | gtt | cgg | gga | agc | tgc | ttt | tgc | 881 |
| Tyr | Tyr | Tyr | Ala | Leu | Tyr | Glu | Met | Ile | Val | Arg | Gly | Ser | Cys | Phe | Cys |  |
|  |  |  | 255 |  |  |  |  | 260 |  |  |  |  | 265 |  |  |  |
| aat | ggc | cat | gct | agc | gaa | tgt | cgc | cct | atg | cag | aag | atg | cgg | gga | gat | 929 |
| Asn | Gly | His | Ala | Ser | Glu | Cys | Arg | Pro | Met | Gln | Lys | Met | Arg | Gly | Asp |  |
|  |  | 270 |  |  |  |  | 275 |  |  |  |  | 280 |  |  |  |  |
| gtt | ttc | agc | cct | cct | gga | atg | gtt | cac | ggt | cag | tgt | gtg | tgt | cag | cac | 977 |
| Val | Phe | Ser | Pro | Pro | Gly | Met | Val | His | Gly | Gln | Cys | Val | Cys | Gln | His |  |
|  | 285 |  |  |  |  | 290 |  |  |  |  | 295 |  |  |  |  |  |
| aat | aca | gat | ggt | ccg | aac | tgt | gag | aga | tgc | aag | gac | ttc | ttc | cag | gat | 1025 |
| Asn | Thr | Asp | Gly | Pro | Asn | Cys | Glu | Arg | Cys | Lys | Asp | Phe | Phe | Gln | Asp |  |
| 300 |  |  |  |  | 305 |  |  |  |  | 310 |  |  |  |  | 315 |  |
| gct | cct | tgg | agg | cca | gct | gca | gac | ctc | cag | gac | aac | gct | tgc | aga | tcg | 1073 |
| Ala | Pro | Trp | Arg | Pro | Ala | Ala | Asp | Leu | Gln | Asp | Asn | Ala | Cys | Arg | Ser |  |
|  |  |  | 320 |  |  |  |  | 325 |  |  |  |  | 330 |  |  |  |
| tgc | agc | tgt | aat | agc | cac | tcc | agc | cgc | tgt | cac | ttt | gac | atg | act | acg | 1121 |
| Cys | Ser | Cys | Asn | Ser | His | Ser | Ser | Arg | Cys | His | Phe | Asp | Met | Thr | Thr |  |
|  |  |  |  | 335 |  |  |  |  | 340 |  |  |  |  | 345 |  |  |
| tac | ctg | gca | agc | ggt | ggc | ctc | agc | ggg | ggc | gtg | tgt | gaa | gac | tgc | cag | 1169 |

```
                                                            -continued

Tyr Leu Ala Ser Gly Gly Leu Ser Gly Gly Val Cys Glu Asp Cys Gln
            350                 355                 360 cac aac act gag ggg cag cac tgc gac cgc tgc aga ccc ctc ttc tac    1217
His Asn Thr Glu Gly Gln His Cys Asp Arg Cys Arg Pro Leu Phe Tyr
        365                 370                 375 agg gac ccg ctc aag acc atc tca gat ccc tac gcg tgc att cct tgt    1265
Arg Asp Pro Leu Lys Thr Ile Ser Asp Pro Tyr Ala Cys Ile Pro Cys
380                 385                 390                 395 gaa tgt gac ccc gat ggg acc ata tct ggt ggc att tgt gtg agc cac    1313
Glu Cys Asp Pro Asp Gly Thr Ile Ser Gly Gly Ile Cys Val Ser His
                400                 405                 410 tct gat cct gcc tta ggg tct gtg gcc ggc cag tgc ctt tgt aaa gag    1361
Ser Asp Pro Ala Leu Gly Ser Val Ala Gly Gln Cys Leu Cys Lys Glu
            415                 420                 425 aac gtg gaa gga gcc aaa tgc gac cag tgc aaa ccc aac cac tac gga    1409
Asn Val Glu Gly Ala Lys Cys Asp Gln Cys Lys Pro Asn His Tyr Gly
        430                 435                 440 cta agc gcc acc gac ccc ctg ggc tgc cag ccc tgc gac tgt aac ccc    1457
Leu Ser Ala Thr Asp Pro Leu Gly Cys Gln Pro Cys Asp Cys Asn Pro
    445                 450                 455 ctt ggg agt ctg cca ttc ttg acc tgt gat gtg gat aca ggc caa tgc    1505
Leu Gly Ser Leu Pro Phe Leu Thr Cys Asp Val Asp Thr Gly Gln Cys
460                 465                 470                 475 ttg tgc ctg tca tat gtc acc gga gca cac tgc gaa gaa tgc act gtt    1553
Leu Cys Leu Ser Tyr Val Thr Gly Ala His Cys Glu Glu Cys Thr Val
                480                 485                 490 gga tac tgg ggc ctg gga aat cat ctc cat ggg tgt tct ccc tgt gac    1601
Gly Tyr Trp Gly Leu Gly Asn His Leu His Gly Cys Ser Pro Cys Asp
            495                 500                 505 tgt gat att gga ggt gct tat tct aac gtg tgc tca ccc aag aat ggg    1649
Cys Asp Ile Gly Gly Ala Tyr Ser Asn Val Cys Ser Pro Lys Asn Gly
        510                 515                 520 cag tgt gaa tgc cgc cca cat gtc act ggc cgt agc tgc tct gaa cca    1697
Gln Cys Glu Cys Arg Pro His Val Thr Gly Arg Ser Cys Ser Glu Pro
    525                 530                 535 gcc cct ggc tac ttc ttt gct cct ttg aat ttc tat ctc tac gag gca    1745
Ala Pro Gly Tyr Phe Phe Ala Pro Leu Asn Phe Tyr Leu Tyr Glu Ala
540                 545                 550                 555 gag gaa gcc aca aca ctc caa gga ctg gcg cct ttg ggc tcg gag acg    1793
Glu Glu Ala Thr Thr Leu Gln Gly Leu Ala Pro Leu Gly Ser Glu Thr
                560                 565                 570 ttt ggc cag agt cct gct gtt cac gtt gtt tta gga gag cca gtt cct    1841
Phe Gly Gln Ser Pro Ala Val His Val Val Leu Gly Glu Pro Val Pro
            575                 580                 585 ggg aac cct gtt aca tgg act gga cct gga ttt gcc agg gtt ctc cct    1889
Gly Asn Pro Val Thr Trp Thr Gly Pro Gly Phe Ala Arg Val Leu Pro
        590                 595                 600 ggg gct ggc ttg aga ttt gct gtc aac aac att ccc ttt cct gtg gac    1937
Gly Ala Gly Leu Arg Phe Ala Val Asn Asn Ile Pro Phe Pro Val Asp
    605                 610                 615 ttc acc att gcc att cac tat gaa acc cag tct gca gct gac tgg act    1985
Phe Thr Ile Ala Ile His Tyr Glu Thr Gln Ser Ala Ala Asp Trp Thr
620                 625                 630                 635 gtc cag att gtg gtg aac ccc cct gga ggg agt gag cac tgc ata ccc    2033
Val Gln Ile Val Val Asn Pro Pro Gly Gly Ser Glu His Cys Ile Pro
                640                 645                 650 aag act cta cag tca aag cct cag tct ttt gcc tta cca gcg gct acg    2081
Lys Thr Leu Gln Ser Lys Pro Gln Ser Phe Ala Leu Pro Ala Ala Thr
            655                 660                 665
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | atc | atg | ctg | ctt | ccc | aca | ccc | atc | tgt | tta | gaa | cca | gat | gta | caa | 2129 |
| Arg | Ile | Met | Leu | Leu | Pro | Thr | Pro | Ile | Cys | Leu | Glu | Pro | Asp | Val | Gln |      |
|     |     | 670 |     |     |     |     | 675 |     |     |     |     | 680 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tat | tcc | ata | gat | gtc | tat | ttt | tct | cag | cct | ttg | caa | gga | gag | tcc | cac | 2177 |
| Tyr | Ser | Ile | Asp | Val | Tyr | Phe | Ser | Gln | Pro | Leu | Gln | Gly | Glu | Ser | His |      |
|     |     | 685 |     |     |     |     | 690 |     |     |     |     | 695 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gct | cat | tca | cat | gtc | ctg | gtg | gac | tct | ctt | ggc | ctt | att | ccc | caa | atc | 2225 |
| Ala | His | Ser | His | Val | Leu | Val | Asp | Ser | Leu | Gly | Leu | Ile | Pro | Gln | Ile |      |
| 700 |     |     |     |     | 705 |     |     |     |     | 710 |     |     |     |     | 715 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aat | tca | ttg | gag | aat | ttc | tgc | agc | aag | cag | gac | tta | gat | gag | tat | cag | 2273 |
| Asn | Ser | Leu | Glu | Asn | Phe | Cys | Ser | Lys | Gln | Asp | Leu | Asp | Glu | Tyr | Gln |      |
|     |     |     |     | 720 |     |     |     |     | 725 |     |     |     |     | 730 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctt | cac | aac | tgt | gtt | gaa | att | gcc | tca | gca | atg | gga | cct | caa | gtg | ctc | 2321 |
| Leu | His | Asn | Cys | Val | Glu | Ile | Ala | Ser | Ala | Met | Gly | Pro | Gln | Val | Leu |      |
|     |     |     | 735 |     |     |     |     | 740 |     |     |     |     | 745 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ccg | ggt | gcc | tgt | gaa | agg | ctg | atc | atc | agc | atg | tct | gcc | aag | ctg | cat | 2369 |
| Pro | Gly | Ala | Cys | Glu | Arg | Leu | Ile | Ile | Ser | Met | Ser | Ala | Lys | Leu | His |      |
|     |     | 750 |     |     |     |     | 755 |     |     |     |     | 760 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gat | ggg | gct | gtg | gcc | tgc | aag | tgt | cac | ccc | cag | ggc | tca | gtc | gga | tcc | 2417 |
| Asp | Gly | Ala | Val | Ala | Cys | Lys | Cys | His | Pro | Gln | Gly | Ser | Val | Gly | Ser |      |
| 765 |     |     |     |     | 770 |     |     |     |     | 775 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agc | tgc | agc | cga | ctt | gga | ggc | cag | tgc | cag | tgt | aaa | cct | ctt | gtg | gtc | 2465 |
| Ser | Cys | Ser | Arg | Leu | Gly | Gly | Gln | Cys | Gln | Cys | Lys | Pro | Leu | Val | Val |      |
| 780 |     |     |     |     | 785 |     |     |     |     | 790 |     |     |     |     | 795 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggg | cgc | tgc | tgt | gac | agg | tgc | tca | act | gga | agc | tat | gat | ttg | ggg | cat | 2513 |
| Gly | Arg | Cys | Cys | Asp | Arg | Cys | Ser | Thr | Gly | Ser | Tyr | Asp | Leu | Gly | His |      |
|     |     |     |     | 800 |     |     |     |     | 805 |     |     |     |     | 810 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cac | ggc | tgt | cac | cca | tgt | cac | tgc | cat | cct | caa | gga | tca | aag | gac | act | 2561 |
| His | Gly | Cys | His | Pro | Cys | His | Cys | His | Pro | Gln | Gly | Ser | Lys | Asp | Thr |      |
|     |     |     | 815 |     |     |     |     | 820 |     |     |     |     | 825 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gta | tgt | gac | caa | gta | aca | gga | cag | tgc | ccc | tgc | cat | gga | gag | gtg | tct | 2609 |
| Val | Cys | Asp | Gln | Val | Thr | Gly | Gln | Cys | Pro | Cys | His | Gly | Glu | Val | Ser |      |
|     |     | 830 |     |     |     |     | 835 |     |     |     |     | 840 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | cgc | cgc | tgt | gat | cgc | tgc | ctg | gca | ggc | tac | ttt | gga | ttt | ccc | agc | 2657 |
| Gly | Arg | Arg | Cys | Asp | Arg | Cys | Leu | Ala | Gly | Tyr | Phe | Gly | Phe | Pro | Ser |      |
| 845 |     |     |     |     | 850 |     |     |     |     | 855 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgc | cac | cct | tgc | cct | tgt | aat | agg | ttt | gct | gaa | ctt | tgt | gat | cct | gag | 2705 |
| Cys | His | Pro | Cys | Pro | Cys | Asn | Arg | Phe | Ala | Glu | Leu | Cys | Asp | Pro | Glu |      |
| 860 |     |     |     |     | 865 |     |     |     |     | 870 |     |     |     |     | 875 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | ggg | tca | tgc | ttc | aat | tgt | gga | ggc | ttt | aca | act | ggc | aga | aac | tgt | 2753 |
| Thr | Gly | Ser | Cys | Phe | Asn | Cys | Gly | Gly | Phe | Thr | Thr | Gly | Arg | Asn | Cys |      |
|     |     |     |     | 880 |     |     |     |     | 885 |     |     |     |     | 890 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | agg | tgt | att | gat | ggt | tac | tat | gga | aat | cct | tct | tca | gga | cag | ccc | 2801 |
| Glu | Arg | Cys | Ile | Asp | Gly | Tyr | Tyr | Gly | Asn | Pro | Ser | Ser | Gly | Gln | Pro |      |
|     |     |     | 895 |     |     |     |     | 900 |     |     |     |     | 905 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgt | cgt | cct | tgc | ctg | tgt | cca | gat | gat | ccc | tca | agc | aat | cag | tat | ttt | 2849 |
| Cys | Arg | Pro | Cys | Leu | Cys | Pro | Asp | Asp | Pro | Ser | Ser | Asn | Gln | Tyr | Phe |      |
|     |     | 910 |     |     |     |     | 915 |     |     |     |     | 920 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | cat | tcc | tgt | tat | cag | aat | ctg | tgg | agc | tca | gat | gta | atc | tgc | aat | 2897 |
| Ala | His | Ser | Cys | Tyr | Gln | Asn | Leu | Trp | Ser | Ser | Asp | Val | Ile | Cys | Asn |      |
| 925 |     |     |     |     | 930 |     |     |     |     | 935 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgt | ctt | caa | ggt | tat | acg | ggt | act | cag | tgt | gga | gaa | tgc | tct | act | ggt | 2945 |
| Cys | Leu | Gln | Gly | Tyr | Thr | Gly | Thr | Gln | Cys | Gly | Glu | Cys | Ser | Thr | Gly |      |
| 940 |     |     |     |     | 945 |     |     |     |     | 950 |     |     |     |     | 955 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | tat | gga | aat | cca | aga | att | tca | gga | gca | cct | tgc | caa | cca | tgt | gcc | 2993 |
| Phe | Tyr | Gly | Asn | Pro | Arg | Ile | Ser | Gly | Ala | Pro | Cys | Gln | Pro | Cys | Ala |      |
|     |     |     |     | 960 |     |     |     |     | 965 |     |     |     |     | 970 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgc | aac | aac | aac | ata | gat | gta | acc | gat | cca | gag | tcc | tgc | agc | cgg | gta | 3041 |
| Cys | Asn | Asn | Asn | Ile | Asp | Val | Thr | Asp | Pro | Glu | Ser | Cys | Ser | Arg | Val |      |
|     |     |     |     | 975 |     |     |     |     | 980 |     |     |     |     | 985 |     |      |

```
aca ggg gag tgc ctt cga tgt ttg cac aac act cag ggc gca aac tgc     3089
Thr Gly Glu Cys Leu Arg Cys Leu His Asn Thr Gln Gly Ala Asn Cys
            990                 995                 1000 cag ctc tgc aaa cca ggt cac tat gga tca gcc ctc aat cag acc tgc     3137
Gln Leu Cys Lys Pro Gly His Tyr Gly Ser Ala Leu Asn Gln Thr Cys
    1005                1010                1015 aga aga tgc tcc tgc cat gct tcc ggc gtg agt ccc atg gag tgt ccc     3185
Arg Arg Cys Ser Cys His Ala Ser Gly Val Ser Pro Met Glu Cys Pro
1020            1025                1030                1035 cct ggt ggg gga gct tgc ctc tgt gac cct gtc act ggt gca tgt cct     3233
Pro Gly Gly Gly Ala Cys Leu Cys Asp Pro Val Thr Gly Ala Cys Pro
                1040                1045                1050 tgt ctg ccg aat gtc aca ggc ctg gcc tgt gac cgt tgt gct gat gga     3281
Cys Leu Pro Asn Val Thr Gly Leu Ala Cys Asp Arg Cys Ala Asp Gly
            1055                1060                1065 tac tgg aat ctg gtc cct ggc aga gga tgt cag tca tgt gac tgt gac     3329
Tyr Trp Asn Leu Val Pro Gly Arg Gly Cys Gln Ser Cys Asp Cys Asp
    1070                1075                1080 cct agg acc tct caa agt agc cac tgt gac cag gca aga tac ttt aaa     3377
Pro Arg Thr Ser Gln Ser Ser His Cys Asp Gln Ala Arg Tyr Phe Lys
1085            1090                1095 gct tac tagtgcatca aagtgagcat gatagtgaga catggtttct aatgtgtaaa      3433
Ala Tyr
1100 gaaagtttct tttatgtact gttgttaatt agtgcattga acaggatgc cttacaggga    3493 tggagtcagc ctctatcaag gaatgaaacc aaaaaagaga atgagcatct caagttcagc   3553 ttcgcctact tcagtttccc ctctgtgact gaggaagtca gaattcatac acagtgaaac   3613 acagacatca gcctcacctt tcactatttc atacatgtaa ccatagggaa gacctaagaa   3673 atagttaatc agaagagatt atgaatcaga atgaaaataa acagatacct tcaaaaccta   3733 aaaaaaaaaa aaaaaaaaaa a                                             3754

<210> SEQ ID NO 7
<211> LENGTH: 3110
<212> TYPE: PRT
<213> ORGANISM: Homo sapiens

<400> SEQUENCE: 7

Met Pro Gly Ala Ala Gly Val Leu Leu Leu Leu Leu Ser Gly Gly
 1               5                  10                  15

Leu Gly Gly Val Gln Ala Gln Arg Pro Gln Gln Arg Gln Ser Gln
            20                  25                  30

Ala His Gln Gln Arg Gly Leu Phe Pro Ala Val Leu Asn Leu Ala Ser
        35                  40                  45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140
```

-continued

```
Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
            165                 170                 175

Leu Thr Leu Tyr Asn Ile Tyr Pro Arg Thr Gly Pro Pro Ser Tyr Ala
                180                 185                 190

Lys Asp Asp Glu Val Ile Cys Thr Ser Phe Tyr Ser Lys Ile His Pro
            195                 200                 205

Leu Glu Asn Gly Glu Ile His Ile Ser Leu Ile Asn Gly Arg Pro Ser
            210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
            275                 280                 285

Cys Tyr Gly His Ala Arg Ala Cys Pro Leu Asp Pro Ala Thr Asn Lys
            290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
            355                 360                 365

Arg Gly Lys Tyr Ile Gly Gly Val Cys Ile Asn Cys Thr Gln Asn
            370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
            435                 440                 445

Gly Gly Val Ser Cys Asp Arg Cys Ala Arg Gly Tyr Thr Gly Tyr Pro
450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
            515                 520                 525

Ser Ser Tyr Trp Thr Tyr Gly Lys Ile Gln Asp Met Ser Gly Trp Tyr
530                 535                 540

Leu Thr Asp Leu Pro Gly Arg Ile Arg Val Ala Pro Gln Gln Asp Asp
545                 550                 555                 560
```

-continued

```
Leu Asp Ser Pro Gln Gln Ile Ser Ile Ser Asn Ala Glu Ala Arg Gln
            565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
            595                 600                 605

Asp Leu Glu Glu Glu Glu Asp Thr Glu Arg Val Leu Gln Leu Met
610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
            645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
            675                 680                 685

Thr Tyr Ser Phe Gly Met Asp Ala Ile Phe Arg Leu Ser Ser Val Asn
            690                 695                 700

Leu Glu Ser Ala Val Ser Tyr Pro Thr Asp Gly Ser Ile Ala Ala Ala
705                 710                 715                 720

Val Glu Val Cys Gln Cys Pro Gly Tyr Thr Gly Ser Ser Cys Glu
            725                 730                 735

Ser Cys Trp Pro Arg His Arg Val Asn Gly Thr Ile Phe Gly Gly
            740                 745                 750

Ile Cys Glu Pro Cys Gln Cys Phe Gly His Ala Glu Ser Cys Asp Asp
            755                 760                 765

Val Thr Gly Glu Cys Leu Asn Cys Lys Asp His Thr Gly Gly Pro Tyr
770                 775                 780

Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
            805                 810                 815

Asn Phe Ser Pro Thr Cys His Leu Asp Arg Ser Leu Gly Leu Ile Cys
            820                 825                 830

Asp Gly Cys Pro Val Gly Tyr Thr Gly Pro Arg Cys Glu Arg Cys Ala
            835                 840                 845

Glu Gly Tyr Phe Gly Gln Pro Ser Val Pro Gly Gly Ser Cys Gln Pro
            850                 855                 860

Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
            885                 890                 895

Tyr Cys Glu Leu Cys Ala Asp Gly Tyr Phe Gly Asp Ala Val Asp Ala
            900                 905                 910

Lys Asn Cys Gln Pro Cys Arg Cys Asn Ala Gly Gly Ser Phe Ser Glu
            915                 920                 925

Val Cys His Ser Gln Thr Gly Gln Cys Glu Cys Arg Ala Asn Val Gln
            930                 935                 940

Gly Gln Arg Cys Asp Lys Cys Lys Ala Gly Thr Phe Gly Leu Gln Ser
945                 950                 955                 960

Ala Arg Gly Cys Val Pro Cys Asn Cys Asn Ser Phe Gly Ser Lys Ser
            965                 970                 975

Phe Asp Cys Glu Glu Ser Gly Gln Cys Trp Cys Gln Pro Gly Val Thr
```

-continued

```
                980              985              990
Gly Lys Lys Cys Asp Arg Cys Ala His Gly Tyr Phe Asn Phe Gln Glu
            995              1000             1005

Gly Gly Cys Thr Ala Cys Glu Cys Ser His Leu Gly Asn Asn Cys Asp
1010             1015             1020

Pro Lys Thr Gly Arg Cys Ile Cys Pro Pro Asn Thr Ile Gly Glu Lys
1025             1030             1035             1040

Cys Ser Lys Cys Ala Pro Asn Thr Trp Gly His Ser Ile Thr Thr Gly
            1045             1050             1055

Cys Lys Ala Cys Asn Cys Ser Thr Val Gly Ser Leu Asp Phe Gln Cys
            1060             1065             1070

Asn Val Asn Thr Gly Gln Cys Asn Cys His Pro Lys Phe Ser Gly Ala
            1075             1080             1085

Lys Cys Thr Glu Cys Ser Arg Gly His Trp Asn Tyr Pro Arg Cys Asn
            1090             1095             1100

Leu Cys Asp Cys Phe Leu Pro Gly Thr Asp Ala Thr Cys Asp Ser
1105             1110             1115             1120

Glu Thr Lys Lys Cys Ser Cys Ser Asp Gln Thr Gly Gln Cys Thr Cys
            1125             1130             1135

Lys Val Asn Val Glu Gly Ile His Cys Asp Arg Cys Arg Pro Gly Lys
            1140             1145             1150

Phe Gly Leu Asp Ala Lys Asn Pro Leu Gly Cys Ser Ser Cys Tyr Cys
            1155             1160             1165

Phe Gly Thr Thr Thr Gln Cys Ser Glu Ala Lys Gly Leu Ile Arg Thr
            1170             1175             1180

Trp Val Thr Leu Lys Ala Glu Gln Thr Ile Leu Pro Leu Val Asp Glu
1185             1190             1195             1200

Ala Leu Gln His Thr Thr Thr Lys Gly Ile Val Phe Gln His Pro Glu
            1205             1210             1215

Ile Val Ala His Met Asp Leu Met Arg Glu Asp Leu His Leu Glu Pro
            1220             1225             1230

Phe Tyr Trp Lys Leu Pro Glu Gln Phe Glu Gly Lys Lys Leu Met Ala
            1235             1240             1245

Tyr Gly Gly Lys Leu Lys Tyr Ala Ile Tyr Phe Glu Ala Arg Glu Glu
            1250             1255             1260

Thr Gly Phe Ser Thr Tyr Asn Pro Gln Val Ile Ile Arg Gly Gly Thr
1265             1270             1275             1280

Pro Thr His Ala Arg Ile Ile Val Arg His Met Ala Ala Pro Leu Ile
            1285             1290             1295

Gly Gln Leu Thr Arg His Glu Ile Glu Met Thr Glu Lys Glu Trp Lys
            1300             1305             1310

Tyr Tyr Gly Asp Asp Pro Arg Val His Arg Thr Val Thr Arg Glu Asp
            1315             1320             1325

Phe Leu Asp Ile Leu Tyr Asp Ile His Tyr Ile Leu Ile Lys Ala Thr
            1330             1335             1340

Tyr Gly Asn Phe Met Arg Gln Ser Arg Ile Ser Glu Ile Ser Met Glu
1345             1350             1355             1360

Val Ala Glu Gln Gly Arg Gly Thr Thr Met Thr Pro Pro Ala Asp Leu
            1365             1370             1375

Ile Glu Lys Cys Asp Cys Pro Leu Gly Tyr Ser Gly Leu Ser Cys Glu
            1380             1385             1390

Ala Cys Leu Pro Gly Phe Tyr Arg Leu Arg Ser Gln Pro Gly Gly Arg
            1395             1400             1405
```

-continued

```
Thr Pro Gly Pro Thr Leu Gly Thr Cys Val Pro Cys Gln Cys Asn Gly
    1410                1415                1420
His Ser Ser Leu Cys Asp Pro Glu Thr Ser Ile Cys Gln Asn Cys Gln
1425                1430                1435                1440
His His Thr Ala Gly Asp Phe Cys Glu Arg Cys Ala Leu Gly Tyr Tyr
                1445                1450                1455
Gly Ile Val Lys Gly Leu Pro Asn Asp Cys Gln Gln Cys Ala Cys Pro
                1460                1465                1470
Leu Ile Ser Ser Ser Asn Asn Phe Ser Pro Ser Cys Val Ala Glu Gly
            1475                1480                1485
Leu Asp Asp Tyr Arg Cys Thr Ala Cys Pro Arg Gly Tyr Glu Gly Gln
            1490                1495                1500
Tyr Cys Glu Arg Cys Ala Pro Gly Tyr Thr Gly Ser Pro Gly Asn Pro
1505                1510                1515                1520
Gly Gly Ser Cys Gln Glu Cys Glu Cys Asp Pro Tyr Gly Ser Leu Pro
                1525                1530                1535
Val Pro Cys Asp Pro Val Thr Gly Phe Cys Thr Cys Arg Pro Gly Ala
                1540                1545                1550
Thr Gly Arg Lys Cys Asp Gly Cys Lys His Trp His Ala Arg Glu Gly
            1555                1560                1565
Trp Glu Cys Val Phe Cys Gly Asp Glu Cys Thr Gly Leu Leu Leu Gly
            1570                1575                1580
Asp Leu Ala Arg Leu Glu Gln Met Val Met Ser Ile Asn Leu Thr Gly
1585                1590                1595                1600
Pro Leu Pro Ala Pro Tyr Lys Met Leu Tyr Gly Leu Glu Asn Met Thr
                1605                1610                1615
Gln Glu Leu Lys His Leu Leu Ser Pro Gln Arg Ala Pro Glu Arg Leu
                1620                1625                1630
Ile Gln Leu Ala Glu Gly Asn Leu Asn Thr Leu Val Thr Glu Met Asn
            1635                1640                1645
Glu Leu Leu Thr Arg Ala Thr Lys Val Thr Ala Asp Gly Glu Gln Thr
            1650                1655                1660
Gly Gln Asp Ala Glu Arg Thr Asn Thr Arg Ala Lys Ser Leu Gly Glu
1665                1670                1675                1680
Phe Ile Lys Glu Leu Ala Arg Asp Ala Glu Ala Val Asn Glu Lys Ala
                1685                1690                1695
Ile Lys Leu Asn Glu Thr Leu Gly Thr Arg Asp Glu Ala Phe Glu Arg
                1700                1705                1710
Asn Leu Glu Gly Leu Gln Lys Glu Ile Asp Gln Met Ile Lys Glu Leu
            1715                1720                1725
Arg Arg Lys Asn Leu Glu Thr Gln Lys Glu Ile Ala Glu Asp Glu Leu
        1730                1735                1740
Val Ala Ala Glu Ala Leu Leu Lys Val Lys Lys Leu Phe Gly Glu
1745                1750                1755                1760
Ser Arg Gly Glu Asn Glu Glu Met Glu Lys Asp Leu Arg Glu Lys Leu
                1765                1770                1775
Ala Asp Tyr Lys Asn Lys Val Asp Asp Ala Trp Asp Leu Leu Arg Glu
            1780                1785                1790
Ala Thr Asp Lys Ile Arg Glu Ala Asn Arg Leu Phe Ala Val Asn Gln
            1795                1800                1805
Lys Asn Met Thr Ala Leu Glu Lys Lys Lys Glu Ala Val Glu Ser Gly
        1810                1815                1820
```

```
Lys Arg Gln Ile Glu Asn Thr Leu Lys Glu Gly Asn Asp Ile Leu Asp
1825                1830                1835                1840

Glu Ala Asn Arg Leu Ala Asp Glu Ile Asn Ser Ile Ile Asp Tyr Val
            1845                1850                1855

Glu Asp Ile Gln Thr Lys Leu Pro Pro Met Ser Glu Glu Leu Asn Asp
            1860                1865                1870

Lys Ile Asp Asp Leu Ser Gln Gly Ile Lys Asp Arg Lys Leu Ala Glu
            1875                1880                1885

Lys Val Ser Gln Ala Glu Ser His Ala Ala Gln Leu Asn Asp Ser Ser
            1890                1895                1900

Ala Val Leu Asp Gly Ile Leu Asp Glu Ala Lys Asn Ile Ser Phe Asn
1905                1910                1915                1920

Ala Thr Ala Ala Phe Lys Ala Tyr Ser Asn Ile Lys Asp Tyr Ile Asp
            1925                1930                1935

Glu Ala Glu Lys Val Ala Lys Glu Ala Lys Asp Leu Ala His Glu Ala
            1940                1945                1950

Thr Lys Leu Ala Thr Gly Pro Arg Gly Leu Leu Lys Glu Asp Ala Lys
            1955                1960                1965

Gly Cys Leu Gln Lys Ser Phe Arg Ile Leu Asn Glu Ala Lys Lys Leu
            1970                1975                1980

Ala Asn Asp Val Lys Glu Asn Gly Asp His Leu Asn Gly Leu Lys Thr
1985                1990                1995                2000

Arg Ile Glu Asn Ala Asp Ala Arg Asn Gly Asp Leu Leu Arg Thr Leu
            2005                2010                2015

Asn Asp Thr Leu Gly Lys Leu Ser Ala Ile Pro Asn Asp Thr Ala Ala
            2020                2025                2030

Lys Leu Gln Ala Val Lys Asp Lys Ala Arg Gln Ala Asn Asp Thr Ala
            2035                2040                2045

Lys Asp Val Leu Ala Gln Ile Thr Glu Leu His Gln Asn Leu Asp Gly
            2050                2055                2060

Leu Lys Lys Asn Tyr Asn Lys Leu Ala Asp Ser Val Ala Lys Thr Asn
2065                2070                2075                2080

Ala Val Val Lys Asp Pro Ser Lys Asn Lys Ile Ile Ala Asp Ala Asp
            2085                2090                2095

Ala Thr Val Lys Asn Leu Glu Gln Glu Ala Asp Arg Leu Ile Asp Lys
            2100                2105                2110

Leu Lys Pro Ile Lys Glu Leu Glu Asp Asn Leu Lys Lys Asn Ile Ser
            2115                2120                2125

Glu Ile Lys Glu Leu Ile Asn Gln Ala Arg Lys Gln Ala Asn Ser Ile
            2130                2135                2140

Lys Val Ser Val Ser Ser Gly Gly Asp Cys Ile Arg Thr Tyr Lys Pro
2145                2150                2155                2160

Glu Ile Lys Lys Gly Ser Tyr Asn Asn Ile Val Val Asn Val Lys Thr
            2165                2170                2175

Ala Val Ala Asp Asn Leu Leu Phe Tyr Leu Gly Ser Ala Lys Phe Ile
            2180                2185                2190

Asp Phe Leu Ala Ile Glu Met Arg Lys Gly Lys Val Ser Phe Leu Trp
            2195                2200                2205

Asp Val Gly Ser Gly Val Gly Arg Val Glu Tyr Pro Asp Leu Thr Ile
            2210                2215                2220

Asp Asp Ser Tyr Trp Tyr Arg Ile Val Ala Ser Arg Thr Gly Arg Asn
2225                2230                2235                2240

Gly Thr Ile Ser Val Arg Ala Leu Asp Gly Pro Lys Ala Ser Ile Val
```

```
                     2245                2250                2255
Pro Ser Thr His His Ser Thr Ser Pro Pro Gly Tyr Thr Ile Leu Asp
                 2260                2265                2270
Val Asp Ala Asn Ala Met Leu Phe Val Gly Gly Leu Thr Gly Lys Leu
             2275                2280                2285
Lys Lys Ala Asp Ala Val Arg Val Ile Thr Phe Thr Gly Cys Met Gly
         2290                2295                2300
Glu Thr Tyr Phe Asp Asn Lys Pro Ile Gly Leu Trp Asn Phe Arg Glu
2305                2310                2315                2320
Lys Glu Gly Asp Cys Lys Gly Cys Thr Val Ser Pro Gln Val Glu Asp
                 2325                2330                2335
Ser Glu Gly Thr Ile Gln Phe Asp Gly Glu Gly Tyr Ala Leu Val Ser
             2340                2345                2350
Arg Pro Ile Arg Trp Tyr Pro Asn Ile Ser Thr Val Met Phe Lys Phe
         2355                2360                2365
Arg Thr Phe Ser Ser Ser Ala Leu Leu Met Tyr Leu Ala Thr Arg Asp
     2370                2375                2380
Leu Arg Asp Phe Met Ser Val Glu Leu Thr Asp Gly His Ile Lys Val
2385                2390                2395                2400
Ser Tyr Asp Leu Gly Ser Gly Met Ala Ser Val Val Ser Asn Gln Asn
                 2405                2410                2415
His Asn Asp Gly Lys Trp Lys Ser Phe Thr Leu Ser Arg Ile Gln Lys
             2420                2425                2430
Gln Ala Asn Ile Ser Ile Val Asp Ile Asp Thr Asn Gln Glu Glu Asn
         2435                2440                2445
Ile Ala Thr Ser Ser Ser Gly Asn Asn Phe Gly Leu Asp Leu Lys Ala
     2450                2455                2460
Asp Asp Lys Ile Tyr Phe Gly Gly Leu Pro Thr Leu Arg Asn Leu Ser
2465                2470                2475                2480
Met Lys Ala Arg Pro Glu Val Asn Leu Lys Lys Tyr Ser Gly Cys Leu
                 2485                2490                2495
Lys Asp Ile Glu Ile Ser Arg Thr Pro Tyr Asn Ile Leu Ser Ser Pro
             2500                2505                2510
Asp Tyr Val Gly Val Thr Lys Gly Cys Ser Leu Glu Asn Val Tyr Thr
         2515                2520                2525
Val Ser Phe Pro Lys Pro Gly Phe Val Glu Leu Ser Pro Val Pro Ile
     2530                2535                2540
Asp Val Gly Thr Glu Ile Asn Leu Ser Phe Ser Thr Lys Asn Glu Ser
2545                2550                2555                2560
Gly Ile Ile Leu Leu Gly Ser Gly Gly Thr Pro Ala Pro Pro Arg Arg
                 2565                2570                2575
Lys Arg Arg Gln Thr Gly Gln Ala Tyr Tyr Val Ile Leu Leu Asn Arg
             2580                2585                2590
Gly Arg Leu Glu Val His Leu Ser Thr Gly Ala Arg Thr Met Arg Lys
         2595                2600                2605
Ile Val Ile Arg Pro Glu Pro Asn Leu Phe His Asp Gly Arg Glu His
     2610                2615                2620
Ser Val His Val Glu Arg Thr Arg Gly Ile Phe Thr Val Gln Val Asp
2625                2630                2635                2640
Glu Asn Arg Arg Tyr Met Gln Asn Leu Thr Val Glu Gln Pro Ile Glu
                 2645                2650                2655
Val Lys Lys Leu Phe Val Gly Gly Ala Pro Pro Glu Phe Gln Pro Ser
             2660                2665                2670
```

```
Pro Leu Arg Asn Ile Pro Pro Phe Glu Gly Cys Ile Trp Asn Leu Val
        2675                2680                2685
Ile Asn Ser Val Pro Met Asp Phe Ala Arg Pro Val Ser Phe Lys Asn
        2690                2695                2700
Ala Asp Ile Gly Arg Cys Ala His Gln Lys Leu Arg Glu Asp Glu Asp
2705                2710                2715                2720
Gly Ala Ala Pro Ala Glu Ile Val Ile Gln Pro Glu Pro Val Pro Thr
            2725                2730                2735
Pro Ala Phe Pro Thr Pro Thr Pro Val Leu Thr His Gly Pro Cys Ala
            2740                2745                2750
Ala Glu Ser Glu Pro Ala Leu Leu Ile Gly Ser Lys Gln Phe Gly Leu
            2755                2760                2765
Ser Arg Asn Ser His Ile Ala Ile Ala Phe Asp Asp Thr Lys Val Lys
            2770                2775                2780
Asn Arg Leu Thr Ile Glu Leu Glu Val Arg Thr Glu Ala Glu Ser Gly
2785                2790                2795                2800
Leu Leu Phe Tyr Met Ala Ala Ile Asn His Ala Asp Phe Ala Thr Val
            2805                2810                2815
Gln Leu Arg Asn Gly Leu Pro Tyr Phe Ser Tyr Asp Leu Gly Ser Gly
            2820                2825                2830
Asp Thr His Thr Met Ile Pro Thr Lys Ile Asn Asp Gly Gln Trp His
            2835                2840                2845
Lys Ile Lys Ile Met Arg Ser Lys Gln Glu Gly Ile Leu Tyr Val Asp
            2850                2855                2860
Gly Ala Ser Asn Arg Thr Ile Ser Pro Lys Lys Ala Asp Ile Leu Asp
2865                2870                2875                2880
Val Val Gly Met Leu Tyr Val Gly Gly Leu Pro Ile Asn Tyr Thr Thr
            2885                2890                2895
Arg Arg Ile Gly Pro Val Thr Tyr Ser Ile Asp Gly Cys Val Arg Asn
            2900                2905                2910
Leu His Met Ala Glu Ala Pro Ala Asp Leu Glu Gln Pro Thr Ser Ser
            2915                2920                2925
Phe His Val Gly Thr Cys Phe Ala Asn Ala Gln Arg Gly Thr Tyr Phe
    2930                2935                2940
Asp Gly Thr Gly Phe Ala Lys Ala Val Gly Gly Phe Lys Val Gly Leu
2945                2950                2955                2960
Asp Leu Leu Val Glu Phe Glu Phe Ala Thr Thr Thr Thr Thr Gly Val
                2965                2970                2975
Leu Leu Gly Ile Ser Ser Gln Lys Met Asp Gly Met Gly Ile Glu Met
            2980                2985                2990
Ile Asp Glu Lys Leu Met Phe His Val Asp Asn Gly Ala Gly Arg Phe
        2995                3000                3005
Thr Ala Val Tyr Asp Ala Gly Val Pro Gly His Leu Cys Asp Gly Gln
        3010                3015                3020
Trp His Lys Val Thr Ala Asn Leu Lys His Arg Ile Glu Leu Thr
3025                3030                3035                3040
Val Asp Gly Asn Gln Val Glu Ala Gln Ser Pro Asn Pro Ala Ser Thr
                3045                3050                3055
Ser Ala Asp Thr Asn Asp Pro Val Phe Val Gly Gly Phe Pro Asp Asp
            3060                3065                3070
Leu Lys Gln Phe Gly Leu Thr Thr Ser Ile Pro Phe Arg Gly Cys Ile
        3075                3080                3085
```

-continued

```
Arg Ser Leu Lys Leu Thr Lys Gly Thr Ala Ser His Trp Arg Leu Ile
    3090                3095                3100
Leu Pro Arg Pro Trp Asn
3105            3110

<210> SEQ ID NO 8
<211> LENGTH: 9534
<212> TYPE: DNA
<213> ORGANISM: Homo sapiens
<220> FEATURE:
<221> NAME/KEY: CDS
<222> LOCATION: (50)...(9382)

<400> SEQUENCE: 8
cagcgactcc tctggctccc gagaagtgga tccggtcgcg gccactacg atg ccg gga      58
                                                     Met Pro Gly
                                                       1 gcc gcc ggg gtc ctc ctc ctt ctg ctg ctc tcc gga ggc ctc ggg ggc      106
Ala Ala Gly Val Leu Leu Leu Leu Leu Leu Ser Gly Gly Leu Gly Gly
      5                  10                  15 gta cag gcg cag cgg ccg cag cag cag cgg cag tca cag gca cat cag      154
Val Gln Ala Gln Arg Pro Gln Gln Gln Arg Gln Ser Gln Ala His Gln
 20                  25                  30                  35 caa aga ggt tta ttc cct gct gtc ctg aat ctt gct tct aat gct ctt      202
Gln Arg Gly Leu Phe Pro Ala Val Leu Asn Leu Ala Ser Asn Ala Leu
                 40                  45                  50 atc acg acc aat gca aca tgt gga gaa aaa gga cct gaa atg tac tgc      250
Ile Thr Thr Asn Ala Thr Cys Gly Glu Lys Gly Pro Glu Met Tyr Cys
             55                  60                  65 aaa ttg gta gaa cat gtc cct ggg cag cct gtg agg aac ccg cag tgt      298
Lys Leu Val Glu His Val Pro Gly Gln Pro Val Arg Asn Pro Gln Cys
         70                  75                  80 cga atc tgc aat caa aac agc agc aat cca aac cag aga cac ccg att      346
Arg Ile Cys Asn Gln Asn Ser Ser Asn Pro Asn Gln Arg His Pro Ile
     85                  90                  95 aca aat gct att gat gga aag aac act tgg tgg cag agt ccc agt att      394
Thr Asn Ala Ile Asp Gly Lys Asn Thr Trp Trp Gln Ser Pro Ser Ile
100                 105                 110                 115 aag aat gga atc gaa tac cat tat gtg aca att aca ctg gat tta cag      442
Lys Asn Gly Ile Glu Tyr His Tyr Val Thr Ile Thr Leu Asp Leu Gln
                120                 125                 130 cag gtg ttc cag atc gcg tat gtg att gtg aag gca gct aac tcc ccc      490
Gln Val Phe Gln Ile Ala Tyr Val Ile Val Lys Ala Ala Asn Ser Pro
            135                 140                 145 cgg cct gga aac tgg att ttg gaa cgc tct ctt gat gat gtt gaa tac      538
Arg Pro Gly Asn Trp Ile Leu Glu Arg Ser Leu Asp Asp Val Glu Tyr
        150                 155                 160 aag ccc tgg cag tat cat gct gtg aca gac acg gag tgc cta acg ctt      586
Lys Pro Trp Gln Tyr His Ala Val Thr Asp Thr Glu Cys Leu Thr Leu
    165                 170                 175 tac aat att tat ccc cgc act ggg cca ccg tca tat gcc aaa gat gat      634
Tyr Asn Ile Tyr Pro Arg Thr Gly Pro Pro Ser Tyr Ala Lys Asp Asp
180                 185                 190                 195 gag gtc atc tgc act tca ttt tac tcc aag ata cac cct tta gaa aat      682
Glu Val Ile Cys Thr Ser Phe Tyr Ser Lys Ile His Pro Leu Glu Asn
                200                 205                 210 gga gag att cac atc tct tta atc aat ggg aga cca agt gcc gat gat      730
Gly Glu Ile His Ile Ser Leu Ile Asn Gly Arg Pro Ser Ala Asp Asp
            215                 220                 225 cct tct cca gaa ctg cta gaa ttt acc tcc gct cgc tat att cgc ctg      778
Pro Ser Pro Glu Leu Leu Glu Phe Thr Ser Ala Arg Tyr Ile Arg Leu
```

-continued

```
          230                 235                 240
aga ttt cag agg atc cgc aca ctg aat gct gac ttg atg atg ttt gct     826
Arg Phe Gln Arg Ile Arg Thr Leu Asn Ala Asp Leu Met Met Phe Ala
    245                 250                 255 cac aaa gac cca aga gaa att gac ccc att gtc acc aga aga tat tac     874
His Lys Asp Pro Arg Glu Ile Asp Pro Ile Val Thr Arg Arg Tyr Tyr
260                 265                 270                 275 tac tcg gtc aag gat att tca gtt gga ggg atg tgc atc tgc tat ggt     922
Tyr Ser Val Lys Asp Ile Ser Val Gly Gly Met Cys Ile Cys Tyr Gly
                280                 285                 290 cat gcc agg gct tgt cca ctt gat cca gcg aca aat aaa tct cgc tgt     970
His Ala Arg Ala Cys Pro Leu Asp Pro Ala Thr Asn Lys Ser Arg Cys
                295                 300                 305 gag tgt gag cat aac aca tgt ggc gat agc tgt gat cag tgc tgt cca    1018
Glu Cys Glu His Asn Thr Cys Gly Asp Ser Cys Asp Gln Cys Cys Pro
            310                 315                 320 gga ttc cat cag aaa ccc tgg aga gct gga act ttt cta act aaa act    1066
Gly Phe His Gln Lys Pro Trp Arg Ala Gly Thr Phe Leu Thr Lys Thr
        325                 330                 335 gaa tgt gaa gca tgc aat tgt cat gga aaa gct gaa gaa tgc tat tat    1114
Glu Cys Glu Ala Cys Asn Cys His Gly Lys Ala Glu Glu Cys Tyr Tyr
340                 345                 350                 355 gat gaa aat gtt gcc aga aga aat ctg agt ttg aat ata cgt gga aag    1162
Asp Glu Asn Val Ala Arg Arg Asn Leu Ser Leu Asn Ile Arg Gly Lys
                360                 365                 370 tac att gga ggg ggt gtc tgc att aat tgt acc caa aac act gct ggt    1210
Tyr Ile Gly Gly Gly Val Cys Ile Asn Cys Thr Gln Asn Thr Ala Gly
                375                 380                 385 ata aac tgc gag aca tgt aca gat ggc ttc ttc aga ccc aaa ggg gta    1258
Ile Asn Cys Glu Thr Cys Thr Asp Gly Phe Phe Arg Pro Lys Gly Val
            390                 395                 400 tct cca aat tat cca agg cca tgc cag cca tgt cat tgc gat cca att    1306
Ser Pro Asn Tyr Pro Arg Pro Cys Gln Pro Cys His Cys Asp Pro Ile
        405                 410                 415 ggt tcc tta aat gaa gtc tgt gtc aag gat gag aaa cat gct cga cga    1354
Gly Ser Leu Asn Glu Val Cys Val Lys Asp Glu Lys His Ala Arg Arg
420                 425                 430                 435 ggt ttg gca cct gga tcc tgt cat tgc aaa act ggt ttt gga ggt gtg    1402
Gly Leu Ala Pro Gly Ser Cys His Cys Lys Thr Gly Phe Gly Gly Val
                440                 445                 450 agc tgt gat cgg tgt gcc agg ggc tac act ggc tac ccg gac tgc aaa    1450
Ser Cys Asp Arg Cys Ala Arg Gly Tyr Thr Gly Tyr Pro Asp Cys Lys
                455                 460                 465 gcc tgt aac tgc agt ggg tta ggg agc aaa aat gag gat cct tgt ttt    1498
Ala Cys Asn Cys Ser Gly Leu Gly Ser Lys Asn Glu Asp Pro Cys Phe
            470                 475                 480 ggc ccc tgt atc tgc aag gaa aat gtt gaa gga gga gac tgt agt cgt    1546
Gly Pro Cys Ile Cys Lys Glu Asn Val Glu Gly Gly Asp Cys Ser Arg
        485                 490                 495 tgc aaa tcc ggc ttc ttc aat ttg caa gag gat aat tgg aaa ggc tgc    1594
Cys Lys Ser Gly Phe Phe Asn Leu Gln Glu Asp Asn Trp Lys Gly Cys
500                 505                 510                 515 gat gag tgt ttc tgt tca ggg gtt tca aac aga tgt cag agt tcc tac    1642
Asp Glu Cys Phe Cys Ser Gly Val Ser Asn Arg Cys Gln Ser Ser Tyr
                520                 525                 530 tgg acc tat ggc aaa ata caa gat atg agt ggc tgg tat ctg act gac    1690
Trp Thr Tyr Gly Lys Ile Gln Asp Met Ser Gly Trp Tyr Leu Thr Asp
                535                 540                 545 ctt cct ggc cgc att cga gtg gct ccc cag cag gac gac ttg gac tca    1738
```

```
Leu Pro Gly Arg Ile Arg Val Ala Pro Gln Gln Asp Leu Asp Ser
            550                 555                 560 cct cag cag atc agc atc agt aac gcg gag gcc cgg caa gcc ctg ccg    1786
Pro Gln Gln Ile Ser Ile Ser Asn Ala Glu Ala Arg Gln Ala Leu Pro
565                 570                 575 cac agc tac tac tgg agc gcg ccg gct ccc tat ctg gga aac aaa ctc    1834
His Ser Tyr Tyr Trp Ser Ala Pro Ala Pro Tyr Leu Gly Asn Lys Leu
580                 585                 590                 595 cca gca gta gga gga cag ttg aca ttt acc ata tca tat gac ctt gaa    1882
Pro Ala Val Gly Gly Gln Leu Thr Phe Thr Ile Ser Tyr Asp Leu Glu
                600                 605                 610 gaa gag gaa gaa gat aca gaa cgt gtt ctc cag ctt atg att atc tta    1930
Glu Glu Glu Glu Asp Thr Glu Arg Val Leu Gln Leu Met Ile Ile Leu
            615                 620                 625 gag ggt aat gac ttg agc atc agc aca gcc caa gat gag gtg tac ctg    1978
Glu Gly Asn Asp Leu Ser Ile Ser Thr Ala Gln Asp Glu Val Tyr Leu
            630                 635                 640 cac cca tct gaa gaa cat act aat gta ttg tta ctt aaa gaa gaa tca    2026
His Pro Ser Glu Glu His Thr Asn Val Leu Leu Leu Lys Glu Glu Ser
            645                 650                 655 ttt acc ata cat ggc aca cat ttt cca gtc cgt aga aag gaa ttt atg    2074
Phe Thr Ile His Gly Thr His Phe Pro Val Arg Arg Lys Glu Phe Met
660                 665                 670                 675 aca gtg ctt gcg aat ttg aag aga gtc ctc cta caa atc aca tac agc    2122
Thr Val Leu Ala Asn Leu Lys Arg Val Leu Leu Gln Ile Thr Tyr Ser
                680                 685                 690 ttt ggg atg gat gcc atc ttc agg ttg agc tct gtt aac ctt gaa tcc    2170
Phe Gly Met Asp Ala Ile Phe Arg Leu Ser Ser Val Asn Leu Glu Ser
            695                 700                 705 gct gtc tcc tat cct act gat gga agc att gca gca gct gta gaa gtg    2218
Ala Val Ser Tyr Pro Thr Asp Gly Ser Ile Ala Ala Ala Val Glu Val
            710                 715                 720 tgt cag tgc cca cca ggg tat act ggc tcc tct tgt gaa tct tgt tgg    2266
Cys Gln Cys Pro Pro Gly Tyr Thr Gly Ser Ser Cys Glu Ser Cys Trp
725                 730                 735 cct agg cac agg cga gtt aac ggc act att ttt ggt ggc atc tgt gag    2314
Pro Arg His Arg Arg Val Asn Gly Thr Ile Phe Gly Gly Ile Cys Glu
740                 745                 750                 755 cca tgt cag tgc ttt ggt cat gcg gag tcc tgt gat gac gtc act gga    2362
Pro Cys Gln Cys Phe Gly His Ala Glu Ser Cys Asp Asp Val Thr Gly
                760                 765                 770 gaa tgc ctg aac tgt aag gat cac aca ggt ggc cca tat tgt gat aaa    2410
Glu Cys Leu Asn Cys Lys Asp His Thr Gly Gly Pro Tyr Cys Asp Lys
            775                 780                 785 tgt ctt cct ggt ttc tat ggc gag cct act aaa gga acc tct gaa gac    2458
Cys Leu Pro Gly Phe Tyr Gly Glu Pro Thr Lys Gly Thr Ser Glu Asp
            790                 795                 800 tgt caa ccc tgt gcc tgt cca ctc aat atc cca tcc aat aac ttt agc    2506
Cys Gln Pro Cys Ala Cys Pro Leu Asn Ile Pro Ser Asn Asn Phe Ser
805                 810                 815 cca acg tgc cat tta gac cgg agt ctt gga ttg atc tgt gat gga tgc    2554
Pro Thr Cys His Leu Asp Arg Ser Leu Gly Leu Ile Cys Asp Gly Cys
820                 825                 830                 835 cct gtc ggg tac aca gga cca cgc tgt gag agg tgt gca gaa ggc tat    2602
Pro Val Gly Tyr Thr Gly Pro Arg Cys Glu Arg Cys Ala Glu Gly Tyr
                840                 845                 850 ttt gga caa ccc tct gta cct gga gga tca tgt cag cca tgc caa tgc    2650
Phe Gly Gln Pro Ser Val Pro Gly Gly Ser Cys Gln Pro Cys Gln Cys
            855                 860                 865
```

-continued

```
aat gac aac ctt gac ttc tcc atc cct ggc agc tgt gac agc ttg tct      2698
Asn Asp Asn Leu Asp Phe Ser Ile Pro Gly Ser Cys Asp Ser Leu Ser
            870                 875                 880 ggc tcc tgt ctg ata tgt aaa cca ggt aca aca ggc cgg tac tgt gag      2746
Gly Ser Cys Leu Ile Cys Lys Pro Gly Thr Thr Gly Arg Tyr Cys Glu
885                 890                 895 ctc tgt gct gat gga tat ttt gga gat gca gtt gat gcg aag aac tgt      2794
Leu Cys Ala Asp Gly Tyr Phe Gly Asp Ala Val Asp Ala Lys Asn Cys
900                 905                 910                 915 cag ccc tgt cgc tgt aat gcc ggt ggc tct ttc tct gag gtt tgc cac      2842
Gln Pro Cys Arg Cys Asn Ala Gly Gly Ser Phe Ser Glu Val Cys His
            920                 925                 930 agt caa act gga cag tgt gag tgc aga gcc aac gtt cag ggt cag aga      2890
Ser Gln Thr Gly Gln Cys Glu Cys Arg Ala Asn Val Gln Gly Gln Arg
            935                 940                 945 tgt gac aaa tgc aag gct ggg acc ttt ggc cta caa tca gca agg ggc      2938
Cys Asp Lys Cys Lys Ala Gly Thr Phe Gly Leu Gln Ser Ala Arg Gly
            950                 955                 960 tgt gtt ccc tgc aac tgc aat tct ttt ggg tct aag tca ttc gac tgt      2986
Cys Val Pro Cys Asn Cys Asn Ser Phe Gly Ser Lys Ser Phe Asp Cys
965                 970                 975 gaa gag agt gga caa tgt tgg tgc caa cct gga gtc aca ggg aag aaa      3034
Glu Glu Ser Gly Gln Cys Trp Cys Gln Pro Gly Val Thr Gly Lys Lys
980                 985                 990                 995 tgt gac cgc tgt gcc cac ggc tat ttc aac ttc caa gaa gga ggc tgc      3082
Cys Asp Arg Cys Ala His Gly Tyr Phe Asn Phe Gln Glu Gly Gly Cys
                    1000                1005                1010 aca gct tgt gaa tgt tct cat ctg ggt aat aat tgt gac cca aag act      3130
Thr Ala Cys Glu Cys Ser His Leu Gly Asn Asn Cys Asp Pro Lys Thr
            1015                1020                1025 ggg cga tgc att tgc cca ccc aat acc att gga gag aaa tgt tct aaa      3178
Gly Arg Cys Ile Cys Pro Pro Asn Thr Ile Gly Glu Lys Cys Ser Lys
            1030                1035                1040 tgt gca ccc aat acc tgg ggc cac agc att acc act ggt tgt aag gct      3226
Cys Ala Pro Asn Thr Trp Gly His Ser Ile Thr Thr Gly Cys Lys Ala
            1045                1050                1055 tgt aac tgc agc aca gtg gga tcc ttg gat ttc caa tgc aat gta aat      3274
Cys Asn Cys Ser Thr Val Gly Ser Leu Asp Phe Gln Cys Asn Val Asn
1060                1065                1070                1075 aca ggc caa tgc aac tgt cat cca aaa ttc tct ggt gca aaa tgt aca      3322
Thr Gly Gln Cys Asn Cys His Pro Lys Phe Ser Gly Ala Lys Cys Thr
            1080                1085                1090 gag tgc agt cga ggt cac tgg aac tac cct cgc tgc aat ctc tgt gac      3370
Glu Cys Ser Arg Gly His Trp Asn Tyr Pro Arg Cys Asn Leu Cys Asp
            1095                1100                1105 tgc ttc ctc cct ggg aca gat gcc aca acc tgt gat tca gag act aaa      3418
Cys Phe Leu Pro Gly Thr Asp Ala Thr Thr Cys Asp Ser Glu Thr Lys
            1110                1115                1120 aaa tgc tcc tgt agt gat caa act ggg cag tgc act tgt aag gtg aat      3466
Lys Cys Ser Cys Ser Asp Gln Thr Gly Gln Cys Thr Cys Lys Val Asn
            1125                1130                1135 gtg gaa ggc atc cac tgt gac aga tgc cgg cct ggc aaa ttc gga ctc      3514
Val Glu Gly Ile His Cys Asp Arg Cys Arg Pro Gly Lys Phe Gly Leu
1140                1145                1150                1155 gat gcc aag aat cca ctt ggc tgc agc agc tgt tat tgc ttc ggc act      3562
Asp Ala Lys Asn Pro Leu Gly Cys Ser Ser Cys Tyr Cys Phe Gly Thr
            1160                1165                1170 act acc cag tgc tct gaa gca aaa gga ctg atc cgg acg tgg gtg act      3610
Thr Thr Gln Cys Ser Glu Ala Lys Gly Leu Ile Arg Thr Trp Val Thr
            1175                1180                1185
```

```
ctg aag gct gag cag acc att cta ccc ctg gta gat gag gct ctg cag      3658
Leu Lys Ala Glu Gln Thr Ile Leu Pro Leu Val Asp Glu Ala Leu Gln
        1190                1195                1200 cac acg acc acc aag ggc att gtt ttt caa cat cca gag att gtt gcc      3706
His Thr Thr Thr Lys Gly Ile Val Phe Gln His Pro Glu Ile Val Ala
1205                1210                1215 cac atg gac ctg atg aga gaa gat ctc cat ttg gaa cct ttt tat tgg      3754
His Met Asp Leu Met Arg Glu Asp Leu His Leu Glu Pro Phe Tyr Trp
1220                1225                1230                1235 aaa ctt cca gaa caa ttt gaa gga aag aag ttg atg gcc tat ggg ggc      3802
Lys Leu Pro Glu Gln Phe Glu Gly Lys Lys Leu Met Ala Tyr Gly Gly
            1240                1245                1250 aaa ctc aag tat gca atc tat ttc gag gct cgg gaa gaa aca ggt ttc      3850
Lys Leu Lys Tyr Ala Ile Tyr Phe Glu Ala Arg Glu Glu Thr Gly Phe
                1255                1260                1265 tct aca tat aat cct caa gtg atc att cga ggt ggg aca cct act cat      3898
Ser Thr Tyr Asn Pro Gln Val Ile Ile Arg Gly Gly Thr Pro Thr His
            1270                1275                1280 gct aga att atc gtc agg cat atg gct gct cct ctg att ggc caa ttg      3946
Ala Arg Ile Ile Val Arg His Met Ala Ala Pro Leu Ile Gly Gln Leu
        1285                1290                1295 aca agg cat gaa att gaa atg aca gag aaa gaa tgg aaa tat tat ggg      3994
Thr Arg His Glu Ile Glu Met Thr Glu Lys Glu Trp Lys Tyr Tyr Gly
1300                1305                1310                1315 gat gat cct cga gtc cat aga act gtg acc cga gaa gac ttc ttg gat      4042
Asp Asp Pro Arg Val His Arg Thr Val Thr Arg Glu Asp Phe Leu Asp
            1320                1325                1330 ata cta tat gat att cat tac att ctt atc aaa gct act tat gga aat      4090
Ile Leu Tyr Asp Ile His Tyr Ile Leu Ile Lys Ala Thr Tyr Gly Asn
                1335                1340                1345 ttc atg cga caa agc agg att tct gaa atc tca atg gag gta gct gaa      4138
Phe Met Arg Gln Ser Arg Ile Ser Glu Ile Ser Met Glu Val Ala Glu
        1350                1355                1360 caa gga cgt gga aca aca atg act cct cca gct gac ttg att gaa aaa      4186
Gln Gly Arg Gly Thr Thr Met Thr Pro Pro Ala Asp Leu Ile Glu Lys
1365                1370                1375 tgt gat tgt ccc ctg ggc tat tct ggc ctg tcc tgt gag gca tgc ttg      4234
Cys Asp Cys Pro Leu Gly Tyr Ser Gly Leu Ser Cys Glu Ala Cys Leu
1380                1385                1390                1395 ccg gga ttt tat cga ctg cgt tct caa cca ggt ggc cgc acc cct gga      4282
Pro Gly Phe Tyr Arg Leu Arg Ser Gln Pro Gly Gly Arg Thr Pro Gly
            1400                1405                1410 cca acc ctg ggc acc tgt gtt cca tgt caa tgt aat gga cac agc agc      4330
Pro Thr Leu Gly Thr Cys Val Pro Cys Gln Cys Asn Gly His Ser Ser
        1415                1420                1425 ctg tgt gac cct gaa aca tcg ata tgc cag aat tgt caa cat cac act      4378
Leu Cys Asp Pro Glu Thr Ser Ile Cys Gln Asn Cys Gln His His Thr
        1430                1435                1440 gct ggt gac ttc tgt gaa cga tgt gct ctt gga tac tat gga att gtc      4426
Ala Gly Asp Phe Cys Glu Arg Cys Ala Leu Gly Tyr Tyr Gly Ile Val
1445                1450                1455 aag gga ttg cca aat gac tgt cag caa tgt gcc tgc cct ctg att tct      4474
Lys Gly Leu Pro Asn Asp Cys Gln Gln Cys Ala Cys Pro Leu Ile Ser
        1460                1465                1470                1475 tcc agt aac aat ttc agc ccc tct tgt gtc gca gaa gga ctt gac gac      4522
Ser Ser Asn Asn Phe Ser Pro Ser Cys Val Ala Glu Gly Leu Asp Asp
            1480                1485                1490 tac cgc tgc acg gct tgt cca cgg gga tat gaa ggc cag tac tgt gaa      4570
Tyr Arg Cys Thr Ala Cys Pro Arg Gly Tyr Glu Gly Gln Tyr Cys Glu
```

-continued

|  |  |  | 1495 |  |  |  | 1500 |  |  |  | 1505 |  |  |  |  |
|---|---|---|---|---|---|---|---|---|---|---|---|---|---|---|---|
| agg | tgt | gcc | cct | ggc | tat | act | ggc | agt | cca | ggc | aac | cct | gga | ggc | tcc | 4618 |
| Arg | Cys | Ala | Pro | Gly | Tyr | Thr | Gly | Ser | Pro | Gly | Asn | Pro | Gly | Gly | Ser |  |
|  | 1510 |  |  |  | 1515 |  |  |  | 1520 |  |  |  |  |  |  |

| tgc | caa | gaa | tgt | gag | tgt | gat | ccc | tat | ggc | tca | ctg | cct | gtg | ccc | tgt | 4666 |
| Cys | Gln | Glu | Cys | Glu | Cys | Asp | Pro | Tyr | Gly | Ser | Leu | Pro | Val | Pro | Cys |  |
| 1525 |  |  |  |  | 1530 |  |  |  |  | 1535 |  |  |  |  |  |  |

| gac | cct | gtc | aca | gga | ttc | tgc | acg | tgc | cga | cct | gga | gcc | acg | gga | agg | 4714 |
| Asp | Pro | Val | Thr | Gly | Phe | Cys | Thr | Cys | Arg | Pro | Gly | Ala | Thr | Gly | Arg |  |
| 1540 |  |  |  |  | 1545 |  |  |  |  | 1550 |  |  |  |  | 1555 |  |

| aag | tgt | gac | ggc | tgc | aag | cac | tgg | cat | gca | cgc | gag | ggc | tgg | gag | tgt | 4762 |
| Lys | Cys | Asp | Gly | Cys | Lys | His | Trp | His | Ala | Arg | Glu | Gly | Trp | Glu | Cys |  |
|  |  |  | 1560 |  |  |  | 1565 |  |  |  | 1570 |  |  |  |  |  |

| gtt | ttt | tgt | gga | gat | gag | tgc | act | ggc | ctt | ctt | ctc | ggt | gac | ttg | gct | 4810 |
| Val | Phe | Cys | Gly | Asp | Glu | Cys | Thr | Gly | Leu | Leu | Leu | Gly | Asp | Leu | Ala |  |
|  |  | 1575 |  |  |  | 1580 |  |  |  |  | 1585 |  |  |  |  |  |

| cgc | ctg | gag | cag | atg | gtc | atg | agc | atc | aac | ctc | act | ggt | ccg | ctg | cct | 4858 |
| Arg | Leu | Glu | Gln | Met | Val | Met | Ser | Ile | Asn | Leu | Thr | Gly | Pro | Leu | Pro |  |
|  | 1590 |  |  |  | 1595 |  |  |  |  | 1600 |  |  |  |  |  |  |

| gcg | cca | tat | aaa | atg | ctg | tat | ggt | ctt | gaa | aat | atg | act | cag | gag | cta | 4906 |
| Ala | Pro | Tyr | Lys | Met | Leu | Tyr | Gly | Leu | Glu | Asn | Met | Thr | Gln | Glu | Leu |  |
| 1605 |  |  |  |  | 1610 |  |  |  |  | 1615 |  |  |  |  |  |  |

| aag | cac | ttg | ctg | tca | cct | cag | cgg | gcc | cca | gag | agg | ctt | att | cag | ctg | 4954 |
| Lys | His | Leu | Leu | Ser | Pro | Gln | Arg | Ala | Pro | Glu | Arg | Leu | Ile | Gln | Leu |  |
| 1620 |  |  |  |  | 1625 |  |  |  |  | 1630 |  |  |  |  | 1635 |  |

| gca | gag | ggc | aat | ctg | aat | aca | ctc | gtg | acc | gaa | atg | aac | gag | ctg | ctg | 5002 |
| Ala | Glu | Gly | Asn | Leu | Asn | Thr | Leu | Val | Thr | Glu | Met | Asn | Glu | Leu | Leu |  |
|  |  |  | 1640 |  |  |  | 1645 |  |  |  | 1650 |  |  |  |  |  |

| acc | agg | gct | acc | aaa | gtg | aca | gca | gat | ggc | gag | cag | acc | gga | cag | gat | 5050 |
| Thr | Arg | Ala | Thr | Lys | Val | Thr | Ala | Asp | Gly | Glu | Gln | Thr | Gly | Gln | Asp |  |
|  |  | 1655 |  |  |  | 1660 |  |  |  |  | 1665 |  |  |  |  |  |

| gct | gag | agg | acc | aac | aca | aga | gca | aag | tcc | ctg | gga | gaa | ttc | att | aag | 5098 |
| Ala | Glu | Arg | Thr | Asn | Thr | Arg | Ala | Lys | Ser | Leu | Gly | Glu | Phe | Ile | Lys |  |
|  | 1670 |  |  |  | 1675 |  |  |  |  | 1680 |  |  |  |  |  |  |

| gag | ctt | gcc | cgg | gat | gca | gaa | gct | gta | aat | gaa | aaa | gct | ata | aaa | cta | 5146 |
| Glu | Leu | Ala | Arg | Asp | Ala | Glu | Ala | Val | Asn | Glu | Lys | Ala | Ile | Lys | Leu |  |
| 1685 |  |  |  |  | 1690 |  |  |  |  | 1695 |  |  |  |  |  |  |

| aat | gaa | act | cta | gga | act | cga | gac | gag | gcc | ttt | gag | aga | aat | ttg | gaa | 5194 |
| Asn | Glu | Thr | Leu | Gly | Thr | Arg | Asp | Glu | Ala | Phe | Glu | Arg | Asn | Leu | Glu |  |
| 1700 |  |  |  |  | 1705 |  |  |  |  | 1710 |  |  |  |  | 1715 |  |

| ggg | ctt | cag | aaa | gag | att | gac | cag | atg | att | aaa | gaa | ctg | agg | agg | aaa | 5242 |
| Gly | Leu | Gln | Lys | Glu | Ile | Asp | Gln | Met | Ile | Lys | Glu | Leu | Arg | Arg | Lys |  |
|  |  |  | 1720 |  |  |  | 1725 |  |  |  | 1730 |  |  |  |  |  |

| aat | cta | gag | aca | caa | aag | gaa | att | gct | gaa | gat | gag | ttg | gta | gct | gca | 5290 |
| Asn | Leu | Glu | Thr | Gln | Lys | Glu | Ile | Ala | Glu | Asp | Glu | Leu | Val | Ala | Ala |  |
|  |  | 1735 |  |  |  | 1740 |  |  |  |  | 1745 |  |  |  |  |  |

| gaa | gcc | ctt | ctg | aaa | aaa | gtg | aag | aag | ctg | ttt | gga | gag | tcc | cgg | ggg | 5338 |
| Glu | Ala | Leu | Leu | Lys | Lys | Val | Lys | Lys | Leu | Phe | Gly | Glu | Ser | Arg | Gly |  |
|  |  | 1750 |  |  |  | 1755 |  |  |  |  | 1760 |  |  |  |  |  |

| gaa | aat | gaa | gaa | atg | gag | aag | gat | ctc | cgg | gaa | aaa | ctg | gct | gac | tac | 5386 |
| Glu | Asn | Glu | Glu | Met | Glu | Lys | Asp | Leu | Arg | Glu | Lys | Leu | Ala | Asp | Tyr |  |
|  |  | 1765 |  |  |  | 1770 |  |  |  |  | 1775 |  |  |  |  |  |

| aaa | aac | aaa | gtt | gat | gat | gct | tgg | gac | ctt | ttg | aga | gaa | gcc | aca | gat | 5434 |
| Lys | Asn | Lys | Val | Asp | Asp | Ala | Trp | Asp | Leu | Leu | Arg | Glu | Ala | Thr | Asp |  |
| 1780 |  |  |  |  | 1785 |  |  |  |  | 1790 |  |  |  |  | 1795 |  |

| aaa | atc | aga | gaa | gct | aat | cgc | cta | ttt | gca | gta | aat | cag | aaa | aac | atg | 5482 |
| Lys | Ile | Arg | Glu | Ala | Asn | Arg | Leu | Phe | Ala | Val | Asn | Gln | Lys | Asn | Met |  |
|  |  |  | 1800 |  |  |  | 1805 |  |  |  | 1810 |  |  |  |  |  |

| act | gca | ttg | gag | aaa | aag | aag | gag | gct | gtt | gag | agc | ggc | aaa | cga | caa | 5530 |

```
Thr Ala Leu Glu Lys Lys Lys Glu Ala Val Glu Ser Gly Lys Arg Gln
         1815                1820                1825 att gag aac act tta aaa gaa ggc aat gac ata ctc gat gaa gcc aac     5578
Ile Glu Asn Thr Leu Lys Glu Gly Asn Asp Ile Leu Asp Glu Ala Asn
    1830                1835                1840 cgt ctt gca gat gaa atc aac tcc atc ata gac tat gtt gaa gac atc     5626
Arg Leu Ala Asp Glu Ile Asn Ser Ile Ile Asp Tyr Val Glu Asp Ile
1845                1850                1855 caa act aaa ttg cca cct atg tct gag gag ctt aat gat aaa ata gat     5674
Gln Thr Lys Leu Pro Pro Met Ser Glu Glu Leu Asn Asp Lys Ile Asp
1860                1865                1870                1875 gac ctc tcc caa gaa ata aag gac agg aag ctt gct gag aag gtg tcc     5722
Asp Leu Ser Gln Glu Ile Lys Asp Arg Lys Leu Ala Glu Lys Val Ser
                1880                1885                1890 cag gct gag agc cac gca gct cag ttg aat gac tca tct gct gtc ctt     5770
Gln Ala Glu Ser His Ala Ala Gln Leu Asn Asp Ser Ser Ala Val Leu
            1895                1900                1905 gat gga atc ctt gat gag gct aaa aac atc tcc ttc aat gcc act gca     5818
Asp Gly Ile Leu Asp Glu Ala Lys Asn Ile Ser Phe Asn Ala Thr Ala
        1910                1915                1920 gcc ttc aaa gct tac agc aat att aag gac tat att gat gaa gct gag     5866
Ala Phe Lys Ala Tyr Ser Asn Ile Lys Asp Tyr Ile Asp Glu Ala Glu
    1925                1930                1935 aaa gtt gcc aaa gaa gcc aaa gat ctt gca cat gaa gct aca aaa ctg     5914
Lys Val Ala Lys Glu Ala Lys Asp Leu Ala His Glu Ala Thr Lys Leu
1940                1945                1950                1955 gca aca ggt cct cgg ggt tta tta aag gaa gat gcc aaa ggc tgt ctt     5962
Ala Thr Gly Pro Arg Gly Leu Leu Lys Glu Asp Ala Lys Gly Cys Leu
                1960                1965                1970 cag aaa agc ttc agg att ctt aac gaa gcc aag aag tta gca aat gat     6010
Gln Lys Ser Phe Arg Ile Leu Asn Glu Ala Lys Lys Leu Ala Asn Asp
            1975                1980                1985 gta aaa gaa aat gaa gac cat cta aat ggc tta aaa acc agg ata gaa     6058
Val Lys Glu Asn Glu Asp His Leu Asn Gly Leu Lys Thr Arg Ile Glu
        1990                1995                2000 aat gct gat gct aga aat ggg gat ctc ttg aga act ttg aat gac act     6106
Asn Ala Asp Ala Arg Asn Gly Asp Leu Leu Arg Thr Leu Asn Asp Thr
    2005                2010                2015 ttg gga aag tta tca gct att cca aat gat aca gct gct aaa ctg caa     6154
Leu Gly Lys Leu Ser Ala Ile Pro Asn Asp Thr Ala Ala Lys Leu Gln
2020                2025                2030                2035 gct gtt aag gac aaa gcc aga caa gcc aac gac aca gct aaa gat gta     6202
Ala Val Lys Asp Lys Ala Arg Gln Ala Asn Asp Thr Ala Lys Asp Val
                2040                2045                2050 ctg gca cag att aca gag ctc cac cag aac ctc gat ggc ctg aag aag     6250
Leu Ala Gln Ile Thr Glu Leu His Gln Asn Leu Asp Gly Leu Lys Lys
            2055                2060                2065 aat tac aat aaa cta gca gac agc gtc gcc aaa acg aat gct gtg gtt     6298
Asn Tyr Asn Lys Leu Ala Asp Ser Val Ala Lys Thr Asn Ala Val Val
        2070                2075                2080 aaa gat cct tcc aag aac aaa atc att gcc gat gca gat gcc act gtc     6346
Lys Asp Pro Ser Lys Asn Lys Ile Ile Ala Asp Ala Asp Ala Thr Val
    2085                2090                2095 aaa aat tta gaa cag gaa gct gac cgg cta ata gat aaa ctc aaa ccc     6394
Lys Asn Leu Glu Gln Glu Ala Asp Arg Leu Ile Asp Lys Leu Lys Pro
2100                2105                2110                2115 atc aag gaa ctt gag gat aac cta aag aaa aac atc tct gag ata aag     6442
Ile Lys Glu Leu Glu Asp Asn Leu Lys Lys Asn Ile Ser Glu Ile Lys
                2120                2125                2130
```

| | |
|---|---|
| gaa ttg ata aac caa gct cgg aaa caa gcc aat tct atc aaa gta tct<br>Glu Leu Ile Asn Gln Ala Arg Lys Gln Ala Asn Ser Ile Lys Val Ser<br>            2135                      2140                      2145 | 6490 |
| gtg tct tca gga ggt gac tgc att cga aca tac aaa cca gaa atc aag<br>Val Ser Ser Gly Gly Asp Cys Ile Arg Thr Tyr Lys Pro Glu Ile Lys<br>            2150                      2155                      2160 | 6538 |
| aaa gga agt tac aat aat att gtt gtc aac gta aag aca gct gtt gct<br>Lys Gly Ser Tyr Asn Asn Ile Val Val Asn Val Lys Thr Ala Val Ala<br>2165                      2170                      2175 | 6586 |
| gat aac ctc ctc ttt tat ctt gga agt gcc aaa ttt att gac ttt ctg<br>Asp Asn Leu Leu Phe Tyr Leu Gly Ser Ala Lys Phe Ile Asp Phe Leu<br>2180                      2185                      2190                      2195 | 6634 |
| gct ata gaa atg cgt aaa ggc aaa gtc agc ttc ctc tgg gat gtt gga<br>Ala Ile Glu Met Arg Lys Gly Lys Val Ser Phe Leu Trp Asp Val Gly<br>            2200                      2205                      2210 | 6682 |
| tct gga gtt gga cgt gta gag tac cca gat ttg act att gat gac tca<br>Ser Gly Val Gly Arg Val Glu Tyr Pro Asp Leu Thr Ile Asp Asp Ser<br>            2215                      2220                      2225 | 6730 |
| tat tgg tac cgt atc gta gca tca aga act ggg aga aat gga act att<br>Tyr Trp Tyr Arg Ile Val Ala Ser Arg Thr Gly Arg Asn Gly Thr Ile<br>            2230                      2235                      2240 | 6778 |
| tct gtg aga gcc ctg gat gga ccc aaa gcc agc att gtg ccc agc aca<br>Ser Val Arg Ala Leu Asp Gly Pro Lys Ala Ser Ile Val Pro Ser Thr<br>            2245                      2250                      2255 | 6826 |
| cac cat tcg acg tct cct cca ggg tac acg att cta gat gtg gat gca<br>His His Ser Thr Ser Pro Pro Gly Tyr Thr Ile Leu Asp Val Asp Ala<br>2260                      2265                      2270                      2275 | 6874 |
| aat gca atg ctg ttt gtt ggt ggc ctg act ggg aaa tta aag aag gct<br>Asn Ala Met Leu Phe Val Gly Gly Leu Thr Gly Lys Leu Lys Lys Ala<br>            2280                      2285                      2290 | 6922 |
| gat gct gta cgt gtg att aca ttc act ggc tgc atg gga gaa aca tac<br>Asp Ala Val Arg Val Ile Thr Phe Thr Gly Cys Met Gly Glu Thr Tyr<br>            2295                      2300                      2305 | 6970 |
| ttt gac aac aaa cct ata ggt ttg tgg aat ttc cga gaa aaa gaa ggt<br>Phe Asp Asn Lys Pro Ile Gly Leu Trp Asn Phe Arg Glu Lys Glu Gly<br>            2310                      2315                      2320 | 7018 |
| gac tgc aaa gga tgc act gtc agt cct cag gtg gaa gat agt gag ggg<br>Asp Cys Lys Gly Cys Thr Val Ser Pro Gln Val Glu Asp Ser Glu Gly<br>2325                      2330                      2335 | 7066 |
| act att caa ttt gat gga gaa ggt tat gca ttg gtc agc cgt ccc att<br>Thr Ile Gln Phe Asp Gly Glu Gly Tyr Ala Leu Val Ser Arg Pro Ile<br>2340                      2345                      2350                      2355 | 7114 |
| cgc tgg tac ccc aac atc tcc act gtc atg ttc aag ttc aga aca ttt<br>Arg Trp Tyr Pro Asn Ile Ser Thr Val Met Phe Lys Phe Arg Thr Phe<br>            2360                      2365                      2370 | 7162 |
| tct tcg agt gct ctt ctg atg tat ctt gcc aca cga gac ctg aga gat<br>Ser Ser Ser Ala Leu Leu Met Tyr Leu Ala Thr Arg Asp Leu Arg Asp<br>            2375                      2380                      2385 | 7210 |
| ttc atg agt gtg gag ctc act gat ggg cac ata aaa gtc agt tac gat<br>Phe Met Ser Val Glu Leu Thr Asp Gly His Ile Lys Val Ser Tyr Asp<br>            2390                      2395                      2400 | 7258 |
| ctg ggc tca gga atg gct tcc gtt gtc agc aat caa aac cat aat gat<br>Leu Gly Ser Gly Met Ala Ser Val Val Ser Asn Gln Asn His Asn Asp<br>            2405                      2410                      2415 | 7306 |
| ggg aaa tgg aaa tca ttc act ctg tca aga att caa aaa caa gcc aat<br>Gly Lys Trp Lys Ser Phe Thr Leu Ser Arg Ile Gln Lys Gln Ala Asn<br>2420                      2425                      2430                      2435 | 7354 |
| ata tca att gta gat ata gat act aat cag gag gag aat ata gca act<br>Ile Ser Ile Val Asp Ile Asp Thr Asn Gln Glu Glu Asn Ile Ala Thr<br>            2440                      2445                      2450 | 7402 |

```
tcg tct tct gga aac aac ttt ggt ctt gac ttg aaa gca gat gac aaa      7450
Ser Ser Ser Gly Asn Asn Phe Gly Leu Asp Leu Lys Ala Asp Asp Lys
                2455                2460                2465 ata tat ttt ggt ggc ctg cca acg ctg aga aac ttg agt atg aaa gca      7498
Ile Tyr Phe Gly Gly Leu Pro Thr Leu Arg Asn Leu Ser Met Lys Ala
                2470                2475                2480 agg cca gaa gta aat ctg aag aaa tat tcc ggc tgc ctc aaa gat att      7546
Arg Pro Glu Val Asn Leu Lys Lys Tyr Ser Gly Cys Leu Lys Asp Ile
                2485                2490                2495 gaa att tca aga act ccg tac aat ata ctc agt agt ccc gat tat gtt      7594
Glu Ile Ser Arg Thr Pro Tyr Asn Ile Leu Ser Ser Pro Asp Tyr Val
2500                2505                2510                2515 ggt gtt acc aaa gga tgt tcc ctg gag aat gtt tac aca gtt agc ttt      7642
Gly Val Thr Lys Gly Cys Ser Leu Glu Asn Val Tyr Thr Val Ser Phe
                2520                2525                2530 cct aag cct ggt ttt gtg gag ctc tcc cct gtg cca att gat gta gga      7690
Pro Lys Pro Gly Phe Val Glu Leu Ser Pro Val Pro Ile Asp Val Gly
                2535                2540                2545 aca gaa atc aac ctg tca ttc agc acc aag aat gag tcc ggc atc att      7738
Thr Glu Ile Asn Leu Ser Phe Ser Thr Lys Asn Glu Ser Gly Ile Ile
                2550                2555                2560 ctt ttg gga agt gga ggg aca cca gca cca cct agg aga aaa cga agg      7786
Leu Leu Gly Ser Gly Gly Thr Pro Ala Pro Pro Arg Arg Lys Arg Arg
                2565                2570                2575 cag act gga cag gcc tat tat gta ata ctc ctc aac agg ggc cgt ctg      7834
Gln Thr Gly Gln Ala Tyr Tyr Val Ile Leu Leu Asn Arg Gly Arg Leu
2580                2585                2590                2595 gaa gtg cat ctc tcc aca ggg gca cga aca atg agg aaa att gtc atc      7882
Glu Val His Leu Ser Thr Gly Ala Arg Thr Met Arg Lys Ile Val Ile
                2600                2605                2610 aga cca gag ccg aat ctg ttt cat gat gga aga gaa cat tcc gtt cat      7930
Arg Pro Glu Pro Asn Leu Phe His Asp Gly Arg Glu His Ser Val His
                2615                2620                2625 gta gag cga act aga ggc atc ttt aca gtt caa gtg gat gaa aac aga      7978
Val Glu Arg Thr Arg Gly Ile Phe Thr Val Gln Val Asp Glu Asn Arg
                2630                2635                2640 aga tac atg caa aac ctg aca gtt gaa cag cct atc gaa gtt aaa aag      8026
Arg Tyr Met Gln Asn Leu Thr Val Glu Gln Pro Ile Glu Val Lys Lys
                2645                2650                2655 ctt ttc gtt ggg ggt gct cca cct gaa ttt caa cct tcc cca ctc aga      8074
Leu Phe Val Gly Gly Ala Pro Pro Glu Phe Gln Pro Ser Pro Leu Arg
2660                2665                2670                2675 aat att cct cct ttt gaa ggc tgc ata tgg aat ctt gtt att aac tct      8122
Asn Ile Pro Pro Phe Glu Gly Cys Ile Trp Asn Leu Val Ile Asn Ser
                2680                2685                2690 gtc ccc atg gac ttt gca agg cct gtg tcc ttc aaa aat gct gac att      8170
Val Pro Met Asp Phe Ala Arg Pro Val Ser Phe Lys Asn Ala Asp Ile
                2695                2700                2705 ggt cgc tgt gcc cat cag aaa ctc cgt gaa gat gaa gat gga gca gct      8218
Gly Arg Cys Ala His Gln Lys Leu Arg Glu Asp Glu Asp Gly Ala Ala
                2710                2715                2720 cca gct gaa ata gtt atc cag cct gag cca gtt ccc acc cca gcc ttt      8266
Pro Ala Glu Ile Val Ile Gln Pro Glu Pro Val Pro Thr Pro Ala Phe
                2725                2730                2735 cct acg ccc acc cca gtt ctg aca cat ggt cct tgt gct gca gaa tca      8314
Pro Thr Pro Thr Pro Val Leu Thr His Gly Pro Cys Ala Ala Glu Ser
2740                2745                2750                2755 gaa cca gct ctt ttg ata ggg agc aag cag ttc ggg ctt tca aga aac      8362
Glu Pro Ala Leu Leu Ile Gly Ser Lys Gln Phe Gly Leu Ser Arg Asn
```

```
                2760              2765              2770
agt cac att gca att gca ttt gat gac acc aaa gtt aaa aac cgt ctc      8410
Ser His Ile Ala Ile Ala Phe Asp Asp Thr Lys Val Lys Asn Arg Leu
        2775              2780              2785 aca att gag ttg gaa gta aga acc gaa gct gaa tcc ggc ttg ctt ttt      8458
Thr Ile Glu Leu Glu Val Arg Thr Glu Ala Glu Ser Gly Leu Leu Phe
        2790              2795              2800 tac atg gct gcg atc aat cat gct gat ttt gca aca gtt cag ctg aga      8506
Tyr Met Ala Ala Ile Asn His Ala Asp Phe Ala Thr Val Gln Leu Arg
        2805              2810              2815 aat gga ttg ccc tac ttc agc tat gac ttg ggg agt ggg gac acc cac      8554
Asn Gly Leu Pro Tyr Phe Ser Tyr Asp Leu Gly Ser Gly Asp Thr His
2820              2825              2830              2835 acc atg atc ccc acc aaa atc aat gat ggc cag tgg cac aag att aag      8602
Thr Met Ile Pro Thr Lys Ile Asn Asp Gly Gln Trp His Lys Ile Lys
                2840              2845              2850 ata atg aga agt aag caa gaa gga att ctt tat gta gat ggg gct tcc      8650
Ile Met Arg Ser Lys Gln Glu Gly Ile Leu Tyr Val Asp Gly Ala Ser
        2855              2860              2865 aac aga acc atc agt ccc aaa aaa gcc gac atc ctg gat gtc gtg gga      8698
Asn Arg Thr Ile Ser Pro Lys Lys Ala Asp Ile Leu Asp Val Val Gly
        2870              2875              2880 atg ctg tat gtt ggt ggg tta ccc atc aac tac act acc cga aga att      8746
Met Leu Tyr Val Gly Gly Leu Pro Ile Asn Tyr Thr Thr Arg Arg Ile
        2885              2890              2895 ggt cca gtg acc tat agc att gat ggc tgc gtc agg aat ctc cac atg      8794
Gly Pro Val Thr Tyr Ser Ile Asp Gly Cys Val Arg Asn Leu His Met
2900              2905              2910              2915 gca gag gcc cct gcc gat ctg gaa caa ccc acc tcc agc ttc cat gtt      8842
Ala Glu Ala Pro Ala Asp Leu Glu Gln Pro Thr Ser Ser Phe His Val
                2920              2925              2930 ggg aca tgt ttt gca aat gct cag agg gga aca tat ttt gac gga acc      8890
Gly Thr Cys Phe Ala Asn Ala Gln Arg Gly Thr Tyr Phe Asp Gly Thr
        2935              2940              2945 ggt ttt gcc aaa gca gtt ggt gga ttc aaa gtg gga ttg gac ctt ctt      8938
Gly Phe Ala Lys Ala Val Gly Gly Phe Lys Val Gly Leu Asp Leu Leu
        2950              2955              2960 gta gaa ttt gaa ttc gcg aca act aca acg act gga gtt ctt ctg ggg      8986
Val Glu Phe Glu Phe Ala Thr Thr Thr Thr Thr Gly Val Leu Leu Gly
        2965              2970              2975 atc agt agt caa aaa atg gat gga atg ggt att gaa atg att gat gaa      9034
Ile Ser Ser Gln Lys Met Asp Gly Met Gly Ile Glu Met Ile Asp Glu
2980              2985              2990              2995 aag ttg atg ttt cat gtg gac aat ggt gcg ggc aga ttc act gct gtc      9082
Lys Leu Met Phe His Val Asp Asn Gly Ala Gly Arg Phe Thr Ala Val
                3000              3005              3010 tat gat gct ggg gtt cca ggg cat ttg tgt gat gga caa tgg cat aaa      9130
Tyr Asp Ala Gly Val Pro Gly His Leu Cys Asp Gly Gln Trp His Lys
        3015              3020              3025 gtc act gcc aac aag atc aaa cac cgc att gag ctc aca gtc gat ggg      9178
Val Thr Ala Asn Lys Ile Lys His Arg Ile Glu Leu Thr Val Asp Gly
        3030              3035              3040 aac cag gtg gaa gcc caa agc cca aac cca gca tct aca tca gct gac      9226
Asn Gln Val Glu Ala Gln Ser Pro Asn Pro Ala Ser Thr Ser Ala Asp
        3045              3050              3055 aca aat gac cct gtg ttt gtt gga ggc ttc cca gat gac ctc aag cag      9274
Thr Asn Asp Pro Val Phe Val Gly Gly Phe Pro Asp Asp Leu Lys Gln
3060              3065              3070              3075 ttt ggc cta aca acc agt att ccg ttc cga ggt tgc atc aga tcc ctg      9322
```

```
Phe Gly Leu Thr Thr Ser Ile Pro Phe Arg Gly Cys Ile Arg Ser Leu
                3080                3085                3090 aag ctc acc aaa ggc aca gca agc cac tgg agg tta att ttg cca agg      9370
Lys Leu Thr Lys Gly Thr Ala Ser His Trp Arg Leu Ile Leu Pro Arg
            3095                3100                3105 ccc tgg aac tgagggcgt tcaacctgta tcatgccag ccaactaata aaataagtg      9429
Pro Trp Asn taacccagg aagagtctgt caaaacaagt atatcaagta aaacaaacaa atatatttta    9489
cctatatatg ttaattaaac taatttgtgc atgtacatag aattc                   9534

<210> SEQ ID NO 9
<211> LENGTH: 1786
<212> TYPE: PRT
<213> ORGANISM: Homo sapiens

<400> SEQUENCE: 9

Met Gly Leu Leu Gln Leu Leu Ala Phe Ser Phe Leu Ala Leu Cys Arg
 1               5                  10                  15

Ala Arg Val Arg Ala Gln Glu Pro Glu Phe Ser Tyr Gly Cys Ala Glu
             20                  25                  30

Gly Ser Cys Tyr Pro Ala Thr Gly Asp Leu Leu Ile Gly Arg Ala Gln
         35                  40                  45

Lys Leu Ser Val Thr Ser Thr Cys Gly Leu His Lys Pro Glu Pro Tyr
     50                  55                  60

Cys Ile Val Ser His Leu Gln Glu Asp Lys Lys Cys Phe Ile Cys Asn
 65                  70                  75                  80

Ser Gln Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300
```

```
-continued

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
            325                 330                 335

Cys Asn Glu His Ser Ile Ser Cys His Phe Asp Met Ala Val Tyr Leu
                340                 345                 350

Ala Thr Gly Asn Val Ser Gly Gly Val Cys Asp Cys Gln His Asn
            355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
                435                 440                 445

Ser Glu Asp Pro Phe Gly Cys Lys Ser Cys Ala Cys Asn Pro Leu Gly
    450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
    515                 520                 525

Cys Ser Cys Arg Pro His Met Ile Gly Arg Gln Cys Asn Glu Val Glu
530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
            565                 570                 575

Gln Asp Arg Ile Pro Ser Trp Thr Gly Ala Gly Phe Val Arg Val Pro
    580                 585                 590

Glu Gly Ala Tyr Leu Glu Phe Phe Ile Asp Asn Ile Pro Tyr Ser Met
    595                 600                 605

Glu Tyr Asp Ile Leu Ile Arg Tyr Glu Pro Gln Leu Pro Asp His Trp
    610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
            645                 650                 655

Leu Ser Pro Gly Ser Arg Tyr Val Val Leu Pro Arg Pro Val Cys Phe
            660                 665                 670

Glu Lys Gly Thr Asn Tyr Thr Val Arg Leu Glu Leu Pro Gln Tyr Thr
    675                 680                 685

Ser Ser Asp Ser Asp Val Glu Ser Pro Tyr Thr Leu Ile Asp Ser Leu
    690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
```

-continued

```
                725                 730                 735
Tyr Arg Cys Leu Glu Asn Ser Arg Ser Val Val Lys Thr Pro Met Thr
                740                 745                 750
Asp Val Cys Arg Asn Ile Ile Phe Ser Ile Ser Ala Leu Leu His Gln
                755                 760                 765
Thr Gly Leu Ala Cys Glu Cys Asp Pro Gln Gly Ser Leu Ser Ser Val
                770                 775                 780
Cys Asp Pro Asn Gly Gly Gln Cys Gln Cys Arg Pro Asn Val Val Gly
785                 790                 795                 800
Arg Thr Cys Asn Arg Cys Ala Pro Gly Thr Phe Gly Phe Gly Pro Ser
                805                 810                 815
Gly Cys Lys Pro Cys Glu Cys His Leu Gln Gly Ser Val Asn Ala Phe
                820                 825                 830
Cys Asn Pro Val Thr Gly Gln Cys His Cys Phe Gln Gly Val Tyr Ala
                835                 840                 845
Arg Gln Cys Asp Arg Cys Leu Pro Gly His Trp Gly Phe Pro Ser Cys
                850                 855                 860
Gln Pro Cys Gln Cys Asn Gly His Ala Asp Asp Cys Asp Pro Val Thr
865                 870                 875                 880
Gly Glu Cys Leu Asn Cys Gln Asp Tyr Thr Met Gly His Asn Cys Glu
                885                 890                 895
Arg Cys Leu Ala Gly Tyr Tyr Gly Asp Pro Ile Ile Gly Ser Gly Asp
                900                 905                 910
His Cys Arg Pro Cys Pro Cys Pro Asp Gly Pro Asp Ser Gly Arg Gln
                915                 920                 925
Phe Ala Arg Ser Cys Tyr Gln Asp Pro Val Thr Leu Gln Leu Ala Cys
                930                 935                 940
Val Cys Asp Pro Gly Tyr Ile Gly Ser Arg Cys Asp Asp Cys Ala Ser
945                 950                 955                 960
Gly Tyr Phe Gly Asn Pro Ser Glu Val Gly Gly Ser Cys Gln Pro Cys
                965                 970                 975
Gln Cys His Asn Asn Ile Asp Thr Thr Asp Pro Glu Ala Cys Asp Lys
                980                 985                 990
Glu Thr Gly Arg Cys Leu Lys Cys Leu Tyr His Thr Glu Gly Glu His
                995                 1000                1005
Cys Gln Phe Cys Arg Phe Gly Tyr Tyr Gly Asp Ala Leu Arg Gln Asp
                1010                1015                1020
Cys Arg Lys Cys Val Cys Asn Tyr Leu Gly Thr Val Gln Glu His Cys
1025                1030                1035                1040
Asn Gly Ser Asp Cys Gln Cys Asp Lys Ala Thr Gly Gln Cys Leu Cys
                1045                1050                1055
Leu Pro Asn Val Ile Gly Gln Asn Cys Asp Arg Cys Ala Pro Asn Thr
                1060                1065                1070
Trp Gln Leu Ala Ser Gly Thr Gly Cys Asp Pro Cys Asn Cys Asn Ala
                1075                1080                1085
Ala His Ser Phe Gly Pro Ser Cys Asn Glu Phe Thr Gly Gln Cys Gln
                1090                1095                1100
Cys Met Pro Gly Phe Gly Gly Arg Thr Cys Ser Glu Cys Gln Glu Leu
1105                1110                1115                1120
Phe Trp Gly Asp Pro Asp Val Glu Cys Arg Ala Cys Asp Cys Asp Pro
                1125                1130                1135
Arg Gly Ile Glu Thr Pro Gln Cys Asp Gln Ser Thr Gly Gln Cys Val
                1140                1145                1150
```

-continued

```
Cys Val Glu Gly Val Gly Pro Arg Cys Asp Lys Cys Thr Arg Gly
            1155            1160            1165
Tyr Ser Gly Val Phe Pro Asp Cys Thr Pro Cys His Gln Cys Phe Ala
    1170            1175            1180
Leu Trp Asp Val Ile Ile Ala Glu Leu Thr Asn Arg Thr His Arg Phe
1185            1190            1195            1200
Leu Glu Lys Ala Lys Ala Leu Lys Ile Ser Gly Val Ile Gly Pro Tyr
            1205            1210            1215
Arg Glu Thr Val Asp Ser Val Glu Arg Lys Val Ser Glu Ile Lys Asp
            1220            1225            1230
Ile Leu Ala Gln Ser Pro Ala Ala Glu Pro Leu Lys Asn Ile Gly Asn
            1235            1240            1245
Leu Phe Glu Glu Ala Glu Lys Leu Ile Lys Asp Val Thr Glu Met Met
    1250            1255            1260
Ala Gln Val Glu Val Lys Leu Ser Asp Thr Thr Ser Gln Ser Asn Ser
1265            1270            1275            1280
Thr Ala Lys Glu Leu Asp Ser Leu Gln Thr Glu Ala Glu Ser Leu Asp
            1285            1290            1295
Asn Thr Val Lys Glu Leu Ala Glu Gln Leu Glu Phe Ile Lys Asn Ser
            1300            1305            1310
Asp Ile Arg Gly Ala Leu Asp Ser Ile Thr Lys Tyr Phe Gln Met Ser
            1315            1320            1325
Leu Glu Ala Glu Glu Arg Val Asn Ala Ser Thr Thr Glu Pro Asn Ser
            1330            1335            1340
Thr Val Glu Gln Ser Ala Leu Met Arg Asp Arg Val Glu Asp Val Met
1345            1350            1355            1360
Met Glu Arg Glu Ser Gln Phe Lys Glu Lys Gln Glu Glu Gln Ala Arg
            1365            1370            1375
Leu Leu Asp Glu Leu Ala Gly Lys Leu Gln Ser Leu Asp Leu Ser Ala
            1380            1385            1390
Ala Ala Glu Met Thr Cys Gly Thr Pro Pro Gly Ala Ser Cys Ser Glu
            1395            1400            1405
Thr Glu Cys Gly Gly Pro Asn Cys Arg Thr Asp Glu Gly Glu Arg Lys
    1410            1415            1420
Cys Gly Gly Pro Gly Cys Gly Gly Leu Val Thr Val Ala His Asn Ala
1425            1430            1435            1440
Trp Gln Lys Ala Met Asp Leu Asp Gln Asp Val Leu Ser Ala Leu Ala
            1445            1450            1455
Glu Val Glu Gln Leu Ser Lys Met Val Ser Glu Ala Lys Leu Arg Ala
            1460            1465            1470
Asp Glu Ala Lys Gln Ser Ala Glu Asp Ile Leu Leu Lys Thr Asn Ala
            1475            1480            1485
Thr Lys Glu Lys Met Asp Lys Ser Asn Glu Glu Leu Arg Asn Leu Ile
    1490            1495            1500
Lys Gln Ile Arg Asn Phe Leu Thr Gln Asp Ser Ala Asp Leu Asp Ser
1505            1510            1515            1520
Ile Glu Ala Val Ala Asn Glu Val Leu Lys Met Glu Met Pro Ser Thr
            1525            1530            1535
Pro Gln Gln Leu Gln Asn Leu Thr Glu Asp Ile Arg Glu Arg Val Glu
            1540            1545            1550
Ser Leu Ser Gln Val Glu Val Ile Leu Gln His Ser Ala Ala Asp Ile
            1555            1560            1565
```

```
Ala Arg Ala Glu Met Leu Leu Glu Glu Ala Lys Arg Ala Ser Lys Ser
    1570                1575                1580

Ala Thr Asp Val Lys Val Thr Ala Asp Met Val Lys Glu Ala Leu Glu
1585                1590                1595                1600

Glu Ala Glu Lys Ala Gln Val Ala Ala Glu Lys Ala Ile Lys Gln Ala
                1605                1610                1615

Asp Glu Asp Ile Gln Gly Thr Gln Asn Leu Leu Thr Ser Ile Glu Ser
            1620                1625                1630

Glu Thr Ala Ala Ser Glu Glu Thr Leu Phe Asn Ala Ser Gln Arg Ile
        1635                1640                1645

Ser Glu Leu Glu Arg Asn Val Glu Glu Leu Lys Arg Lys Ala Ala Gln
    1650                1655                1660

Asn Ser Gly Glu Ala Glu Tyr Ile Glu Lys Val Val Tyr Thr Val Lys
1665                1670                1675                1680

Gln Ser Ala Glu Asp Val Lys Lys Thr Leu Asp Gly Glu Leu Asp Glu
                1685                1690                1695

Lys Tyr Lys Lys Val Glu Asn Leu Ile Ala Lys Lys Thr Glu Glu Ser
            1700                1705                1710

Ala Asp Ala Arg Arg Lys Ala Glu Met Leu Gln Asn Glu Ala Lys Thr
        1715                1720                1725

Leu Leu Ala Gln Ala Asn Ser Lys Leu Gln Leu Leu Lys Asp Leu Glu
    1730                1735                1740

Arg Lys Tyr Glu Asp Asn Gln Arg Tyr Leu Glu Asp Lys Ala Gln Glu
1745                1750                1755                1760

Leu Ala Arg Leu Glu Gly Glu Val Arg Ser Leu Leu Lys Asp Ile Ser
                1765                1770                1775

Gln Lys Val Ala Val Tyr Ser Thr Cys Leu
            1780                1785

<210> SEQ ID NO 10
<211> LENGTH: 5613
<212> TYPE: DNA
<213> ORGANISM: Homo sapiens
<220> FEATURE:
<221> NAME/KEY: CDS
<222> LOCATION: (118)...(5475)

<400> SEQUENCE: 10
cccggagcag ggcgagagct cgcgtcgccg gaaaggaaga cgggaagaaa gggcaggcgg      60
ctcggcgggc gtcttctcca ctcctctgcc gcgtccccgt ggctgcaggg agccggc atg    120
                                                             Met
                                                               1 ggg ctt ctc cag ttg cta gct ttc agt ttc tta gcc ctg tgc aga gcc      168
Gly Leu Leu Gln Leu Leu Ala Phe Ser Phe Leu Ala Leu Cys Arg Ala
        5                   10                  15 cga gtg cgc gct cag gaa ccc gag ttc agc tac ggc tgc gca gaa ggc      216
Arg Val Arg Ala Gln Glu Pro Glu Phe Ser Tyr Gly Cys Ala Glu Gly
     20                  25                  30 agc tgc tat ccc gcc acg ggc gac ctt ctc atc ggc gca cag aag        264
Ser Cys Tyr Pro Ala Thr Gly Asp Leu Leu Ile Gly Arg Ala Gln Lys
 35                  40                  45 ctt tcg gtg acc tcg acg tgc ggg ctg cac aag ccc gaa ccc tac tgt      312
Leu Ser Val Thr Ser Thr Cys Gly Leu His Lys Pro Glu Pro Tyr Cys
 50                  55                  60                  65 atc gtc agc cac ttg cag gag gac aaa aaa tgc ttc ata tgc aat tcc      360
Ile Val Ser His Leu Gln Glu Asp Lys Lys Cys Phe Ile Cys Asn Ser
             70                  75                  80
```

```
caa gat cct tat cat gag acc ctg aat cct gac agc cat ctc att gaa    408
Gln Asp Pro Tyr His Glu Thr Leu Asn Pro Asp Ser His Leu Ile Glu
            85                  90                  95 aat gtg gtc act aca ttt gct cca aac cgc ctt aag att tgg tgg caa    456
Asn Val Val Thr Thr Phe Ala Pro Asn Arg Leu Lys Ile Trp Trp Gln
100                 105                 110 tct gaa aat ggt gtg gaa aat gta act atc caa ctg gat ttg gaa gca    504
Ser Glu Asn Gly Val Glu Asn Val Thr Ile Gln Leu Asp Leu Glu Ala
    115                 120                 125 gaa ttc cat ttt act cat ctc ata atg act ttc aag aca ttc cgt cca    552
Glu Phe His Phe Thr His Leu Ile Met Thr Phe Lys Thr Phe Arg Pro
130                 135                 140                 145 gct gct atg ctg ata gaa cga tcg tcc gac ttt ggg aaa acc tgg ggt    600
Ala Ala Met Leu Ile Glu Arg Ser Ser Asp Phe Gly Lys Thr Trp Gly
            150                 155                 160 gtg tat aga tac ttc gcc tat gac tgt gag gcc tcg ttt cca ggc att    648
Val Tyr Arg Tyr Phe Ala Tyr Asp Cys Glu Ala Ser Phe Pro Gly Ile
                165                 170                 175 tca act ggc ccc atg aaa aaa gtc gat gac ata att tgt gat tct cga    696
Ser Thr Gly Pro Met Lys Lys Val Asp Asp Ile Ile Cys Asp Ser Arg
        180                 185                 190 tat tct gac att gaa ccc tca act gaa gga gag gtg ata ttt cgt gct    744
Tyr Ser Asp Ile Glu Pro Ser Thr Glu Gly Glu Val Ile Phe Arg Ala
    195                 200                 205 tta gat cct gct ttc aaa ata gaa gat cct tat agc cca agg ata cag    792
Leu Asp Pro Ala Phe Lys Ile Glu Asp Pro Tyr Ser Pro Arg Ile Gln
210                 215                 220                 225 aat tta tta aaa att acc aac ttg aga atc aag ttt gtg aaa ctg cat    840
Asn Leu Leu Lys Ile Thr Asn Leu Arg Ile Lys Phe Val Lys Leu His
            230                 235                 240 act ttg gga gat aac ctt ctg gat tcc agg atg gaa atc aga gaa aag    888
Thr Leu Gly Asp Asn Leu Leu Asp Ser Arg Met Glu Ile Arg Glu Lys
                245                 250                 255 tat tat tat gca gtt tat gat atg gtg gtt cga gga aat tgc ttc tgc    936
Tyr Tyr Tyr Ala Val Tyr Asp Met Val Val Arg Gly Asn Cys Phe Cys
        260                 265                 270 tat ggt cat gcc agc gaa tgt gcc cct gtg gat gga ttc aat gaa gaa    984
Tyr Gly His Ala Ser Glu Cys Ala Pro Val Asp Gly Phe Asn Glu Glu
    275                 280                 285 gtg gaa gga atg gtt cac gga cac tgc atg tgc agg cat aac acc aag   1032
Val Glu Gly Met Val His Gly His Cys Met Cys Arg His Asn Thr Lys
290                 295                 300                 305 ggc tta aac tgt gaa ctc tgc atg gat ttc tac cat gat tta cct tgg   1080
Gly Leu Asn Cys Glu Leu Cys Met Asp Phe Tyr His Asp Leu Pro Trp
            310                 315                 320 aga cct gct gaa ggc cga aac agc aac gcc tgt aaa aaa tgt aac tgc   1128
Arg Pro Ala Glu Gly Arg Asn Ser Asn Ala Cys Lys Lys Cys Asn Cys
                325                 330                 335 aat gaa cat tcc atc tct tgt cac ttt gac atg gct gtt tac ctg gcc   1176
Asn Glu His Ser Ile Ser Cys His Phe Asp Met Ala Val Tyr Leu Ala
        340                 345                 350 acg ggg aac gtc agc gga ggc gtg tgt gat gac tgt cag cac aac acc   1224
Thr Gly Asn Val Ser Gly Gly Val Cys Asp Asp Cys Gln His Asn Thr
    355                 360                 365 atg ggg cgc aac tgt gag cag tgc aag ccg ttt tac tac cag cac cca   1272
Met Gly Arg Asn Cys Glu Gln Cys Lys Pro Phe Tyr Tyr Gln His Pro
370                 375                 380                 385 gag agg gac atc cga gat cct aat ttc tgt gaa cga tgt acg tgt gac   1320
Glu Arg Asp Ile Arg Asp Pro Asn Phe Cys Glu Arg Cys Thr Cys Asp
            390                 395                 400
```

```
cca gct ggc tct caa aat gag gga att tgt gac agc tat act gat ttt      1368
Pro Ala Gly Ser Gln Asn Glu Gly Ile Cys Asp Ser Tyr Thr Asp Phe
                405                 410                 415 tct act ggt ctc att gct ggc cag tgt cgg tgt aaa tta aat gtg gaa      1416
Ser Thr Gly Leu Ile Ala Gly Gln Cys Arg Cys Lys Leu Asn Val Glu
            420                 425                 430 gga gaa cat tgt gat gtt tgc aaa gaa ggc ttc tat gat tta agc agt      1464
Gly Glu His Cys Asp Val Cys Lys Glu Gly Phe Tyr Asp Leu Ser Ser
        435                 440                 445 gaa gat cca ttt ggt tgt aaa tct tgt gct tgc aat cct ctg gga aca      1512
Glu Asp Pro Phe Gly Cys Lys Ser Cys Ala Cys Asn Pro Leu Gly Thr
450                 455                 460                 465 att cct gga ggg aat cct tgt gat tcc gag aca ggt cac tgc tac tgc      1560
Ile Pro Gly Gly Asn Pro Cys Asp Ser Glu Thr Gly His Cys Tyr Cys
                470                 475                 480 aag cgt ctg gtg aca gga cag cat tgt gac cag tgc ctg cca gag cac      1608
Lys Arg Leu Val Thr Gly Gln His Cys Asp Gln Cys Leu Pro Glu His
            485                 490                 495 tgg ggc tta agc aat gat ttg gat gga tgt cga cca tgt gac tgt gac      1656
Trp Gly Leu Ser Asn Asp Leu Asp Gly Cys Arg Pro Cys Asp Cys Asp
        500                 505                 510 ctt ggg gga gcc tta aac aac agt tgc ttt gcg gag tca ggc cag tgc      1704
Leu Gly Gly Ala Leu Asn Asn Ser Cys Phe Ala Glu Ser Gly Gln Cys
515                 520                 525 tca tgc cgg cct cac atg att gga cgt cag tgc aac gaa gtg gaa cct      1752
Ser Cys Arg Pro His Met Ile Gly Arg Gln Cys Asn Glu Val Glu Pro
530                 535                 540                 545 ggt tac tac ttt gcc acc ctg gat cac tac ctc tat gaa gcg gag gaa      1800
Gly Tyr Tyr Phe Ala Thr Leu Asp His Tyr Leu Tyr Glu Ala Glu Glu
                550                 555                 560 gcc aac ttg ggg cct ggg gtt agc ata gtg gag cgg caa tat atc cag      1848
Ala Asn Leu Gly Pro Gly Val Ser Ile Val Glu Arg Gln Tyr Ile Gln
            565                 570                 575 gac cgg att ccc tcc tgg act gga gcc ggc ttc gtc cga gtg cct gaa      1896
Asp Arg Ile Pro Ser Trp Thr Gly Ala Gly Phe Val Arg Val Pro Glu
        580                 585                 590 ggg gct tat ttg gag ttt ttc att gac aac ata cca tat tcc atg gag      1944
Gly Ala Tyr Leu Glu Phe Phe Ile Asp Asn Ile Pro Tyr Ser Met Glu
    595                 600                 605 tac gac atc cta att cgc tac gag cca cag cta ccc gac cac tgg gaa      1992
Tyr Asp Ile Leu Ile Arg Tyr Glu Pro Gln Leu Pro Asp His Trp Glu
610                 615                 620                 625 aaa gct gtc atc aca gtg cag cga cct gga agg att cca acc agc agc      2040
Lys Ala Val Ile Thr Val Gln Arg Pro Gly Arg Ile Pro Thr Ser Ser
                630                 635                 640 cga tgt ggt aat acc atc ccc gat gat gac aac cag gtg gtg tca tta      2088
Arg Cys Gly Asn Thr Ile Pro Asp Asp Asp Asn Gln Val Val Ser Leu
            645                 650                 655 tca cca ggc tca aga tat gtc gtc ctt cct cgg ccg gtg tgc ttt gag      2136
Ser Pro Gly Ser Arg Tyr Val Val Leu Pro Arg Pro Val Cys Phe Glu
        660                 665                 670 aag gga aca aac tac acg gtg agg ttg gag ctg cct cag tac acc tcc      2184
Lys Gly Thr Asn Tyr Thr Val Arg Leu Glu Leu Pro Gln Tyr Thr Ser
675                 680                 685 tct gat agc gac gtg gag agc ccc tac acg ctg atc gat tct ctt gtt      2232
Ser Asp Ser Asp Val Glu Ser Pro Tyr Thr Leu Ile Asp Ser Leu Val
690                 695                 700                 705 ctc atg cca tac tgt aaa tca ctg gac atc ttc acc gtg gga ggt tca      2280
Leu Met Pro Tyr Cys Lys Ser Leu Asp Ile Phe Thr Val Gly Gly Ser
```

-continued

|     |     | 710 |     |     |     |     | 715 |     |     |     |     | 720 |     |     |     |      |
|-----|-----|-----|-----|-----|-----|-----|-----|-----|-----|-----|-----|-----|-----|-----|-----|------|
| gga | gat | ggg | gtg | gtc | acc | aac | agt | gcc | tgg | gaa | acc | ttt | cag | aga | tac | 2328 |
| Gly | Asp | Gly | Val | Val | Thr | Asn | Ser | Ala | Trp | Glu | Thr | Phe | Gln | Arg | Tyr |      |
|     |     | 725 |     |     |     |     | 730 |     |     |     |     | 735 |     |     |     |      |

| cga | tgt | cta | gag | aac | agc | aga | agc | gtt | gtg | aaa | aca | ccg | atg | aca | gat | 2376 |
|-----|-----|-----|-----|-----|-----|-----|-----|-----|-----|-----|-----|-----|-----|-----|-----|------|
| Arg | Cys | Leu | Glu | Asn | Ser | Arg | Ser | Val | Val | Lys | Thr | Pro | Met | Thr | Asp |      |
|     |     |     | 740 |     |     |     |     | 745 |     |     |     |     | 750 |     |     |      |

| gtt | tgc | aga | aac | atc | atc | ttt | agc | att | tct | gcc | ctg | tta | cac | cag | aca | 2424 |
|-----|-----|-----|-----|-----|-----|-----|-----|-----|-----|-----|-----|-----|-----|-----|-----|------|
| Val | Cys | Arg | Asn | Ile | Ile | Phe | Ser | Ile | Ser | Ala | Leu | Leu | His | Gln | Thr |      |
|     |     | 755 |     |     |     |     | 760 |     |     |     |     | 765 |     |     |     |      |

| ggc | ctg | gct | tgt | gaa | tgc | gac | cct | cag | ggt | tcg | tta | agt | tcc | gtg | tgt | 2472 |
|-----|-----|-----|-----|-----|-----|-----|-----|-----|-----|-----|-----|-----|-----|-----|-----|------|
| Gly | Leu | Ala | Cys | Glu | Cys | Asp | Pro | Gln | Gly | Ser | Leu | Ser | Ser | Val | Cys |      |
| 770 |     |     |     | 775 |     |     |     |     | 780 |     |     |     |     | 785 |     |      |

| gat | ccc | aac | gga | ggc | cag | tgc | cag | tgc | cgg | ccc | aac | gtg | gtt | gga | aga | 2520 |
|-----|-----|-----|-----|-----|-----|-----|-----|-----|-----|-----|-----|-----|-----|-----|-----|------|
| Asp | Pro | Asn | Gly | Gly | Gln | Cys | Gln | Cys | Arg | Pro | Asn | Val | Val | Gly | Arg |      |
|     |     |     | 790 |     |     |     |     | 795 |     |     |     |     | 800 |     |     |      |

| acc | tgc | aac | aga | tgt | gca | cct | gga | act | ttt | ggc | ttt | ggc | ccc | agt | gga | 2568 |
|-----|-----|-----|-----|-----|-----|-----|-----|-----|-----|-----|-----|-----|-----|-----|-----|------|
| Thr | Cys | Asn | Arg | Cys | Ala | Pro | Gly | Thr | Phe | Gly | Phe | Gly | Pro | Ser | Gly |      |
|     |     |     | 805 |     |     |     |     | 810 |     |     |     |     | 815 |     |     |      |

| tgc | aaa | cct | tgt | gag | tgc | cat | ctg | caa | gga | tct | gtc | aat | gcc | ttc | tgc | 2616 |
|-----|-----|-----|-----|-----|-----|-----|-----|-----|-----|-----|-----|-----|-----|-----|-----|------|
| Cys | Lys | Pro | Cys | Glu | Cys | His | Leu | Gln | Gly | Ser | Val | Asn | Ala | Phe | Cys |      |
|     |     | 820 |     |     |     |     | 825 |     |     |     |     | 830 |     |     |     |      |

| aat | ccc | gtc | act | ggc | cag | tgc | cac | tgt | ttc | cag | gga | gtg | tat | gct | cgg | 2664 |
|-----|-----|-----|-----|-----|-----|-----|-----|-----|-----|-----|-----|-----|-----|-----|-----|------|
| Asn | Pro | Val | Thr | Gly | Gln | Cys | His | Cys | Phe | Gln | Gly | Val | Tyr | Ala | Arg |      |
|     |     | 835 |     |     |     |     | 840 |     |     |     |     | 845 |     |     |     |      |

| cag | tgt | gat | cgg | tgc | tta | cct | ggg | cac | tgg | ggc | ttt | cca | agt | tgc | cag | 2712 |
|-----|-----|-----|-----|-----|-----|-----|-----|-----|-----|-----|-----|-----|-----|-----|-----|------|
| Gln | Cys | Asp | Arg | Cys | Leu | Pro | Gly | His | Trp | Gly | Phe | Pro | Ser | Cys | Gln |      |
| 850 |     |     |     | 855 |     |     |     |     | 860 |     |     |     |     | 865 |     |      |

| ccc | tgc | cag | tgc | aat | ggc | cac | gcc | gat | gac | tgc | gac | cca | gtg | act | ggg | 2760 |
|-----|-----|-----|-----|-----|-----|-----|-----|-----|-----|-----|-----|-----|-----|-----|-----|------|
| Pro | Cys | Gln | Cys | Asn | Gly | His | Ala | Asp | Asp | Cys | Asp | Pro | Val | Thr | Gly |      |
|     |     |     | 870 |     |     |     |     | 875 |     |     |     |     | 880 |     |     |      |

| gag | tgc | ttg | aac | tgc | cag | gac | tac | acc | atg | ggt | cat | aac | tgt | gaa | agg | 2808 |
|-----|-----|-----|-----|-----|-----|-----|-----|-----|-----|-----|-----|-----|-----|-----|-----|------|
| Glu | Cys | Leu | Asn | Cys | Gln | Asp | Tyr | Thr | Met | Gly | His | Asn | Cys | Glu | Arg |      |
|     |     |     | 885 |     |     |     |     | 890 |     |     |     |     | 895 |     |     |      |

| tgc | ttg | gct | ggt | tac | tat | ggc | gac | ccc | atc | att | ggg | tca | ggt | gat | cac | 2856 |
|-----|-----|-----|-----|-----|-----|-----|-----|-----|-----|-----|-----|-----|-----|-----|-----|------|
| Cys | Leu | Ala | Gly | Tyr | Tyr | Gly | Asp | Pro | Ile | Ile | Gly | Ser | Gly | Asp | His |      |
|     |     | 900 |     |     |     |     | 905 |     |     |     |     | 910 |     |     |     |      |

| tgc | cgc | cct | tgc | cct | tgc | cca | gat | ggt | ccc | gac | agt | gga | cgc | cag | ttt | 2904 |
|-----|-----|-----|-----|-----|-----|-----|-----|-----|-----|-----|-----|-----|-----|-----|-----|------|
| Cys | Arg | Pro | Cys | Pro | Cys | Pro | Asp | Gly | Pro | Asp | Ser | Gly | Arg | Gln | Phe |      |
| 915 |     |     |     | 920 |     |     |     |     | 925 |     |     |     |     |     |     |      |

| gcc | agg | agc | tgc | tac | caa | gat | cct | gtt | act | tta | cag | ctt | gcc | tgt | gtt | 2952 |
|-----|-----|-----|-----|-----|-----|-----|-----|-----|-----|-----|-----|-----|-----|-----|-----|------|
| Ala | Arg | Ser | Cys | Tyr | Gln | Asp | Pro | Val | Thr | Leu | Gln | Leu | Ala | Cys | Val |      |
| 930 |     |     |     | 935 |     |     |     |     | 940 |     |     |     |     | 945 |     |      |

| tgt | gat | cct | gga | tac | att | ggt | tcc | aga | tgt | gac | gac | tgt | gcc | tca | gga | 3000 |
|-----|-----|-----|-----|-----|-----|-----|-----|-----|-----|-----|-----|-----|-----|-----|-----|------|
| Cys | Asp | Pro | Gly | Tyr | Ile | Gly | Ser | Arg | Cys | Asp | Asp | Cys | Ala | Ser | Gly |      |
|     |     |     | 950 |     |     |     |     | 955 |     |     |     |     | 960 |     |     |      |

| tac | ttt | ggc | aat | cca | tca | gaa | gtt | ggg | ggg | tcg | tgt | cag | cct | tgc | cag | 3048 |
|-----|-----|-----|-----|-----|-----|-----|-----|-----|-----|-----|-----|-----|-----|-----|-----|------|
| Tyr | Phe | Gly | Asn | Pro | Ser | Glu | Val | Gly | Gly | Ser | Cys | Gln | Pro | Cys | Gln |      |
|     |     |     | 965 |     |     |     |     | 970 |     |     |     |     | 975 |     |     |      |

| tgt | cac | aac | aac | att | gac | acg | aca | gac | cca | gaa | gcc | tgt | gac | aag | gag | 3096 |
|-----|-----|-----|-----|-----|-----|-----|-----|-----|-----|-----|-----|-----|-----|-----|-----|------|
| Cys | His | Asn | Asn | Ile | Asp | Thr | Thr | Asp | Pro | Glu | Ala | Cys | Asp | Lys | Glu |      |
|     |     |     | 980 |     |     |     |     | 985 |     |     |     |     | 990 |     |     |      |

| act | ggg | agg | tgt | ctc | aag | tgc | ctg | tac | cac | acg | gaa | ggg | gaa | cac | tgt | 3144 |
|-----|-----|-----|-----|-----|-----|-----|-----|-----|-----|-----|-----|-----|-----|-----|-----|------|
| Thr | Gly | Arg | Cys | Leu | Lys | Cys | Leu | Tyr | His | Thr | Glu | Gly | Glu | His | Cys |      |
|     |     | 995 |     |     |     |     | 1000|     |     |     |     | 1005|     |     |     |      |

| cag | ttc | tgc | cgg | ttt | gga | tac | tat | ggt | gat | gcc | ctc | cgg | cag | gac | tgt | 3192 |
|-----|-----|-----|-----|-----|-----|-----|-----|-----|-----|-----|-----|-----|-----|-----|-----|------|
| Gln | Phe | Cys | Arg | Phe | Gly | Tyr | Tyr | Gly | Asp | Ala | Leu | Arg | Gln | Asp | Cys |      |
| 1010|     |     |     | 1015|     |     |     |     | 1020|     |     |     |     | 1025|     |      |

| cga | aag | tgt | gtc | tgt | aat | tac | ctg | ggc | acc | gtg | caa | gag | cac | tgt | aac | 3240 |

-continued

```
              Arg Lys Cys Val Cys Asn Tyr Leu Gly Thr Val Gln Glu His Cys Asn
                              1030                1035                1040 ggc tct gac tgc cag tgc gac aaa gcc act ggt cag tgc ttg tgt ctt           3288
Gly Ser Asp Cys Gln Cys Asp Lys Ala Thr Gly Gln Cys Leu Cys Leu
            1045                1050                1055 cct aat gtg atc ggg cag aac tgt gac cgc tgt gcg ccc aat acc tgg           3336
Pro Asn Val Ile Gly Gln Asn Cys Asp Arg Cys Ala Pro Asn Thr Trp
        1060                1065                1070 cag ctg gcc agt ggc act ggc tgt gac cca tgc aac tgc aat gct gct           3384
Gln Leu Ala Ser Gly Thr Gly Cys Asp Pro Cys Asn Cys Asn Ala Ala
    1075                1080                1085 cat tcc ttc ggg cca tct tgc aat gag ttc acg ggg cag tgc cag tgc           3432
His Ser Phe Gly Pro Ser Cys Asn Glu Phe Thr Gly Gln Cys Gln Cys
1090                1095                1100                1105 atg cct ggg ttt gga ggc cgc acc tgc agc gag tgc cag gaa ctc ttc           3480
Met Pro Gly Phe Gly Gly Arg Thr Cys Ser Glu Cys Gln Glu Leu Phe
                1110                1115                1120 tgg gga gac ccc gac gtg gag tgc cga gcc tgt gac tgt gac ccc agg           3528
Trp Gly Asp Pro Asp Val Glu Cys Arg Ala Cys Asp Cys Asp Pro Arg
            1125                1130                1135 ggc att gag acg cca cag tgt gac cag tcc acg ggc cag tgt gtc tgc           3576
Gly Ile Glu Thr Pro Gln Cys Asp Gln Ser Thr Gly Gln Cys Val Cys
        1140                1145                1150 gtt gag ggt gtt gag ggt cca cgc tgt gac aag tgc acg cga ggg tac           3624
Val Glu Gly Val Glu Gly Pro Arg Cys Asp Lys Cys Thr Arg Gly Tyr
    1155                1160                1165 tcg ggg gtc ttc cct gac tgc aca ccc tgc cac cag tgc ttt gct ctc           3672
Ser Gly Val Phe Pro Asp Cys Thr Pro Cys His Gln Cys Phe Ala Leu
1170                1175                1180                1185 tgg gat gtg atc att gcc gag ctg acc aac agg aca cac aga ttc ctg           3720
Trp Asp Val Ile Ile Ala Glu Leu Thr Asn Arg Thr His Arg Phe Leu
                1190                1195                1200 gag aaa gcc aag gcc ttg aag atc agt ggt gtg atc ggg cct tac cgt           3768
Glu Lys Ala Lys Ala Leu Lys Ile Ser Gly Val Ile Gly Pro Tyr Arg
            1205                1210                1215 gag act gtg gac tcg gtg gag agg aaa gtc agc gag ata aaa gac atc           3816
Glu Thr Val Asp Ser Val Glu Arg Lys Val Ser Glu Ile Lys Asp Ile
        1220                1225                1230 ctg gcg cag agc ccc gca gca gag cca ctg aaa aac att ggg aat ctc           3864
Leu Ala Gln Ser Pro Ala Ala Glu Pro Leu Lys Asn Ile Gly Asn Leu
    1235                1240                1245 ttt gag gaa gca gag aaa ctg att aaa gat gtt aca gaa atg atg gct           3912
Phe Glu Glu Ala Glu Lys Leu Ile Lys Asp Val Thr Glu Met Met Ala
1250                1255                1260                1265 caa gta gaa gtg aaa tta tct gac aca act tcc caa agc aac agc aca           3960
Gln Val Glu Val Lys Leu Ser Asp Thr Thr Ser Gln Ser Asn Ser Thr
                1270                1275                1280 gcc aaa gaa ctg gat tct cta cag aca gaa gcc gaa agc cta gac aac           4008
Ala Lys Glu Leu Asp Ser Leu Gln Thr Glu Ala Glu Ser Leu Asp Asn
            1285                1290                1295 act gtg aaa gaa ctt gct gaa caa ctg gaa ttt atc aaa aac tca gat           4056
Thr Val Lys Glu Leu Ala Glu Gln Leu Glu Phe Ile Lys Asn Ser Asp
        1300                1305                1310 att cgg ggt gcc ttg gat agc att acc aag tat ttc cag atg tct ctt           4104
Ile Arg Gly Ala Leu Asp Ser Ile Thr Lys Tyr Phe Gln Met Ser Leu
    1315                1320                1325 gag gca gag gag agg gtg aat gcc tcc acc aca gaa ccc aac agc act           4152
Glu Ala Glu Glu Arg Val Asn Ala Ser Thr Thr Glu Pro Asn Ser Thr
1330                1335                1340                1345
```

```
gtg gag cag tca gcc ctc atg aga gac aga gta gaa gac gtg atg atg      4200
Val Glu Gln Ser Ala Leu Met Arg Asp Arg Val Glu Asp Val Met Met
            1350                1355                1360 gag cga gaa tcc cag ttc aag gaa aaa caa gag gag cag gct cgc ctc      4248
Glu Arg Glu Ser Gln Phe Lys Glu Lys Gln Glu Glu Gln Ala Arg Leu
        1365                1370                1375 ctt gat gaa ctg gca ggc aag cta caa agc cta gac ctt tca gcc gct      4296
Leu Asp Glu Leu Ala Gly Lys Leu Gln Ser Leu Asp Leu Ser Ala Ala
    1380                1385                1390 gcc gaa atg acc tgt gga aca ccc cca ggg gcc tcc tgt tcc gag act      4344
Ala Glu Met Thr Cys Gly Thr Pro Pro Gly Ala Ser Cys Ser Glu Thr
1395                1400                1405 gaa tgt ggc ggg cca aac tgc aga act gac gaa gga gag agg aag tgt      4392
Glu Cys Gly Gly Pro Asn Cys Arg Thr Asp Glu Gly Glu Arg Lys Cys
1410                1415                1420                1425 ggg ggg cct ggc tgt ggt ggt ctg gtt act gtt gca cac aac gcc tgg      4440
Gly Gly Pro Gly Cys Gly Gly Leu Val Thr Val Ala His Asn Ala Trp
            1430                1435                1440 cag aaa gcc atg gac ttg gac caa gat gtc ctg agt gcc ctg gct gaa      4488
Gln Lys Ala Met Asp Leu Asp Gln Asp Val Leu Ser Ala Leu Ala Glu
        1445                1450                1455 gtg gaa cag ctc tcc aag atg gtc tct gaa gca aaa ctg agg gca gat      4536
Val Glu Gln Leu Ser Lys Met Val Ser Glu Ala Lys Leu Arg Ala Asp
    1460                1465                1470 gag gca aaa caa agt gct gaa gac att ctg ttg aag aca aat gct acc      4584
Glu Ala Lys Gln Ser Ala Glu Asp Ile Leu Leu Lys Thr Asn Ala Thr
1475                1480                1485 aaa gaa aaa atg gac aag agc aat gag gag ctg aga aat cta atc aag      4632
Lys Glu Lys Met Asp Lys Ser Asn Glu Glu Leu Arg Asn Leu Ile Lys
1490                1495                1500                1505 caa atc aga aac ttt ttg acc cag gat agt gct gat ttg gac agc att      4680
Gln Ile Arg Asn Phe Leu Thr Gln Asp Ser Ala Asp Leu Asp Ser Ile
            1510                1515                1520 gaa gca gtt gct aat gaa gta ttg aaa atg gag atg cct agc acc cca      4728
Glu Ala Val Ala Asn Glu Val Leu Lys Met Glu Met Pro Ser Thr Pro
        1525                1530                1535 cag cag tta cag aac ttg aca gaa gat ata cgt gaa cga gtt gaa agc      4776
Gln Gln Leu Gln Asn Leu Thr Glu Asp Ile Arg Glu Arg Val Glu Ser
    1540                1545                1550 ctt tct caa gta gag gtt att ctt cag cat agt gct gct gac att gcc      4824
Leu Ser Gln Val Glu Val Ile Leu Gln His Ser Ala Ala Asp Ile Ala
1555                1560                1565 aga gct gag atg ttg tta gaa gaa gct aaa aga gca agc aaa agt gca      4872
Arg Ala Glu Met Leu Leu Glu Glu Ala Lys Arg Ala Ser Lys Ser Ala
1570                1575                1580                1585 aca gat gtt aaa gtc act gca gat atg gta aag gaa gct ctg gaa gaa      4920
Thr Asp Val Lys Val Thr Ala Asp Met Val Lys Glu Ala Leu Glu Glu
            1590                1595                1600 gca gaa aag gcc cag gtc gca gca gag aag gca att aaa caa gca gat      4968
Ala Glu Lys Ala Gln Val Ala Ala Glu Lys Ala Ile Lys Gln Ala Asp
        1605                1610                1615 gaa gac att caa gga acc cag aac ctg tta act tcg att gag tct gaa      5016
Glu Asp Ile Gln Gly Thr Gln Asn Leu Leu Thr Ser Ile Glu Ser Glu
    1620                1625                1630 aca gca gct tct gag gaa acc ttg ttc aac gcg tcc cag cgc atc agc      5064
Thr Ala Ala Ser Glu Glu Thr Leu Phe Asn Ala Ser Gln Arg Ile Ser
1635                1640                1645 gag tta gag agg aat gtg gaa gaa ctt aag cgg aaa gct gcc caa aac      5112
Glu Leu Glu Arg Asn Val Glu Glu Leu Lys Arg Lys Ala Ala Gln Asn
1650                1655                1660                1665
```

-continued

```
tcc ggg gag gca gaa tat att gaa aaa gta gta tat act gtg aag caa    5160
Ser Gly Glu Ala Glu Tyr Ile Glu Lys Val Val Tyr Thr Val Lys Gln
            1670                1675                1680 agt gca gaa gat gtt aag aag act tta gat ggt gaa ctt gat gaa aag    5208
Ser Ala Glu Asp Val Lys Lys Thr Leu Asp Gly Glu Leu Asp Glu Lys
        1685                1690                1695 tat aaa aaa gta gaa aat tta att gcc aaa aaa act gaa gag tca gct    5256
Tyr Lys Lys Val Glu Asn Leu Ile Ala Lys Lys Thr Glu Glu Ser Ala
        1700                1705                1710 gat gcc aga agg aaa gcc gaa atg cta caa aat gaa gca aaa act ctt    5304
Asp Ala Arg Arg Lys Ala Glu Met Leu Gln Asn Glu Ala Lys Thr Leu
        1715                1720                1725 tta gct caa gca aat agc aag ctg caa ctg ctc aaa gat tta gaa aga    5352
Leu Ala Gln Ala Asn Ser Lys Leu Gln Leu Leu Lys Asp Leu Glu Arg
1730                1735                1740                1745 aaa tat gaa gac aat caa aga tac tta gaa gat aaa gct caa gaa tta    5400
Lys Tyr Glu Asp Asn Gln Arg Tyr Leu Glu Asp Lys Ala Gln Glu Leu
            1750                1755                1760 gca aga ctg gaa gga gaa gtc cgt tca ctc cta aag gat ata agc cag    5448
Ala Arg Leu Glu Gly Glu Val Arg Ser Leu Leu Lys Asp Ile Ser Gln
        1765                1770                1775 aaa gtt gct gtg tat agc aca tgc ttg taacagagga gaataaaaaa          5495
Lys Val Ala Val Tyr Ser Thr Cys Leu
        1780                1785 tggctgaggt gaacaaggta aaacaactac attttaaaaa ctgacttaat gctcttcaaa  5555
ataaaacatc acctatttaa tgttttttaat cacattttgt atgagttaaa taaagccc   5613

<210> SEQ ID NO 11
<211> LENGTH: 1798
<212> TYPE: PRT
<213> ORGANISM: Homo sapiens

<400> SEQUENCE: 11

Met Gln Leu Thr Ser Thr Glu Arg Gly Arg Gly Gln Pro Leu Pro Trp
1               5                   10                  15

Glu Leu Arg Leu Pro Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Ala Asp Leu Leu Val Gly Arg Ala Asp Arg Leu Thr Ala
    50                  55                  60

Ser Ser Thr Cys Gly Leu Asn Gly Arg Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Thr His Arg Ile Gln Asn Val Val
            100                 105                 110

Thr Ser Phe Ala Pro Gln Arg Arg Ala Ala Trp Trp Gln Ser Gln Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
```

-continued

```
                180                 185                 190
Pro Pro Arg His Trp Asp Asp Val Val Cys Glu Ser Arg Tyr Ser Glu
            195                 200                 205
Ile Glu Pro Ser Thr Glu Gly Glu Val Ile Tyr Arg Val Leu Asp Pro
            210                 215                 220
Ala Ile Pro Ile Pro Asp Pro Tyr Ser Ser Arg Ile Gln Asn Leu Leu
225                 230                 235                 240
Lys Ile Thr Asn Leu Arg Val Asn Leu Thr Arg Leu His Thr Leu Gly
                245                 250                 255
Asp Asn Leu Leu Asp Pro Arg Arg Glu Ile Arg Glu Lys Tyr Tyr Tyr
                260                 265                 270
Ala Leu Tyr Glu Leu Val Val Arg Gly Asn Cys Phe Cys Tyr Gly His
                275                 280                 285
Ala Ser Glu Cys Ala Pro Ala Pro Gly Ala Pro Ala His Ala Glu Gly
            290                 295                 300
Met Val His Gly Ala Cys Ile Cys Lys His Asn Thr Arg Gly Leu Asn
305                 310                 315                 320
Cys Glu Gln Cys Gln Asp Phe Tyr Arg Asp Leu Pro Trp Arg Pro Ala
                325                 330                 335
Glu Asp Gly His Ser His Ala Cys Arg Lys Cys Asp Arg His Gly His
                340                 345                 350
Thr His Ser Cys His Phe Asp Met Ala Val Tyr Leu Gly Ser Gly Asn
                355                 360                 365
Val Ser Gly Gly Val Cys Asp Gly Cys Gln His Asn Thr Ala Tyr Arg
            370                 375                 380
His Cys Glu Leu Cys Arg Pro Phe Phe Tyr Arg Asp Pro Thr Lys Asp
385                 390                 395                 400
Leu Arg Asp Pro Ala Val Cys Arg Ser Cys Asp Cys Asp Pro Met Gly
                405                 410                 415
Ser Gln Asp Gly Gly Arg Cys Asp Ser His Asp Asp Pro Ala Leu Gly
                420                 425                 430
Leu Val Ser Gly Gln Cys Arg Cys Lys Glu His Val Val Gly Thr Arg
            435                 440                 445
Cys Gln Gln Cys Arg Asp Gly Phe Phe Gly Leu Ser Ile Ser Asp Pro
450                 455                 460
Ser Gly Cys Arg Arg Cys Gln Cys Asn Ala Arg Gly Thr Val Pro Gly
465                 470                 475                 480
Ser Thr Pro Cys Asp Pro Asn Ser Gly Ser Cys Tyr Cys Lys Arg Leu
                485                 490                 495
Val Thr Gly Arg Gly Cys Asp Arg Cys Leu Pro Gly His Trp Gly Leu
                500                 505                 510
Ser Leu Asp Leu Leu Gly Cys Arg Pro Cys Asp Cys Asp Val Gly Gly
            515                 520                 525
Ala Leu Asp Pro Gln Cys Asp Glu Gly Thr Gly Gln Cys His Cys Arg
            530                 535                 540
Gln His Met Val Gly Arg Cys Glu Gln Val Gln Pro Gly Tyr Phe
545                 550                 555                 560
Arg Pro Phe Leu Asp His Leu Ile Trp Glu Ala Glu Asn Thr Arg Gly
                565                 570                 575
Gln Val Leu Asp Val Val Glu Arg Leu Val Thr Pro Gly Glu Thr Pro
            580                 585                 590
Ser Trp Thr Gly Ser Gly Phe Val Arg Val Leu Glu Gly Gln Thr Leu
            595                 600                 605
```

```
Glu Phe Leu Val Ala Ser Val Pro Asn Ala Met Asp Tyr Asp Leu Leu
    610                 615                 620

Leu Arg Leu Glu Pro Gln Val Pro Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Arg Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
    690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
    770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Thr Cys
                805                 810                 815

Ala Pro Gly Tyr Tyr Gly Phe Gly Pro Thr Gly Cys Gln Ala Cys Gln
                820                 825                 830

Cys Ser Pro Arg Gly Ala Leu Ser Ser Leu Cys Glu Arg Thr Ser Gly
        835                 840                 845

Gln Cys Leu Cys Arg Thr Gly Ala Phe Gly Leu Arg Cys Asp Ala Cys
    850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
                900                 905                 910

His Gly Asp Pro Arg Leu Pro Tyr Gly Ala Gln Cys Arg Pro Cys Pro
        915                 920                 925

Cys Pro Glu Gly Pro Gly Ser Gln Arg His Phe Ala Thr Ser Cys His
    930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly Gln Phe Gly Asp Pro
                965                 970                 975

Ser Arg Pro Gly Gly Arg Cys Gln Leu Cys Glu Cys Ser Gly Asn Ile
                980                 985                 990

Asp Pro Met Asp Pro Asp Ala Cys Asp Pro His Pro Gly Gln Cys Leu
        995                 1000                1005

Arg Cys Leu His His Thr Glu Gly Pro His Cys Ala His Ser Lys Pro
    1010                1015                1020
```

```
Gly Phe His Gly Gln Ala Ala Arg Gln Ser Cys His Arg Cys Thr Cys
1025                1030                1035                1040

Asn Leu Leu Gly Thr Asn Pro Gln Gln Cys Pro Ser Pro Asp Gln Cys
            1045                1050                1055

His Cys Asp Pro Ser Ser Gly Gln Cys Pro Cys Leu Pro Asn Val Gln
        1060                1065                1070

Ala Leu Ala Val Asp Arg Cys Ala Pro Asn Phe Trp Asn Leu Thr Ser
    1075                1080                1085

Gly His Gly Cys Gln Pro Cys Ala Cys Leu Pro Ser Pro Glu Glu Gly
1090                1095                1100

Pro Thr Cys Asn Glu Phe Thr Gly Gln Cys His Cys Leu Cys Gly Phe
1105                1110                1115                1120

Gly Gly Arg Thr Cys Ser Glu Cys Gln Glu Leu His Trp Gly Asp Pro
            1125                1130                1135

Gly Leu Gln Cys His Ala Cys Asp Cys Asp Ser Arg Gly Ile Asp Thr
        1140                1145                1150

Pro Gln Cys His Arg Phe Thr Gly His Cys Thr Cys Arg Pro Gly Val
    1155                1160                1165

Ser Gly Val Arg Cys Asp Gln Cys Ala Arg Gly Phe Ser Gly Ile Phe
1170                1175                1180

Pro Ala Cys His Pro Cys His Ala Cys Phe Gly Asp Trp Asp Arg Val
1185                1190                1195                1200

Val Gln Asp Leu Ala Ala Arg Thr Gln Arg Leu Glu Gln Arg Ala Gln
            1205                1210                1215

Glu Leu Gln Gln Thr Gly Val Leu Gly Ala Phe Glu Ser Ser Phe Trp
        1220                1225                1230

His Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu Glu
1250                1255                1260

Leu Arg Arg Glu Ile Gly Glu Ala Thr Glu His Leu Thr Gln Leu Glu
1265                1270                1275                1280

Ala Asp Leu Thr Asp Val Gln Asp Glu Asn Phe Asn Ala Asn His Ala
            1285                1290                1295

Leu Ser Gly Leu Glu Arg Asp Arg Leu Ala Leu Asn Leu Thr Leu Arg
        1300                1305                1310

Gln Leu Asp Gln His Leu Asp Leu Leu Lys His Ser Asn Phe Leu Gly
    1315                1320                1325

Ala Tyr Asp Ser Ile Arg His Ala His Ser Gln Ser Ala Glu Ala Glu
1330                1335                1340

Arg Arg Ala Asn Thr Ser Ala Leu Ala Val Pro Ser Pro Val Ser Asn
1345                1350                1355                1360

Ser Ala Ser Ala Arg His Arg Thr Glu Ala Leu Met Asp Ala Gln Lys
            1365                1370                1375

Glu Asp Phe Asn Ser Lys His Met Ala Asn Gln Arg Ala Leu Gly Lys
        1380                1385                1390

Leu Ser Ala His Thr His Thr Leu Ser Leu Thr Asp Ile Asn Glu Leu
    1395                1400                1405

Val Cys Gly Ala Gln Gly Leu His His Asp Arg Thr Ser Pro Cys Gly
1410                1415                1420

Gly Ala Gly Cys Arg Asp Glu Asp Gly Gln Pro Arg Cys Gly Gly Leu
1425                1430                1435                1440

Ser Cys Asn Gly Ala Ala Ala Thr Ala Asp Leu Ala Leu Gly Arg Ala
```

-continued

```
               1445                1450                1455

Arg His Thr Gln Ala Glu Leu Gln Arg Ala Leu Ala Glu Gly Gly Ser
               1460                1465                1470

Ile Leu Ser Arg Val Ala Glu Thr Arg Gln Ala Ser Glu Ala Gln
        1475                1480                1485

Gln Arg Ala Gln Ala Ala Leu Asp Lys Ala Asn Ala Ser Arg Gly Gln
        1490                1495                1500

Val Glu Gln Ala Asn Gln Glu Leu Gln Glu Leu Ile Gln Ser Val Lys
1505                1510                1515                1520

Asp Phe Leu Asn Gln Glu Gly Ala Asp Pro Asp Ser Ile Glu Met Val
                1525                1530                1535

Ala Thr Arg Val Leu Glu Leu Ser Ile Pro Ala Ser Ala Glu Gln Ile
            1540                1545                1550

Gln His Leu Ala Gly Ala Ile Ala Glu Arg Val Arg Ser Leu Ala Asp
            1555                1560                1565

Val Asp Ala Ile Leu Ala Arg Thr Val Gly Asp Val Arg Arg Ala Arg
1570                1575                1580

Gln Leu Leu Gln Asp Ala Arg Arg Ala Arg Ser Trp Ala Glu Asp Glu
1585                1590                1595                1600

Lys Gln Lys Ala Glu Thr Val Gln Ala Ala Leu Glu Glu Ala Gln Arg
                1605                1610                1615

Ala Gln Gly Ile Ala Gln Gly Ala Ile Arg Gly Ala Val Ala Asp Thr
            1620                1625                1630

Arg Asp Thr Glu Gln Thr Leu Tyr Gln Val Gln Glu Arg Met Ala Gly
            1635                1640                1645

Ala Glu Arg Ala Leu Ser Ser Ala Gly Glu Arg Ala Arg Gln Leu Asp
            1650                1655                1660

Ala Leu Leu Glu Ala Leu Lys Leu Lys Arg Ala Gly Asn Ser Leu Ala
1665                1670                1675                1680

Ala Ser Thr Ala Glu Glu Thr Ala Gly Ser Ala Gln Gly Arg Ala Gln
                1685                1690                1695

Glu Ala Glu Gln Leu Leu Arg Gly Pro Leu Gly Asp Gln Tyr Gln Thr
            1700                1705                1710

Val Lys Ala Leu Ala Glu Arg Lys Ala Gln Gly Val Leu Ala Ala Gln
            1715                1720                1725

Ala Arg Ala Glu Gln Leu Pro Asp Glu Ala Arg Asp Leu Leu Gln Ala
        1730                1735                1740

Ala Gln Asp Lys Leu Gln Arg Leu Gln Glu Leu Glu Gly Thr Tyr Glu
1745                1750                1755                1760

Glu Asn Glu Arg Ala Leu Glu Ser Lys Ala Ala Gln Leu Asp Gly Leu
                1765                1770                1775

Glu Ala Arg Met Arg Ser Val Leu Gln Ala Ile Asn Leu Gln Val Gln
            1780                1785                1790

Ile Tyr Asn Thr Cys Gln
        1795

<210> SEQ ID NO 12
<211> LENGTH: 1170
<212> TYPE: PRT
<213> ORGANISM: Homo sapiens

<400> SEQUENCE: 12

Met Arg Pro Phe Phe Leu Leu Cys Phe Ala Leu Pro Gly Leu Leu His
1               5                   10                  15
```

-continued

```
Ala Gln Gln Ala Cys Ser Arg Gly Ala Cys Tyr Pro Pro Val Gly Asp
             20                  25                  30

Leu Leu Val Gly Arg Thr Arg Phe Leu Arg Ala Ser Ser Thr Cys Gly
             35                  40                  45

Leu Thr Lys Pro Glu Thr Tyr Cys Thr Gln Tyr Gly Glu Trp Gln Met
 50                  55                  60

Lys Cys Cys Lys Cys Asp Ser Arg Gln Pro His Asn Tyr Tyr Ser His
 65                  70                  75                  80

Arg Val Glu Asn Val Ala Ser Ser Gly Pro Met Arg Trp Trp Gln
             85                  90                  95

Ser Gln Asn Asp Val Asn Pro Val Ser Leu Gln Leu Asp Leu Asp Arg
            100                 105                 110

Arg Phe Gln Leu Gln Glu Val Met Met Glu Phe Arg Gly Pro Met Pro
            115                 120                 125

Ala Gly Met Leu Ile Glu Arg Ser Ser Asp Phe Gly Lys Thr Trp Arg
            130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
            195                 200                 205

Gln Glu Val Gly Glu Ile Thr Asn Leu Arg Val Asn Phe Thr Arg Leu
            210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Ser Thr Ala Val
            260                 265                 270

Gln Val His Asp Val Cys Val Cys Gln His Asn Thr Ala Gly Pro Asn
            275                 280                 285

Cys Glu Arg Cys Ala Pro Phe Tyr Asn Asn Arg Pro Trp Arg Pro Ala
290                 295                 300

Glu Gly Gln Asp Ala His Glu Cys Gln Arg Cys Asp Cys Asn Gly His
305                 310                 315                 320

Ser Glu Thr Cys His Phe Asp Pro Ala Val Phe Ala Ala Ser Gln Gly
                325                 330                 335

Ala Tyr Gly Gly Val Cys Asp Asn Cys Arg Asp His Thr Glu Gly Lys
            340                 345                 350

Asn Cys Glu Arg Cys Gln Leu His Tyr Phe Arg Asn Arg Arg Pro Gly
            355                 360                 365

Ala Ser Ile Gln Glu Thr Cys Ile Ser Cys Glu Cys Asp Pro Asp Gly
            370                 375                 380

Ala Val Ala Gly Ala Pro Cys Asp Pro Val Thr Gly Gln Cys Val Cys
385                 390                 395                 400

Lys Glu His Val Gln Gly Glu Arg Cys Asp Leu Cys Lys Pro Gly Phe
                405                 410                 415

Thr Gly Leu Thr Tyr Ala Asn Pro Arg Arg Cys His Arg Cys Asp Cys
            420                 425                 430

Asn Ile Leu Gly Ser Arg Glu Met Pro Cys Asp Glu Glu Ser Gly Arg
```

-continued

```
                435                 440                 445
       Cys Leu Cys Leu Pro Asn Val Val Gly Pro Lys Cys Asp Gln Cys Ala
               450                 455                 460
       Pro Tyr His Trp Lys Leu Ala Ser Gly Gln Gly Cys Glu Pro Cys Ala
       465                 470                 475                 480
       Cys Asp Pro His Asn Ser Leu Ser Pro Gln Cys Asn Gln Phe Thr Gly
                           485                 490                 495
       Gln Cys Pro Cys Arg Glu Gly Phe Gly Gly Leu Met Cys Ser Ala Ala
                       500                 505                 510
       Ala Ile Arg Gln Cys Pro Asp Arg Thr Tyr Gly Asp Val Ala Thr Gly
                   515                 520                 525
       Cys Arg Ala Cys Asp Cys Asp Phe Arg Gly Thr Glu Gly Pro Gly Cys
               530                 535                 540
       Asp Lys Ala Ser Gly Arg Cys Leu Cys Arg Pro Gly Leu Thr Gly Pro
       545                 550                 555                 560
       Arg Cys Asp Gln Cys Gln Arg Gly Tyr Cys Asn Arg Tyr Pro Val Cys
                           565                 570                 575
       Val Ala Cys His Pro Cys Phe Gln Thr Tyr Asp Ala Asp Leu Arg Glu
                       580                 585                 590
       Gln Ala Leu Arg Phe Gly Arg Leu Pro Asn Ala Thr Ala Ser Leu Trp
                   595                 600                 605
       Ser Gly Pro Gly Leu Glu Asp Arg Gly Leu Ala Ser Arg Ile Leu Asp
               610                 615                 620
       Ala Lys Ser Lys Ile Glu Gln Ile Arg Ala Val Leu Ser Ser Pro Ala
       625                 630                 635                 640
       Val Thr Glu Gln Glu Val Ala Gln Val Ala Ser Ala Ile Leu Ser Leu
                           645                 650                 655
       Arg Arg Thr Leu Gln Gly Leu Gln Leu Asp Leu Pro Leu Glu Glu Glu
                       660                 665                 670
       Thr Leu Ser Leu Pro Arg Asp Leu Glu Ser Leu Asp Arg Ser Phe Asn
                   675                 680                 685
       Gly Leu Leu Thr Met Tyr Gln Arg Lys Arg Glu Gln Phe Glu Lys Ile
               690                 695                 700
       Ser Ser Ala Asp Pro Ser Gly Ala Phe Arg Met Leu Ser Thr Ala Tyr
       705                 710                 715                 720
       Glu Gln Ser Ala Gln Ala Ala Gln Gln Val Ser Asp Ser Ser Arg Leu
                           725                 730                 735
       Leu Asp Gln Leu Arg Asp Ser Arg Arg Glu Ala Glu Arg Leu Val Arg
                       740                 745                 750
       Gln Ala Gly Gly Gly Gly Thr Gly Ser Pro Lys Leu Val Ala Leu
                   755                 760                 765
       Arg Leu Glu Met Ser Ser Leu Pro Asp Leu Thr Pro Thr Phe Asn Lys
               770                 775                 780
       Leu Cys Gly Asn Ser Arg Gln Met Ala Cys Thr Pro Ile Ser Cys Pro
       785                 790                 795                 800
       Gly Glu Leu Cys Pro Gln Asp Asn Gly Thr Ala Cys Ala Ser Arg Cys
                           805                 810                 815
       Arg Gly Val Leu Pro Arg Ala Gly Ala Phe Leu Met Ala Gly Gln
                       820                 825                 830
       Val Ala Glu Gln Leu Arg Gly Phe Asn Ala Gln Leu Gln Arg Thr Arg
                   835                 840                 845
       Gln Met Ile Arg Ala Ala Glu Glu Ser Ala Ser Gln Ile Gln Ser Ser
               850                 855                 860
```

-continued

Ala Gln Arg Leu Glu Thr Gln Val Ser Ala Ser Arg Ser Gln Met Glu
865                 870                 875                 880

Glu Asp Val Arg Arg Thr Arg Leu Leu Ile Gln Gln Val Arg Asp Phe
            885                 890                 895

Leu Thr Asp Pro Asp Thr Asp Ala Ala Thr Ile Gln Glu Val Ser Glu
        900                 905                 910

Ala Val Leu Ala Leu Trp Leu Pro Thr Asp Ser Ala Thr Val Leu Gln
    915                 920                 925

Lys Met Asn Glu Ile Gln Ala Ile Ala Ala Arg Leu Pro Asn Val Asp
930                 935                 940

Leu Val Leu Ser Gln Thr Lys Gln Asp Ile Ala Arg Ala Arg Arg Leu
945                 950                 955                 960

Gln Ala Glu Ala Glu Glu Ala Arg Ser Arg Ala His Ala Val Glu Gly
            965                 970                 975

Gln Val Glu Asp Val Val Gly Asn Leu Arg Gln Gly Thr Val Ala Leu
        980                 985                 990

Gln Glu Ala Gln Asp Thr Met Gln Gly Thr Ser Arg Ser Leu Arg Leu
    995                 1000                1005

Ile Gln Asp Arg Val Ala Glu Val Gln Gln Val Leu Arg Pro Ala Glu
1010                1015                1020

Lys Leu Val Thr Ser Met Thr Lys Gln Leu Gly Asp Phe Trp Thr Arg
1025                1030                1035                1040

Met Glu Glu Leu Arg His Gln Ala Arg Gln Gln Gly Ala Glu Ala Val
            1045                1050                1055

Gln Ala Gln Gln Leu Ala Glu Gly Ala Ser Glu Gln Ala Leu Ser Ala
        1060                1065                1070

Gln Glu Gly Phe Glu Arg Ile Lys Gln Lys Tyr Ala Glu Leu Lys Asp
    1075                1080                1085

Arg Leu Gly Gln Ser Ser Met Leu Gly Glu Gln Gly Ala Arg Ile Gln
        1090                1095                1100

Ser Val Lys Thr Glu Ala Glu Glu Leu Phe Gly Glu Thr Met Glu Met
1105                1110                1115                1120

Met Asp Arg Met Lys Asp Met Glu Leu Glu Leu Leu Arg Gly Ser Gln
            1125                1130                1135

Ala Ile Met Leu Arg Ser Ala Asp Leu Thr Gly Leu Glu Lys Arg Val
        1140                1145                1150

Glu Gln Ile Arg Asp His Ile Asn Gly Arg Val Leu Tyr Tyr Ala Thr
    1155                1160                1165

Cys Lys
    1170

<210> SEQ ID NO 13
<211> LENGTH: 1342
<212> TYPE: PRT
<213> ORGANISM: Artificial Sequence
<220> FEATURE:
<223> OTHER INFORMATION: Consensus sequence

<400> SEQUENCE: 13

Met Leu Leu Leu Met Gln Leu Leu Phe Leu Leu Gly Trp Ala Tyr Ser
1               5                   10                  15

Lys Cys Arg Gly Ala Cys Tyr Pro Thr Gly Asp Leu Leu Val Gly Arg
            20                  25                  30

Thr Gly Leu Met Ala Ser Ser Thr Cys Gly Leu Ser Gln Tyr Cys Ile
        35                  40                  45

```
Ser Leu Ala Lys Cys Ile Cys Asp Ser Arg Phe Pro Tyr Asp Pro Tyr
    50                  55                  60

Asp Asn Pro Asn Ser His Ile Glu Asn Val Ser Phe Pro Asp Arg Glu
 65                  70                  75                  80

Lys Lys Trp Trp Gln Ser Glu Asn Gly Asp His Val Ser Ile Gln Leu
                 85                  90                  95

Asp Leu Glu Ala Phe Phe His Leu Ile Met Thr Phe Lys Thr Phe Arg
                100                 105                 110

Pro Ala Ala Met Leu Val Glu Arg Ser Asp Phe Gly Thr Trp Lys Val
                115                 120                 125

Tyr Tyr Phe Ala Asp Cys Ala Ser Phe Pro Ile Ser Gly Gln Gly Val
        130                 135                 140

Asp Ile Val Cys Asp Ser Tyr Ser Asp Ile Glu Pro Ser Thr Gly Gly
145                 150                 155                 160

Glu Val Leu Val Leu Asp Pro Phe Glu Leu Glu Pro Tyr Ser Pro Ile
                165                 170                 175

Gln Leu Ile Thr Asn Leu Arg Ile Asn Phe Thr Lys Leu His Thr Leu
                180                 185                 190

Gly Asp Leu Leu Arg Gln Lys Tyr Tyr Tyr Ala Leu Tyr Glu Met Val
                195                 200                 205

Arg Gly Ser Cys Phe Cys Gly His Ala Ser Glu Cys Ala Pro Met Gly
210                 215                 220

Arg Asp Val Gly Met Val His Gly Gln Cys Val Cys Gln His Asn Thr
225                 230                 235                 240

Asp Gly Pro Asn Cys Glu Arg Cys Lys Asp Phe Tyr Gln Asp Pro Trp
                245                 250                 255

Arg Pro Ala Ala Asp Leu Gln Asn Ala Cys Arg Cys Asn His Ser
                260                 265                 270

Ser Cys His Phe Asp Met Ala Val Tyr Leu Ala Ser Gly Gly Ser Gly
        275                 280                 285

Gly Val Cys Asp Asp Cys Gln His Asn Thr Glu Gly His Cys Glu Arg
290                 295                 300

Cys Arg Pro Phe Tyr Arg Asp Pro Leu Lys Ile Ser Asp Pro Tyr Ala
305                 310                 315                 320

Cys Ile Cys Glu Cys Asp Pro Asp Gly Ser Gly Gly Ile Cys Asp Ser
                325                 330                 335

His Ser Asp Pro Ala Leu Gly Val Ala Gly Gln Cys Cys Lys Glu Asn
                340                 345                 350

Val Glu Gly Cys Asp Gln Cys Lys Pro Gly Phe Tyr Gly Leu Ser Ala
                355                 360                 365

Thr Asp Pro Leu Gly Cys Gln Cys Asp Cys Asn Pro Leu Gly Leu Pro
370                 375                 380

Leu Thr Cys Asp Val Asp Thr Gly Gln Cys Val Thr Gly Ala His
385                 390                 395                 400

Cys Glu Cys Gly Trp Gly Leu Asn Leu His Gly Cys Pro Cys Asp Cys
                405                 410                 415

Asp Ile Gly Gly Ala Ser Asn Val Cys Ser Pro Lys Asn Gly Gln Cys
                420                 425                 430

Glu Cys Arg Pro His Thr Gly Arg Ser Cys Ser Glu Ala Pro Gly Tyr
        435                 440                 445

Phe Phe Ala Pro Leu Tyr Leu Tyr Glu Ala Glu Ala Thr Pro Ala
                450                 455                 460
```

-continued

```
Val His Val Val Glu Pro Val Pro Gly Asn Pro Trp Thr Gly Pro Gly
465                 470                 475                 480

Phe Arg Val Leu Gly Ala Gly Leu Phe Ala Val Asn Asn Ile Pro Phe
                485                 490                 495

Pro Asp Ile Ile Tyr Glu Gln Ser Ala Asp Trp Thr Val Gln Ile Val
                500                 505                 510

Val Pro Gly Gly Ser His Cys Pro Lys Thr Gln Pro Gln Ser Phe Ala
                515                 520                 525

Leu Pro Ala Thr Arg Met Leu Leu Pro Thr Pro Cys Leu Glu Pro Val
530                 535                 540

Gln Tyr Ser Ile Asp Tyr Ser Gln Gln Gly Glu Ser His Ala Ser Leu
545                 550                 555                 560

Asp Ser Leu Leu Ile Pro Gln Ile Asn Ser Leu Glu Asn Phe Cys Ser
                565                 570                 575

Lys Gln Asp Leu Asp Gln Asn Cys Val Glu Ile Ala Ser Ala Met Gly
                580                 585                 590

Val Leu Pro Gly Ala Cys Glu Arg Leu Ile Ile Ser Met Ser Ala Leu
                595                 600                 605

His Asp Gly Ala Ala Cys Lys Cys His Pro Gln Gly Ser Ser Ser Cys
                610                 615                 620

Ser Leu Gly Gly Gln Cys Gln Cys Lys Pro Leu Val Val Gly Arg Cys
625                 630                 635                 640

Cys Asp Arg Cys Gly Ser Tyr Gly His Gly Cys His Pro Cys His Cys
                645                 650                 655

His Pro Gln Gly Ser Lys Asp Thr Val Cys Asp Gln Val Thr Gly Gln
                660                 665                 670

Cys Pro Cys His Gly Val Ser Gly Arg Arg Cys Asp Arg Cys Leu Ala
                675                 680                 685

Gly Tyr Gly Phe Pro Ser Cys His Pro Cys Pro Cys Asn Ala Leu Cys
                690                 695                 700

Asp Pro Glu Thr Gly Ser Cys Asn Cys Gly Phe Thr Thr Gly Arg Asn
705                 710                 715                 720

Cys Glu Arg Cys Ile Gly Tyr Tyr Gly Pro Ser Ser Gly Gln Pro Cys
                725                 730                 735

Arg Pro Cys Cys Pro Asp Pro Ser Ser Asn Tyr Phe Ala His Ser Cys
                740                 745                 750

Tyr Gln Leu Trp Ser Ser Val Ile Cys Asn Cys Leu Gln Gly Tyr Thr
                755                 760                 765

Gly Thr Cys Gly Glu Cys Thr Gly Phe Gly Asn Pro Ile Ser Gly Pro
770                 775                 780

Cys Cys Gln Pro Cys Ala Cys Asn Asn Asn Ile Asp Val Thr Asp Pro
785                 790                 795                 800

Glu Cys Arg Val Thr Gly Glu Cys Leu Arg Cys Leu His Thr Gly Ala
                805                 810                 815

Cys Gln Leu Cys Lys Pro Gly His Tyr Gly Ser Ala Leu Gln Thr Cys
                820                 825                 830

Arg Arg Cys Ser Cys Ala Gly Ser Pro Met Glu Cys Pro Pro Gly Cys
                835                 840                 845

Leu Cys Asp Pro Val Thr Gly Cys Pro Cys Leu Pro Asn Val Thr Gly
                850                 855                 860

Leu Ala Cys Asp Arg Cys Ala Pro Tyr Trp Asn Leu Ser Gly Arg Gly
865                 870                 875                 880

Cys Gln Pro Cys Cys Asp Pro Arg Thr Ser Gln Ser Pro His Cys Asn
```

-continued

```
                885                 890                 895
Gln Phe Thr Gly Gln Cys Pro Cys Gly Phe Gly Gly Arg Thr Cys Ser
                900                 905                 910
Glu Cys Gln Glu Leu Gly Asp Pro Cys Arg Ala Cys Asp Cys Asp Arg
                915                 920                 925
Gly Glu Thr Pro Gln Cys Asp Thr Gly Cys Cys Arg Gly Val Ser Gly
                930                 935                 940
Pro Arg Cys Asp Gln Cys Ala Arg Gly Tyr Ser Gly Phe Pro Cys Pro
945                 950                 955                 960
Cys His Cys Phe Trp Asp Ile Glu Leu Ala Arg Thr Gln Arg Leu Ala
                965                 970                 975
Ala Leu Gly Val Leu Gly Pro Arg Glu Phe Lys Val Ser Glu Ile Glu
                980                 985                 990
Ile Leu Ala Ser Ala Pro Gly Phe Glu Glu Leu Ile Val Thr Glu Gln
                995                 1000                1005
Leu Glu Leu Asp Thr Glu Ser Leu Leu Glu Ser Leu Arg Glu Ala Leu
                1010                1015                1020
Leu Thr Leu Gln Glu Leu Glu Gln Leu Glu Ile Lys Asn Asp Ile Gly
1025                1030                1035                1040
Ala Asp Ser Ile Lys Tyr Gln Ser Ala Glu Ala Glu Arg Val Asn Glu
                1045                1050                1055
Ser Thr Val Ser Ala Arg Asp Arg Leu Glu Asp Met Glu Glu Phe Lys
                1060                1065                1070
Gly Arg Leu Leu Ala Leu Asp Leu Ser Leu Asn Glu Leu Cys Gly Pro
                1075                1080                1085
Gly Cys Pro Pro Cys Gly Gly Ala Leu Cys Arg Asp Gly Arg Lys Cys
                1090                1095                1100
Gly Gly Pro Gly Cys Gly Leu Thr Ala Asn Ala Leu Gln Lys Ala Leu
1105                1110                1115                1120
Arg Ala Leu Ala Val Leu Met Glu Ala Glu Gln Ala Ser Glu Ala Gln
                1125                1130                1135
Ser Ala Gln Leu Leu Lys Asn Ala Ser Arg Gln Asn Asn Glu Glu Leu
                1140                1145                1150
Arg Leu Leu Ile Gln Val Phe Leu Thr Gln Glu Ala Asp Pro Asp Ser
                1155                1160                1165
Ile Glu Val Ala Asn Val Leu Leu Pro Ser Gln Gln Leu Gln Leu
                1170                1175                1180
Ile Gln Glu Arg Val Ser Leu Asp Val Asp Ile Leu Arg Asp Ile Ala
1185                1190                1195                1200
Arg Ala Glu Leu Leu Glu Ala Lys Arg Ala Arg Ala Asp Val Lys Ala
                1205                1210                1215
Val Ala Leu Glu Ala Gln Ala Gln Gly Ala Gln Ile Ala Ala Asp Ile
                1220                1225                1230
Arg Gln Gln Val Thr Ala Glu Leu Ser Ala Gln Arg Ser Leu Glu Leu
                1235                1240                1245
Glu Glu Leu Lys Lys Ala Ala Gln Asn Ser Glu Ala Val Ala Glu Ala
                1250                1255                1260
Glu Ser Ala Gln Gln Ala Ser Ala Glu Lys Gly Glu Leu Lys Tyr Ala
1265                1270                1275                1280
Lys Leu Lys Thr Leu Ala Arg Lys Ala Glu Gln Leu Lys Asp Glu Ala
                1285                1290                1295
Glu Leu Leu Gly Lys Leu Gln Arg Leu Lys Asp Leu Glu Arg Lys Tyr
                1300                1305                1310
```

```
-continued

Glu Asp Asn Arg Ala Leu Glu Lys Ala Ala Gln Leu Gly Leu Glu Arg
         1315                1320                1325

Val Arg Ser Ile Leu Ile Asn Gln Val Tyr Ala Thr Cys Ser
         1330                1335            1340
```

LAMININS AND USES THEREOF

CROSS-REFERENCE TO RELATED APPLICATIONS

This application is a continuation-in-part and claims benefit from U.S. application Ser. No. 09/168,949, filed Oct. 9, 1998, now abandoned which application claims benefit from U.S Provisional Application Ser. No. 60/061,609, filed Oct. 10, 1997.

BACKGROUND OF THE INVENTION

The invention relates to the laminin 12, laminin subunit γ3, and laminin subunit β1, and methods of making and using these molecules.

SUMMARY OF THE INVENTION

The present invention is based, in part, on the discovery of a novel member of the laminin family, laminin 12. Accordingly, the present invention features a purified or isolated preparation or a recombinant preparation of laminin 12 which includes an α2 subunit, a β1 subunit and a γ3 subunit.

In a preferred embodiment, the α2 subunit has at least 60% to about 70%, more preferably at least about 80%, even more preferably at least about 90% to about 95%, and most preferably at least about 99% sequence identity with human α2 subunit, e.g., the human α2 subunit of SEQ ID NO:7. The α2 subunit can be identical to a human α2 sequence, e.g., that of SEQ ID NO:7. In another embodiment, the α2 subunit is encoded by a nucleic acid molecule which hybridizes under stringent conditions to a nucleic acid molecule of the nucleic acid sequence shown in SEQ ID NO:8. In addition, the α2 subunit can have substantially the same electrophoretic mobility as human α2 subunit, e.g., it appears as a 205 kDa electrophoretic band on reducing gels. Yet another preferred embodiment of the invention features an α2 subunit which is reactive with an α2-specific antibody, e.g., an antibody which binds to the epitope recognized by mAb 5H2. α2 specific antibodies can be made by methods known in the art.

Another preferred embodiment of the invention features a β1 subunit having at least 60% to about 70%, more preferably at least about 80%, even more preferably at least about 90% to about 95%, and most preferably at least about 99% sequence identity with human β1 subunit, e.g., the human β1 subunit of SEQ ID NO:9. Preferably, the β1 subunit has the identical amino acid sequence of human β1 subunit, e.g., that of SEQ ID NO:9. In another embodiment, the β1 subunit is encoded by a nucleic acid molecule which hybridizes under stringent conditions to a nucleic acid molecule of the nucleic acid sequence shown in SEQ ID NO:10. In addition, the β1 subunit can have substantially the same electrophoretic mobility as human β1 subunit, e.g., it appears as a 185 kDa electrophoretic band on reducing gels. Yet another preferred embodiment of the invention features an β1 subunit which is reactive with an β1-specific antibody, e.g., an antibody which binds to the epitope recognized by mAb 545. β1-specific antibodies can be made by methods known in the art.

In yet another preferred embodiment, the γ3 subunit of laminin 12 has at least 60% to about 70%, more preferably at least about 80%, even more preferably at least about 90% to about 95%, and most preferably at least about 99% sequence identity with human γ3 subunit, e.g., the γ3 subunit of SEQ ID NO:3. The γ3 subunit can be identical to a naturally occurring human γ3 subunit, e.g., that of SEQ ID NO:3. In another embodiment, the γ3 subunit is encoded by a nucleic acid molecule which hybridizes under stringent conditions to a nucleic acid molecule of the nucleic acid sequence shown in SEQ ID NO:4. In addition, the γ3 subunit can have substantially the same electrophoretic mobility as human γ3 subunit, e.g., it appears as a 170 kDa electrophoretic band on reducing gels. Yet another preferred embodiment of the invention features an γ3 subunit which is reactive with an γ3-specific antibody. γ3-specific antibodies can be made by methods known in the art and taught herein.

In a preferred embodiment, the laminin 12 is a trimer which can be found in, or can be isolated from human placental chorionic villi. In another embodiment, the laminin 12 is expressed by a recombinant cell, e.g., a bacterial cell, a cultured cell (e.g., a cultured eukaryotic cell) or a cell of a non-human transgenic animal. Cultured cells can include CHO cells or SF8 cells. Expression of laminin 12 in a transgenic animal can be general or can be under the control of a tissue specific promoter. Preferably, one or more sequences which encode subunits of the laminin 12 trimer are expressed in a preferred cell-type by a tissue specific promoter, e.g., a milk specific promoter.

The present invention is also based, in part, on the discovery of a novel laminin subunit, γ3. Accordingly, the invention features a recombinant or substantially pure or isolated preparation of a γ3 polypeptide.

In a preferred embodiment, the γ3 polypeptide has the following biological acitivities: 1) it promotes adhesion between tissue elements; 2) provides a site for insertion of nerves into the basement membrane. In other preferred embodiments: the γ3 polypeptide includes an amino acid sequence with at least 60%, 80%, 90%, 95%, 98%, or 99% sequence identity to an amino acid sequence from SEQ ID NO:3; the γ3 polypeptide includes an amino acid sequence essentially the same as the amino acid sequence in SEQ ID NO:3; the γ3 polypeptide is at least 5, 10, 20, 50, 100, or 150 amino acids in length; the γ3 polypeptide includes at least 5, preferably at least 10, more preferably at least 20, most preferably at least 50, 100, or 150 contiguous amino acids from SEQ ID NO:3; the γ3 polypeptide is either, an agonist or an antagonist, of a biological activity of a naturally occurring γ3 subunit; the γ3 polypeptide is a vertebrate, e.g., a mammalian, e.g. a primate, e.g., a human, γ3 polypeptide.

In a preferred embodiment, the invention includes a γ3 polypeptide encoded by a DNA insert of a plasmid deposited with ATCC as Accession No: 209357. In another embodiment, the γ3 polypeptide is a polypeptide encoded by nucleotide sequences of the overlapping DNA inserts of more than one, preferably all seven of the plasmids deposited with ATCC as Accession No:209357.

In preferred embodiments: the γ3 polypeptide is encoded by the nucleic acid in SEQ ID NO:4, or by a nucleic acid having at least about 85%, more preferably at least about 90% to about 95%, and most preferably at least about 99% sequence identity with the nucleic acid from SEQ ID NO:4.

In preferred embodiments, the γ3 polypeptide includes a nidogen-binding domain. Generally, the nidogen-binding domain is at least 5 residues in length and preferably, has about 70, 80, 90, or 95% sequence identity with the nidogen-binding domain of the protein shown in SEQ ID NO: 3 (amino acid residues 750–755). In another embodiment, the γ3 polypeptide includes at least 5, preferably 6 to 7, and most preferably 8 of the cysteins found in native γ3 protein. In yet another embodiment of the invention features a γ3 polypeptide that does not include or has an inactivated nidogen-binding domain which serves as an antagonist to γ3 biological activities. Furthermore, a γ3 polypeptide which has antagonist activity can have inactivated or excluded regions which comprise at least one cystein found in native γ3 protein.

In a preferred embodiment, the γ3 polypeptide differs in amino acid sequence at up to 1, 2, 3, 5, or 10 residues, from a sequence in SEQ ID NO: 3. In other preferred embodiments, the γ3 polypeptide differs in amino acid sequence at up to 1, 2, 3, 5, or 10% of the residues from a sequence in SEQ ID NO: 3. Preferably, the differences are such that: the γ3 polypeptide exhibits a γ3 biological activity, e.g., the 73 polypeptide retains a biological activity of a naturally occurring γ3 subunit.

In preferred embodiments the γ3 polypeptide includes a γ3 subunit sequence described herein as well as other N-terminal and/or C-terminal amino acid sequence.

In preferred embodiments, the γ3 polypeptide includes all or a fragment of an amino acid sequence from SEQ ID NO: 3, fused, in reading frame, to additional amino acid residues, preferably to residues encoded by genomic DNA 5' to the genomic DNA which encodes a sequence from SEQ ID NO: 3.

In yet other preferred embodiments, the γ3 polypeptide is a recombinant fusion protein having a first γ3 portion and a second polypeptide portion, e.g., a second polypeptide portion having an amino acid sequence unrelated to γ3. The second polypeptide portion can be, e.g., any of glutathione-S-transferase, a DNA binding domain, or a polymerase activating domain. In preferred embodiment the fusion protein can be used in a two-hybrid assay.

In a preferred embodiment the γ3 polypeptide includes amino acid residues 750–755 of SEQ ID NO:3. In another embodiment, the γ3 polypeptide encodes domains IV–VI of the γ3 subunit.

In preferred embodiments the γ3 polypeptide has antagonistic activity, and is capable of: inhibiting adhesion between connective tissues.

In a preferred embodiment, the γ3 polypeptide is a fragment of a naturally occurring γ3 which inhibits connective tissue adhesion.

Polypeptides of the invention include those which arise as a result of the existence of multiple genes, alternative transcription events, alternative RNA splicing events, and alternative translational and postranslational events. The γ3 polypeptide can be expressed in systems, e.g., cultured cells, which result in substantially the same postranslational modifications present when expressed γ3 is expressed in a native cell, or in systems which result in the omission of postranslational modifications present when expressed in a native cell.

The invention includes an immunogen which includes a γ3 polypeptide in an immunogenic preparation, the immunogen being capable of eliciting an immune response specific for the γ3 polypeptide, e.g., a humoral response, an antibody response, or a cellular response. In preferred embodiments, the immunogen comprising an antigenic determinant, e.g., a unique determinant, from a protein represented by SEQ ID NO: 3.

The present invention also includes an antibody preparation specifically reactive with an epitope of the γ3 immunogen or generally of a γ3 polypeptide, preferably an epitope which consists all or in part of residues from the the amino acid sequence of SEQ ID NO:3, or an epitope, which when bound to an antibody, results in the modulation of a biological activity.

In preferred embodiments the γ3-like polypeptide, as expressed in the cells in which it is normally expressed or in other eukaryotic cells, has a molecular weight of 170 kDa as determined by SDS-PAGE.

In another embodiment, the γ3 polypeptide comprises amino acid residues 100–1761 of SEQ ID NO: 3.

In a preferred embodiment, the γ3 polypeptide has one or more of the following characteristics:
(i) it has the ability to promote adhesion between connective tissues;
(ii) it has a niolecular weight, amino acid composition or other physical characteristic of γ3 subunit of SEQ ID NO:3;
(iii) it has an overall sequence similarity of at least 50%, preferably at least 60%, more preferably at least 70, 80, 90, or 95%, with a γ3 polypeptide of SEQ ID NO:3;
(iv) it can be isolated from human placenta chorionic villi;
(v) it has a nidogen-binding domain which is preferably about 70%, 80%, 90% or 95% with amino acid residues 750–755 of SEQ ID NO:3;
(vi) it can colocalize with protein ubiquitin carboxy terminal hydroxylase I;
(vii) it has at least 5, preferably 6 or 7, and most preferably 8 of the cysteins found amino acid sequence of native γ3.

Also included in the invention is a composition which includes a γ3 polypeptide (or a nucleic acid which encodes it) and one or more additional components, e.g., a carrier, diluent, or solvent. The additional component can be one which renders the composition useful for in vitro and in vivo pharmaceutical or veterinary use.

In another aspect, the invention provides an isolated or substantially pure nucleic acid having or comprising a nucleotide sequence which encodes a γ3 polypeptide, e.g., a γ3 polypeptide described herein.

A preferred embodiment of the invention features a nucleic acid molecule having a nucleotide sequence at least about 85% sequence identity to a nucleotide sequence of SEQ ID NO:4. In other preferred embodiments, the γ3 polypeptide is encoded by a nucleic acid molecule having a nucleotide sequence with at least about 90% to about 95%, and more preferably about 98% to about 99% sequence identity to the nucleotide sequence from SEQ ID NO:4. In another preferred embodiment, the γ3 polypeptide is encoded by the nulceic acid molecule of SEQ ID NO:4.

In preferred embodiments, the isolated nucleic acid molecule includes the nucleotide sequence of at least one and preferably all of the DNA inserts of the plasmids deposited with ATCC as Accession No: 209357.

In preferred embodiments, the subject γ3 nucleic acid will include a transcriptional regulatory sequence, e.g. at least one of a transcriptional promoter or transcriptional enhancer sequence, operably linked to the γ3 gene sequence (also referred to as LAMG3), e.g., to render the γ3 gene sequence suitable for use as an expression vector.

In yet a further preferred embodiment, the nucleic acid which encodes a γ3 polypeptide of the invention, hybridizes under stringent conditions to a nucleic acid probe corresponding to at least 12 consecutive nucleotides of SEQ ID NO:4. More preferably, the nucleic acid probe corresponds to at least 20 consecutive nucleotides from SEQ ID NO: 4.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO: 4, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a γ3 polypeptide of the invention. This includes double stranded nucleic acids as well as coding and anti-sense single strands.

In another aspect, the invention features a cell or purified preparation of cells which include a γ3 subunit transgene, or which otherwise misexpress a γ3 gene. The cell preparation can consist of human or non human cells, e.g., rodent cells, e.g., mouse or rat cells, rabbit cells, or pig cells. In preferred embodiments, the cell or cells include a γ3 transgene, e.g., a heterologous form of a γ3 gene, e.g., a gene derived from humans (in the case of a non-human cell). The γ3 transgene can be misexpressed, e.g., overexpressed or underexpressed. In other preferred embodiments, the cell or cells include a gene which misexpress an endogenous γ3 gene, e.g., a gene the expression of which is disrupted, e.g., a knockout. Such cells can serve as a model for studying disorders which are related to mutated or mis-expressed γ3 alleles or for use in drug screening.

In another aspect, the invention features a transgenic γ3 animal, e.g., a rodent, e.g., a mouse or a rat, a rabbit, a pig, a goat, or a cow. In preferred embodiments, the transgenic animal includes (and preferably express) a heterologous form of a γ3 gene, e.g., a gene derived from humans. In a further embodiment, the γ3 transgene includes a tissue specific promoter, e.g., a milk-specific promoter. In other preferred embodiments, the animal has an endogenous γ3 gene which is misexpressed, e.g., a knockout. Such a transgenic animal can serve as a model for studying disorders which are related to mutated or mis-expressed γ3 alleles or for use in drug screening.

The invention is also based, in part, on the discovery of a novel laminin subunit, β4. Accordingly, the invention features a recombinant or substantially pure preparation of a β4 polypeptide.

In preferred embodiment, the β4 polypeptide has the following biological activities: 1) it promotes adhesion between tissue elements; 2) it aids in wound healing. In other preferred embodiments: the β4 polypeptide includes an amino acid sequence with at least 65%, 80%, 90%, 95%, 98%, or 99% sequence identity to an amino acid sequence from SEQ ID NO: 1; the β4 polypeptide includes an amino acid sequence essentially the same as an amino acid sequence in SEQ ID NO: 1; the β4 polypeptide is at least 5, 10, 20, 50, 100, or 150 amino acids in length; the β4 polypeptide includes at least 5, preferably at least 10, more preferably at least 20, most preferably at least 50, 100, or 150 contiguous amino acids from SEQ ID NO: 1; the β4 polypeptide is either, an agonist or an antagonist, of a biological activity of a naturally occurring β4 subunit; the β4 polypeptide is a vertebrate, e.g., a mammalian, e.g. a primate, e.g., a human, β4 polypeptide.

In preferred embodiments: the β4 polypeptide is encoded by the nucleic acid in SEQ ID NO:2, or by a nucleic acid having at least about 65% to about 70%, more preferably at least 80%, even more preferably at least about 90% to about 95%, and most preferably about 99% sequence identity with the nucleic acid from SEQ ID NO: 2.

In preferred embodiments, the β4 polypeptide includes domains VI and V found in native β4 subunits. Amino acid residues from about 221–262 and 263–535 of SEQ ID NO: 1 are exemplary of domains VI and V, respectively, of β4. Generally, domain VI is at least 33 residues in length and has preferably at least about 60%, more preferably about 70% to about 80%, and most preferably about 90% to about 95% sequence identity with the amino acid residues 221–262 of the β4 protein shown in SEQ ID NO: 1. Domain V is at least 272 residues in length and has preferably at least about 60%, more preferably about 70% to about 80%, and most preferably about 90% to about 95% sequence identity with the amino acid residues 263–535 of the β4 protein shown in SEQ ID NO: 1. In another embodiment, the β4 polypeptide has at least 5, preferably 6 or 7, and most preferably 8 cysteins as found in native β4. In yet another embodiment, a β4 polypeptide which has antagonist activity has inactivated or excluded regions which comprise at least one of the cysteins found in native β4 protein.

In a preferred embodiment, the β4 polypeptide differs in amino acid sequence at up to 1, 2, 3, 5, or 10 residues, from a sequence in SEQ ID NO: 1. In other preferred embodiments, the β4 polypeptide differs in amino acid sequence at up to 1, 2, 3, 5, or 10% of the residues from a sequence in SEQ ID NO: 1. Preferably, the differences are such that: the β4 polypeptide exhibits a β4 biological activity, e.g., the β4 polypeptide retains a biological activity of a naturally occurring β4 subunit.

In preferred embodiments the β4 polypeptide includes a β4 sequence described herein as well as other N-terminal and/or C-terminal amino acid sequence.

In preferred embodiments, the β4 polypeptide includes all or a fragment of an amino acid sequence from SEQ ID NO: 1, fused, in reading frame, to additional amino acid residues, preferably to residues encoded by genomic DNA 5' to the genomic DNA which encodes a sequence from SEQ ID NO:1.

In yet other preferred embodiments, the β4 polypeptide is a recombinant fusion protein having a first β4 portion and a second polypeptide portion, e.g., a second polypeptide portion having an amino acid sequence unrelated to β4. The second polypeptide portion can be, e.g., any of glutathione-S-transferase, a DNA binding domain, or a polymerase activating domain. In preferred embodiment the fusion protein can be used in a two-hybrid assay.

In preferred embodiments the β4 polypeptide has antagonistic activity, and is capable of: inhibiting the adhesion of connective tissues.

Preferably, the β4 polypeptide is a fragment of a naturally occurring β4 which inhibits connective tissue adhesion.

Polypeptides of the invention include those which arise as a result of the existence of multiple genes, alternative transcription events, alternative RNA splicing events, and alternative translational and postranslational events. In one aspect of the invention, the β4 polypeptide is a splice variant of the β4 subunit. In another preferred embodiment, the β4 splice variant is encoded by a nucleic acid molecule identical to the nucleotide sequence of SEQ ID NO:6. The polypeptide can be expressed in systems, e.g., cultured cells, which result in substantially the same postranslational modifications present when expressed β4 is expressed in a native cell, or in systems which result in the omission of postranslational modifications present when expressed in a native cell.

The invention includes an immunogen which includes a β4 polypeptide in an immunogenic preparation, the immunogen being capable of eliciting an immune response specific for the β4 polypeptide, e.g., a humoral response, an antibody response, or a cellular response. In preferred embodiments, the immunogen comprising an antigenic determinant, e.g., a unique determinant, from a protein represented by SEQ ID NO: 1.

The present invention also includes an antibody preparation specifically reactive with an epitope of the β4 immunogen or generally of a β4 polypeptide, preferably an epitope which consists all or in part of residues from the amino acid sequence of SEQ ID NO: 1, or an epitope, which when bound to an antibody, results in the modulation of a biological activity.

In preferred embodiments the β4-like polypeptide, as expressed in the cells in which it is normally expressed or in other eukaryotic cells, has an estimated molecular weight of 200 kDa as determined by SDS-PAGE.

In a preferred embodiment, the β4 polypeptide has one or more of the following characteristics:

(i) it has the ability to promote adhesion between connective tissues;
(ii) it has a molecular weight, amino acid composition or other physical characteristic of β4 subunit of SEQ ID NO: 1;
(iii) it has an overall sequence similarity of at least 50%, preferably at least 65%, more preferably at least 70, 80, 90, or 95%, with a β4 polypeptide of SEQ ID NO: 1;
(iv) it can be isolated from human placenta chorionic villi;
(v) it can associate with α3 or γ2 subunits;
(vi) it has coiled coils in domains I and II.
(vii) it has at least 5, preferably 6 or 7, and most preferably 8 of the cysteins found in native β4 sequence.

Also included in the invention is a composition which includes a β4 polypeptide (or a nucleic acid which encodes it) and one or more additional components, e.g., a carrier, diluent, or solvent. The additional component can be one which renders the composition for in vitro and in vivo pharmaceutical or veterinary use. Such uses can include aiding in wound healing or promotion of the adhesion of dermal and epidermal cells.

In another aspect, the invention provides an isolated or substantially pure nucleic acid having or comprising a nucleotide sequence which encodes a β4 polypeptide, e.g., a β4 polypeptide described herein.

A preferred embodiment of the invention features a nucleic acid molecule having a nucleotide sequence at least about 65% sequence identity to a nucleotide sequence of SEQ ID NO:2. In other preferred embodiments, the β4 polypeptide is encoded by a nucleic acid molecule having a nucleotide sequence with at least 70%, preferably 80%, more preferably about 90% to about 95%, and even more preferably about 99% sequence identity to the nucleotide sequence from SEQ ID NO:2. In another preferred embodiment, the β4 polypeptide is encoded by the nulceic acid molecule of SEQ ID NO:2.

In preferred embodiments, the subject β4 nucleic acid will include a transcriptional regulatory sequence, e.g. at least one of a transcriptional promoter or transcriptional enhancer *sequence, operably linked to the β4 gene sequence (also referred to as LAMB4), e.g., to render the β4 gene sequence suitable for use as an expression vector.

In yet a further preferred embodiment, the nucleic acid which encodes a β4 polypeptide of the invention, hybridizes under stringent conditions to a nucleic acid probe corresponding to at least 12 consecutive nucleotides from SEQ ID NO:2, more preferably to at least 20 consecutive nucleotides from SEQ ID NO:2.

In a preferred embodiment, the nucleic acid differs by at least one nucleotide from a nucleotide sequence of SEQ ID NO:2, nucleotides 4686–5870.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO: 2, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a β4 polypeptide of the invention. This includes double stranded nucleic acids as well as coding and antisense single strands.

In another aspect, the invention features a cell or purified preparation of cells which include a β4 transgene, or which otherwise misexpress a β4 gene. The cell preparation can consist of human or non human cells, e.g., rodent cells, e.g., mouse or rat cells, rabbit cells, or pig cells. In preferred embodiments, the cell or cells include a β4 transgene, e.g., a heterologous form of a β4 gene, e.g., a gene derived from humans (in the case of a non-human cell). The β4 transgene can be misexpressed, e.g., overexpressed or underexpressed. In other preferred embodiments, the cell or cells include a gene which misexpress an endogenous β4 gene, e.g., a gene the expression of which is disrupted, e.g., a knockout. Such cells can serve as a model for studying disorders which are related to mutated or mis-expressed β4 alleles or for use in drug screening.

In another aspect, the invention features a transgenic β4 animal, e.g., a rodent, e.g., a mouse or a rat, a rabbit, a pig, a goat, or a cow. In preferred embodiments, the transgenic animal includes (and preferably express) a heterologous form of a β4 gene, e.g., a gene derived from humans. In a further embodiment, the β4 transgene includes a tissue specific promoter, e.g., a milk-specific promoter. In other preferred embodiments, the animal has an endogenous β4 gene which is misexpressed, e.g., a knockout. Such a transgenic animal can serve as a model for studying disorders which are related to mutated or mis-expressed β4 alleles or for use in drug screening.

In another aspect, the invention features, a method of promoting adhesion of a first tissue element to a second tissue element. The method includes contacting one or both of the first tissue element and the second tissue element with an amount of a laminin molecule described herein, e.g., laminin 12, or γ3 (or a laminin trimer which includes γ3), sufficient to promote adhesion. The method can be performed in vivo, or in vitro. In in vivo methods the laminin is administered to the subject. The administration can be directed to the site where adhesion is desired, e.g., by topical application or by injection, or administered in a systemic fashion.

A tissue element can be a cell or a multi-cellular on acellular structure. Examples of tissue elements include, skin cells, e.g., epidermal or dermal cells, neuronal cells, e.g., nerve cells, retinal cells, central or pereipheral nervous system components, basement membrane or components of the basement membrane, or any cell or structure which in normal, non-traumatized, or non-diseased tissue is adjacent or adhered to a specific tissue element recited herein.

In preferred embodiments the molecule is exogenous (e.g., administered to a subject) or is recombinant.

In preferred embodiments the method is an vivo method. In vivo methods can be autologous, allogeneic, or xenogeneic. In autologous methods, adhesion between two tissue elements from the subject is promoted. In allogeneic methods, adhesion between a recipient tissue element and a donor tissue element from an allogeneic donor is promoted. In xenogeneic methods, adhesion between a recipient tissue element and a donor tissue element from a xenogeneic donor is promoted. Thus, one element can be a donor tissue element which is implanted into a recipient subject.

In preferred embodiments the first tissue is healthy tissue, e.g., skin tissue, and the second tissue is wounded, e.g., burned, diseased, traumatized, cut, and the tissue, or is a wound bed. For example, the first tissue is skin tissue, from the subject or from a donor, and the second tissue is wounded, e.g., burned or abraided tissue.

In preferred embodiments the first tissue and second tissue element are normally adhered but have become detached from one another due to trauma, burn or other physical injury, disease, or age.

In preferred embodiments: the first tissue element is a dermal cell and the second tissue element is an epidermal cell; the first tissue element is a nerve cell or nerve and the second tissue element is a cell or structure which in normal, non-traumatized, or non-diseased tissue is adjacent or adhered to the nerve cell or nerve; the first tissue element is a retinal cell or retina tissue and the second tissue element is a cell or structure which in normal, non-traumatized, or non-diseased tissue is adjacent or adhered to the a retinal cell or retina tissue, the first tissue is a nerve and the second tissue is basement membrane.

The administration of laminin can be repeated.

In another aspect, the invention features a method of promoting wound healing in a subject. The method includes administering an amount of a laminin molecule described herein, e.g., laminin 12, γ3 (or a laminin trimer which includes γ3), sufficient to promote healing to the wound. The administration can be directed to the site where healing is desired, e.g., by topical appication or by injection, or administered in a systemic fashion.

The wound can be in any tissue, but preferably ina tissue in which the laminin normally occurs. Examples skin, central or peripheral nervous tissue, tissues of the eye, e.g., the retinal, the basement membrane, or any tissue which in normal, non-traumatized, or non-diseased tissue is adjacent or adhered thereto.

In preferred embodiments the molecule is exogenous (e.g., administered to a subject) or is recombinant.

In preferred embodiments the wound tissue is burned, diseased, traumatized, cut, the subject of immune attack, e.g, autoimmune attack, or abraided.

The administration of laminin can be repeated.

In another aspect, the invention feature's a method of promoting nerve growth or regeneration in a subject. The method includes administering an amount of a laminin molecule described herein, e.g., laminin 12, or γ3 (or a laminin trimer which includes γ3), sufficient to promote nerve growth or regeneration. The administration can be directed to the site where nerve growth or regeneration is desired, e.g., by topical appication or by injection, or administered in a systemic fashion.

In preferred embodiments the molecule is exogenous (e.g., administered to a subject) or is recombinant.

In preferred embodiments the nerve growth or regeneration is promoted at a wound site.

The administration of laminin can be repeated.

In another aspect, the invention provides, a method of determining if a subject is at risk for a disorder related to a lesion in or the misexpression of a gene which encodes a laminin described herein, e.g., γ3 or laminin 12.

Such disorders include, e.g., a disorder associated with the misexpression of a laminin e.g., laminin 12, or misexpression of the γ3 subunit; a disorder of the central or peripheral nervous system; a disorder associated with a genetic lesion at chromosome 9, region q31–34; Fukuyama-type muscular dystrophy; muscle-eye-brain disease; Walker-Warburg Syndrome (hydrocephalus, ageria, and retinal displasia); a retinal disorder, e.g, retinitis pigmentosa-deafness syndrome (which may be a subtype of Walker-Warburg Syndrome); a disorder associated with abnormal levels, e.g., abnormally low levels, of adhesion between tissues; a disorder associated with the basement membrane; a skin disorder, e.g., an epidermal or dermal, disorder; a disorder associated with the testis, spleen, placenta, thymus, ovary, small intestine, lung, or liver.

The method includes one or more of the following:
detecting, in a tissue of the subject, the presence or absence of a mutation which affects the expression of the γ3 gene, or other gene which encodes a subunit of laminin 12, e.g., detecting the presence or absence of a mutation in a region which controls the expression of the gene, e.g., a mutation in the 5' control region;

detecting, in a tissue of the subject, the presence or absence of a mutation which alters the structure of the γ3 gene, or other gene which encodes a subunit of laminin 12;

detecting, in a tissue of the subject, the misexpression of the γ3 gene, or other gene which encodes a subunit of laminin 12 at the mRNA level, e.g., detecting a non-wild type level of a γ3, or an other laminin 12 subunit mRNA; detecting, in a tissue of the subject, the misexpression of the γ3 gene, or other gene which encodes a subunit of laminin 12, at the protein level, e.g., detecting a non-wild type level of a γ3, or an other laminin 12 subunit polypeptide.

In preferred embodiments the method includes: ascertaining the existence of at least one of: a deletion of one or more nucleotides from the γ3 gene, or other gene which encodes a subunit of laminin 12; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:4, or naturally occurring mutants thereof or 5' or 3' flanking sequences naturally associated with the LAMG3 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the γ3 gene, or other gene which encodes a subunit of laminin 12; the presence of a non-wild type splicing pattern of a messenger RNA transcript of the γ3 gene, or other gene which encodes a subunit of laminin 12; or a non-wild type level of γ3, or other subunit of laminin 12.

Methods of the invention can be used prenatally or to determine if a subject's offspring will be at risk for a disorder.

In preferred embodiments the method includes determining the structure of a γ3 gene, or other gene which encodes a subunit of laminin 12, an abnormal structure being indicative of risk for the disorder.

In preferred embodiments the method includes contacting a sample form the subject with an antibody to the laminin protein or a nucleic acid which hybridizes specifically with the γ3 gene, or other gene which encodes a subunit of laminin 12.

In another aspect, the invention features, a method of promoting adhesion of a first tissue element to a second tissue element. The method includes contacting one or both of the first tissue element and the second tissue element with an amount of a laminin molecule described herein, e.g., β4, sufficient to promote adhesion. The method can be performed in vivo, or in vitro. In in vivo methods the laminin is administered to the subject. The administration can be directed to the site where adhesion is desired, e.g., by topical application or by injection, or administered in a systemic fashion.

A tissue element can be a cell or a multi-cellular on acellular structure. Examples of tissue elements include, skin cells, e.g., epidermal or dermal cells, neuronal cells, e.g., nerve cells, retinal cells, central or pereipheral nervous system components, basement membrane or components of the basement membrane, or any cell or structure which in normal, non-traumatized, or non-diseased tissue is adjacent or adhered to a specific tissue element recited herein.

In preferred embodiments the molecule is exogenous (e.g., administered to a subject) or is recombinant.

In preferred embodiments the method is an vivo method. In vivo methods can be autologous, allogeneic, or xenogeneic. In autologous methods, adhesion between two tissue elements from the subject is promoted. In allogeneic methods, adhesion between a recipient tissue element and a donor tissue element from an allogeneic donor is promoted. In xenogeneic methods, adhesion between a recipient tissue element and a donor tissue element from a xenogeneic donor is promoted. Thus, one element can be a donor tissue element which is implanted into a recipient subject.

In preferred embodiments the first tissue is healthy tissue, e.g., skin tissue, and the second tissue is wounded, e.g., burned, diseased, traumatized, cut, and the tissue, or is a wound bed. For example, the first tissue is skin tissue, from the subject or from a donor, and the second tissue is wounded, e.g., burned or abraided tissue.

In preferred embodiments: the first tissue element is a dermal cell and the second tissue element is an epidermal cell; the first tissue element is a nerve cell or nerve and the second tissue element is a cell or structure which in normal, non-traumatized, or non-diseased tissue is adjacent or adhered to the nerve cell or nerve; the first tissue is a nerve and the second tissue is basement membrane.

The administration of laminin can be repeated.

In another aspect, the invention features a method of promoting wound healing in a subject. The method includes administering an amount of a laminin molecule described herein, e.g., β4, sufficient to promote healing to the wound. The administration can be directed to the site where healing is desired, e.g., by topical appication or by injection, or administered in a systemic fashion.

The wound can be in any tissue, but preferably in a tissue in which the laminin normally occurs in fetal or adult life. Examples examples include skin the basement membrane.

In preferred embodiments the molecule is exogenous (e.g., administered to a subject) or is recombinant.

In preferred embodiments the wound tissue is burned, diseased, traumatized, cut, the subject of immune attack, e.g, autoimmune attack, or abraded.

The administration of laminin can be repeated.

In another aspect, the invention features a method of promoting tissue growth, development, or regeneration in a subject. The method includes administering an amount of a laminin molecule described herein, e.g., β4, sufficient to promote tissue growth, development, or regeneration in a subject. The administration can be directed to the site where nerve growth or regeneration is desired, e.g., by topical appication or by injection, or administered in a systemic fashion.

In preferred embodiments the molecule is exogenous (e.g., administered to a subject) or is recombinant.

In preferred embodiments the nerve growth or regeneration is promoted at a wound site.

The administration of laminin can be repeated.

In another aspect, the invention provides, a method of determining if a subject is at risk for a disorder related to a lesion in or the misexpression of a laminin molecule described herein, e.g., β4.

Such disorders include, e.g., a disorder associated with the misexpression of a laminin, e.g., β4; a disorder associated with a genetic lesion at chromosome region 7q22–q31.2; a developmetnal disorder; a disorder associated with abnormal levels, e.g., abnormally low levels, of adhesion between tissues; a disorder associated with the basement membrane; a skin disorder, e.g., an epidermal or dermal, disorder.

The method includes one or more of the following:

detecting, in a tissue of the subject, the presence or absence of a mutation which affects the expression of the (4 gene, e.g, detecting the presence or absence of a mutation in a region which controls the expression of the gene, e.g., a mutation in the 5' control region;

detecting, in a tissue of the subject, the presence or absence of a mutation which alters the structure of the β4 gene;

detecting, in a tissue of the subject, the misexpression of the β4 gene, e.g., detecting a non-wild type level of a β4 mRNA;

detecting, in a tissue of the subject, the misexpression of the β4, at the protein level, e.g., detecting a non-wild type level of a β4 polypeptide.

In preferred embodiments the method includes: ascertaining the existence of at least one of: a deletion of one or more nucleotides from the β4; an insertion of one or more nucleotides into the gene, a point mutation, e.g., a substitution of one or more nucleotides of the β4 gene, a gross chromosomal rearrangement of the β4 gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:2, or naturally occurring mutants thereof or 5' or 3' flanking sequences naturally associated with the LAMB4 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments: detecting the misexpression includes ascertaining the existence of at least one of: an alteration in the level of a messenger RNA transcript of the β4; the presence of a non-wild type splicing pattern of a messenger RNA transcript of the β4; or a non-wild type level of β4.

Methods of the invention can be used prenatally or to determine if a subject's offspring will be at risk for a disorder.

In preferred embodiments the method includes determining the structure of the β4, an abnormal structure being indicative of risk for the disorder.

In preferred embodiments the method includes contacting a sample form the subject with an antibody to the β4 protein or a nucleic acid which hybridizes specifically with the β4.

In another aspect, the invention features, a method of evaluating a compound for the ability to interact with, e.g., bind, a subject laminin polypeptide, e.g., laminin 12, γ3, a laminin trimer which includes γ3, β4, or a laminin trimer which includes β4. The method includes: contacting the compound with the subject laminin polypeptide; and evaluating ability of the compound to interact with, e.g., to bind or form a complex with the subject laminin polypeptide. This method can be performed in vitro, e.g., in a cell free system or in vivo, e.g., in a two-hybrid interaction trap assay. This method can be used to identify naturally occurring molecules which interact with subject laminin polypeptide. It can also be used to find natural or synthetic inhibitors of subject laminin polypeptide.

In another aspect, the invention features, a method of evaluating a compound, e.g., a polypeptide, e.g., a naturally occurring ligand of or a naturally occurring substrate to which binds a subject laminin polypeptide, e.g., of laminin 12, γ3, a laminin trimer which includes γ3, β4, or a laminin trimer which includes β4, for the ability to bind a subject laminin polypeptide. The method includes: contacting the compound with the subject laminin polypeptide; and evaluating the ability of the compound to interact with, e.g., to bind or form a complex with the subject laminin polypeptide, e.g., the ability of the compound to inhibit a subject laminin polypeptide/ligand interaction. This method can be performed in vitro, e.g., in a cell free system, or in vivo, e.g., in a two-hybrid interaction trap assay. This method can be used to identify compounds, e.g., fragments or analogs of a subject laminin polypeptide, which are agonists or antagonists of a subject laminin polypeptide.

In another aspect, the invention features, a method of evaluating a first compound, e.g., a subject laminin polypeptide, e.g., laminin 12, γ3, a laminin trimer which includes γ3, β4, or a laminin trimer which includes β4, for the ability to bind a second compound, e.g., a second polypeptide, e.g., a naturally occurring ligand of or substrate to which binds a subject laminin polypeptide. The method includes: contacting the first compound with the second compound; and evaluating the ability of the first compound to form a complex with the second compound. This method can be performed in vitro, e.g., in a cell free system, or in vivo, e.g., in a two-hybrid interaction trap assay. This method can be used to identify compounds, e.g., fragments or analogs of a subject laminin polypeptide, which are agonists or antagonists of a subject laminin polypeptide.

In yet another aspect, the invention features a method for evaluating a compound, e.g., for the ability to modulate an interaction, e.g., the ability to inhibit an interaction of a subject laminin polypeptide, e.g., of laminin 12, γ3, a laminin trimer which includes γ3, β4, or a laminin trimer which includes β4, with a second polypeptide, e.g., a polypeptide, e.g., a natural ligand which binds a subject laminin polypeptide, or a fragment thereof. The method includes the steps of (i) combining the second polypeptide (or preferably a purified preparation thereof), a subject laminin polypeptide, (or preferably a purified preparation thereof), and a compound, e.g., under conditions wherein in the absence of the compound, the second polypeptide, and the subject laminin polypeptide, are able to interact, e.g., to bind or form a complex; and (ii) detecting the interaction, e.g., detecting the formation (or dissolution) of a complex which includes the second polypeptide, and the subject laminin polypeptide. A change, e.g., a decrease or increase, in the formation of the complex in the presence of a compound (relative to what is seen in the absence of the compound) is indicative of a modulation, e.g., an inhibition or promotion, of the interaction between the second polypeptide, and the subject laminin polypeptide. In preferred embodiments: the second polypeptide, and the subject laminin polypeptide, are combined in a cell-free system and contacted with the compound; the cell-free system is selected from a group consisting of a cell lysate and a reconstituted protein mixture; the subject laminin polypeptide, and the second polypeptide are simultaneously expressed in a cell, and the cell is contacted with the compound, e.g. in an interaction trap assay (e.g., a two-hybrid assay).

In yet another aspect, the invention features a two-phase method (e.g., a method having an in vitro, e.g., in a cell free system, and an in vivo phase) for evaluating a compound, e.g., for the ability to modulate, e.g., to inhibit or promote, an interaction of a subject laminin polypeptide subject laminin polypeptide, e.g., of laminin 12, γ3, a laminin trimer which includes γ3, β4, or a laminin trimer which includes β4, with a second compound, e.g., a second polypeptide, e.g., a naturally occurring ligand of or a substrate to which binds a subject laminin polypeptide, or a fragment thereof. The method includes steps (i) and (ii) of the method described immediately above performed in vitro, and further includes: (iii) determining if the compound modulates the interaction in vitro, e.g., in a cell free system, and if so; (iv) administering the compound to a cell or animal; and (v) evaluating the in vivo effect of the compound on an interaction, e.g., inhibition, of a subject laminin polypeptide, with a second polypeptide.

In another aspect, the invention features, a method of evaluating a compound for the ability to bind a nucleic acid encoding a subject laminin polypeptide, e.g., a laminin 12, γ3, a laminin trimer which includes γ3, p4, or a laminin trimer which includes β4 polypeptide regulatory sequence. The method includes: contacting the compound with the nucleic acid; and evaluating ability of the compound to form a complex with the nucleic acid.

In another aspect, the invention features a method of making a γ3 or β4 polypeptide, e.g., a peptide having a non-wild type activity, e.g., an antagonist, agonist, or super agonist of a naturally occurring γ3 or β4 polypeptide, e.g., a naturally occurring γ3 or β4 polypeptide. The method includes: altering the sequence of a γ3 or β4 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a γ3 or β4 polypeptide having a biological activity of a naturally occurring γ3 or β4 polypeptide. The method includes: altering the sequence, e.g., by substitution or deletion of one or more residues, of a γ3 or ,B4 polypeptide, e.g., altering the sequence of a non-conserved region, or a domain or residue described herein, and testing the altered polypeptide for the desired activity.

In another aspect, the invention features, a human cell, e.g., a hematopoietic stem cell, transformed with nucleic acid which encodes a subject laminin polypeptide, e.g., a laminin 12, γ3, a laminin trimer which includes γ3, β4, or a laminin trimer which includes β4.

In another aspect, the invention includes: a γ3, β4 nucleic acid, e.g., a γ3, β4 nucleic acid inserted into a vector; a cell transformed with a γ3, β4 nucleic acid; a γ3, β4 made by culturing a cell transformed with a γ3, β4 nucleic acid; and a method of making a γ3, β4 polypeptide including culturing a a cell transformed with a γ3, β4 nucleic acid.

The inventors have shown that γ3 forms laminin 12 in association with α2 and β1. However, we are unsure of the chain associations of γ3 within other tissues. It is very likely that γ3 can also associate with γ3, α3, α4, and α5; with β2, β3, β4 and β5. Therefore, our results predict 25 new laminins: laminins 12–37. γ3 and β4 polypetides of the invention can be expressed with, assembled with, or administered with other laminin subunits in any of the methods described herein. E.g., γ3 can be assembled with an α and a β subunit to form a laminin trimer. β4 can be assembled with an α and a β subunit to form a laminin trimer.

In any treatment or therapeutic application which administers γ3, a β2 subunit can also be administered.

A "heterologous promoter", as used herein is a promoter which is not naturally associated with a gene or a purified nucleic acid.

A "purified" or "substantially pure" or isolated "preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

An "isolated" or "pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA can also includes a recombinant DNA which is part of a hybrid gene encoding sequence.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology.

The terms "peptides", "proteins", and "polypeptides" are used interchangeably herein.

As used herein, the term "transgene" means a nucleic acid sequence (encoding, e.g., one or more subject laminin polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as mammary tissue. The term also covers so-called "leaky" promoters, which regulate expression of a selected DNA primarily in one tissue, but cause expression in other tissues as well.

"Unrelated to a γ3 or β4 amino acid or nucleic acid sequence" means having less than 30% sequence identity, less than 20% sequence identity, or, preferably, less than 10% homology with a naturally occurring γ3 or β4 sequence disclosed herein.

A polypeptide has γ3 biological activity if it has one or more of the properties of γ3 disclosed herein. A polypeptide has biological activity if it is an antagonist, agonist, or super-agonist of a polypeptide having one of the properties of γ3 disclosed herein.

A polypeptide has β4 biological activity if it has one or more of the properties of β4 disclosed herein. A polypeptide has biological activity if it is an antagonist, agonist, or super-agonist of a polypeptide having one of the properties of 4 disclosed herein.

"Misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

Subject, as used herein, can refer to a mammal, e.g., a human, or to an experimental or animal or disease model. The subject can also be a non-human animal, e.g., a horse, cow, goat, or other domestic animal.

As described herein, one aspect of the invention features a substantially pure (or recombinant) nucleic acid which includes a nucleotide sequence encoding a γ3 or 4 polypeptide and/or equivalents of such nucleic acids. The term nucleic acid as used herein can include fragments and equivalents. The term equivalent refers to nucleotide sequences encoding functionally equivalent polypeptides. Equivalent nucleotide sequences will include sequences that differ by one or more nucleotide substitutions, additions or deletions, Such as allelic variants, and include sequences that differ from the nucleotide sequences disclosed herein by degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); Oligonucleotide Synthesis (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, A Practical Guide To Molecular Cloning (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embtyo*, (Cold Spring Harbor Laboratory Press, Cold Spring Harbor, N.Y., 1986).

Other features and advantages of the invention will be apparent from the following detailed description, and from the claims.

DETAILED DESCRIPTION

The drawings are briefly described.

FIG. 1 depicts the cDNA sequence for human α2 subunit (SEQ ID NO:8).

FIG. 2 depicts the predicted amino acid sequence for human α2 subunit (SEQ ID NO:7).

FIG. 3 depicts the cDNA sequence for human β1 subunit (SEQ ID NO: 10).

FIG. 4 depicts the predicted amino acid sequence for human β1 subunit (SEQ ID NO:9).

FIG. 5 depicts an alignment of the amino acid sequence of human β4 of SEQ ID NO: 1 and β4 splice varient of SEQ ID NO:5 and laminin β1 (SEQ ID NO:9), β2 (SEQ ID NO:11), and β3 (SEQ ID NO:12) subunits. The consensus sequence, "beta", is also depicted (SEQ ID NO:13).

Figure 6:
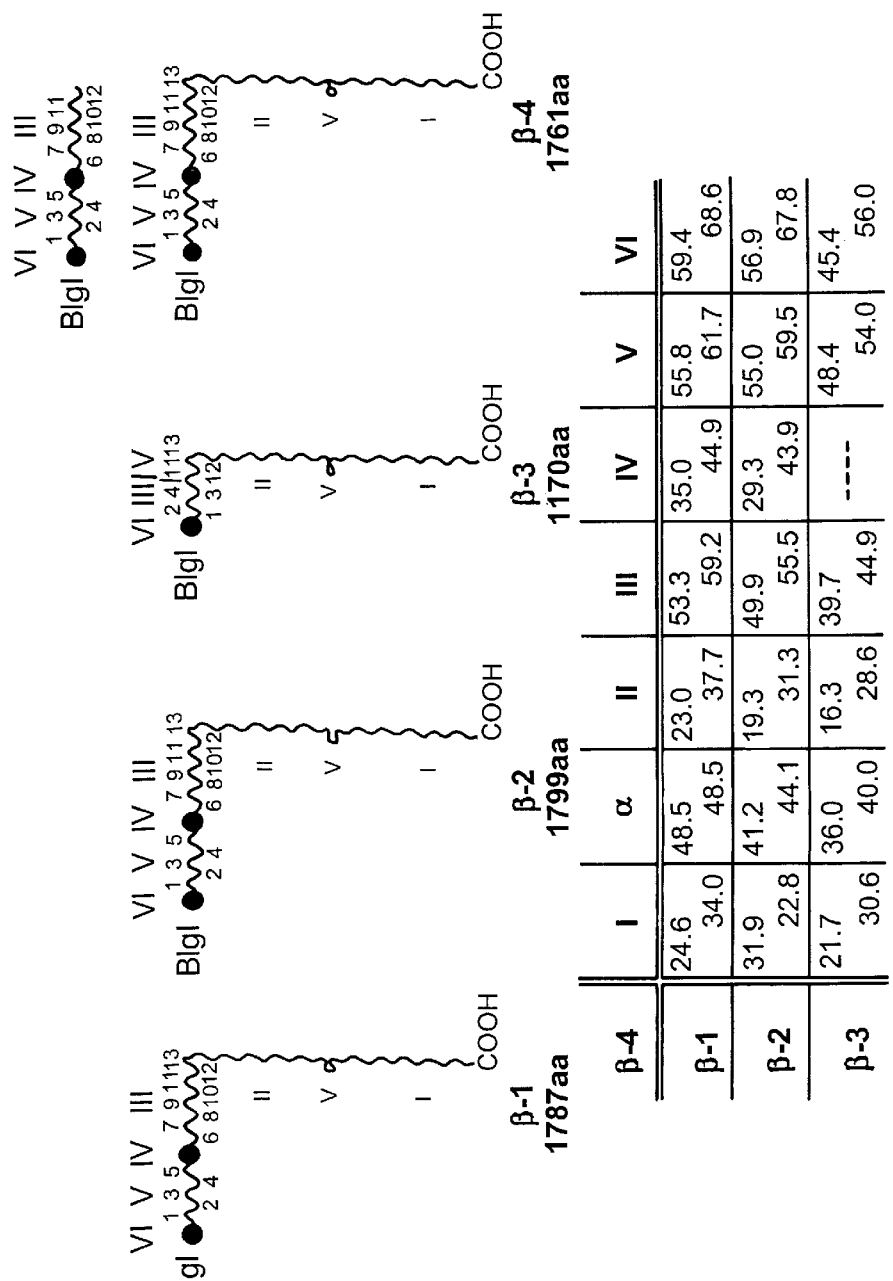

FIG. 6 provides a comparison of the similarities of laminin β4 domains with the domains of other known laminin β subunits.

ISOLATION OF LAMININ 12

Laminin 12 was isolated from human placental chorionic villi. Briefly, human chorionic placental villi were frozen in liquid nitrogen, ground in a Waring blender and washed in 1 M NaCl. The final tissue pellet (200 g, wet weight) was suspended in 1 L of extraction buffer (50 mM Tris-HCl 50 mM, pH=7.8; NaCl 0.5M, EDTA 10 mM, 625 mg/l of N-ethylmaleimide, 150 mg/l of phenylmethylsulphonyl fluoride. The suspension was incubated at 4° C. with stirring for 48 h. Unless otherwise noted, all subsequent steps were performed at 4° C. The soluble fraction was collected following centrifugation (30000×g, 60 min) and precipitated by 300 g/l of Ammonium Sulfate. The precipitated proteins were collected by centrifugation (30000×g, 60 min) and redissolved into chromatography buffer (2M Urea, 25 mM NaCl, 5 mM EDTA, and 50 mM Tris-HCl, pH=7.8). The sample was then dialyzed against the same buffer. Following dialysis, 0.5 volumes of buffer equilibrated DEAE-cellulose (DE-52, Whatman) was added and the mixture shaken overnight. Material not bound to DEAE-cellulose was collected by filtration on a Buchner funnel (Whatman filter 4) and precipitated by addition of 300 g/l of ammonium sulfate. The proteins were collected by centrifugation (30000×g, 60 min), redissolved in the Concanavalin-A buffer (0.5 M NaCl, 5 mM $CaCl_2$, 5 mM $MgCl_2$, and Tris-HCl 50 mM, pH=7.8) and dialyzed against the same buffer overnight. The fraction was applied to a 2.5×5 cm Concanavalin-A sepharose column (Pharmacia), and unbound material was removed by extensive washing. Bound proteins were first eluted with 10 mM α-D-Mannopyrannoside (Sigma, St. Louis, Mo.) and secondly with 1 M α-D-Glucopyrannoside (Sigma, St. Louis, Mo.). A third elution with 1 M α-D-Mannopyrannoside (Sigma, St. Louis, Mo.) allowed the recovery of the proteins of interest. Each fraction was independently concentrated to 10 ml on a Amicon™ concentrator (30 kDa membrane) and applied to a 2.5×100 cm Sephacryl S-500 column in a 0.5 M NaCl, 50 mM Tris-HCl, pH=7.8 buffer. The fractions of interest were pooled, dialyzed against Mono-Q buffer (0.1 M NaCl, 25 mM Tris-HCl, pH=7.8) and applied to the 1×5 cm Mono-Q column (Pharmacia). Elution was achieved with a 60 ml 0.1–0.5 M NaCl gradient.

The final fraction of interest resulting from the above protocol contains multiple laminins. The laminin 12 was resolved from this mixture by SDS-PAGE (3–5% polyacrylamide) under non-reducing conditions. Six band were resolved. Only the bands at approximately 560 kDa and at the top of the gel were shown to be reactive with polyclonal anti-laminin antiserum (Sigma, St. Louis, Mo.).

Isolation of α2, β1, γ3 Subunits From Laminin 12

Laminin 12 was excised, equilibrated and reduced in 10% 2-me SDS-PAGE sample buffer, and resolved by 5% SDS-PAGE. Three bands were resolved, which were approximately 205 kDa, 185 kDa, and 170 kDa. The band at 185 kDa reacted with monoclonal antibody 545, specific to the laminin β1 subunit. Each of the three bands were digested with trypsin and the peptides were resolved by HPLC. The selected resolves were subject to peptide sequencing.

Sequencing of the α2, β1 Subunits of Laminin 12

Protein sequencing was done according to Aebersold et al. (1987). The complex laminin 5-laminin 7 was run on a polyacrylamide gel in the presence of 2-mercaptoethanol and blotted onto a nitrocellulose membrane (Biorad). The 190 kDa band of β2 and the 165 kDa α3 band were separately excised and digested by protease trypsin. The digested product was separated by HPLC and one fragment was sequenced on an Applied Biosystems sequenator (Applied Biosystems, Foster City, Calif.). The 205 kDa chain contained a sequence identical to human laminin α2, and was thus identified as human laminin α2 subunit. The 185 kDa produced two peptides identical to human β1, and was thus identified as human laminin β1 subunit. The band at 170 kDa contained three sequences not contained in any known laminin chain. A N-terminal sequence of the 170 kDa chain was also determined. In addition, the N-terminal sequence was not identical to any known laminin sequence.

Identification of the γ3 Subunit

The cDNA sequences of human γ1 and γ2 were used to probe the National Center for Biomedical Information (NCBI) dBest™ data base by BLAST search and a clone was isolated that was homologous, but not identical to γ1 and γ2. This clone was extended by PCR at the 5' end using Marathon cDNA from human placenta from Clonetech (Palo Alto, Calif.). The resulting sequence was determined to be 100% identical to all three of the 170 kDa band peptide sequences.

Comparison of the nucleotide sequence of the isolated γ3 subunit to γ1, demonstrated about 80% sequence identity.

Structural Analysis of γ3 Encoding DNA

The human cDNA encoding γ3, which is approximately 4710 nucleotides in length, encodes a protein having an estimated molecular weight of approximately 146 kDa (including post-translational modifications) and which is approximately 1570 amino acid residues in length. The human γ3 protein contains a nidogen-binding domain, which can be found, for example, from about amino acids 750–755 of SEQ ID NO:3. The γ3 amino acid sequence and the nucleotide sequence encoding human laminin γ3 is shown in SEQ ID NO:3 and SEQ ID NO:4, respectively.

By Northern analysis the size of the γ3 mRNA is approximately 5 kb, which is consistent with other laminin y subunits. The γ3 mRNA transcript is expressed in human tissues including spleen, testis, brain, placenta, lung, and possibly liver. Chromosomal mapping using the γ3 cDNA sequence indicates that the human γ3 gene is located on chromosome 9q31–34. The location of γ3 on chromosome 9 was confirmed by FISH analysis using a 1.3 kb γ3 cDNA probe within the predicted domains I and II, which are the regions of the least sequence identity among y subunits. Four human genes associated with Walker-Walburg syndrome, Fukuyama muscular dystrophy, retinitis pigmentosa-deafness syndrome and Eye, Muscle, Brain disease have also been mapped to chromosome 9q31–34.

Production of a γ3 Specific Antibody and Tissue Localization of γ3

The 170 kDa (γ3) chain was excised from the reducing SDS-PAGE gel described above and injected into a rabbit for antibody production. The resulting serum (rabbit 16) was evaluated by Western analysis and shown to react with the 170 kDa γ3 chain, and showed minor crossreactivity with other laminin chains.

Using immunofluorescence, this antiserum shows localization of γ3 to the following tissue areas: 1) sites of insertions of nerves into the dermal-epidermal junction basement membrane of human skin; 2) the inner nuclear layers, outer nuclear layers, and outer limiting membranes of human, mouse and rat neural retina; 3) the Purkinje cells, and molecular layers, and (perhaps) the glial cells of the mouse and rat cerebellum; 4) the neuromuscular junctions of skeletal muscle; and, 5) the taste buds of the cow tongue.

The γ3 was also shown to colocalize with protein ubiquitin carboxy terminal hydrolase I using antibody pGp 9.5. The γ3 subunit also appears to colocalize with the α2 subunit in the same tissue sections.

Isolation and Sequencing of cDNA Encoding β4

The initial 350 bp fragment of human laminin β4 cDNA was amplified by touchdown RT-PCR from cultured human keratinocyte total RNA using nested primers made from the published chicken laminin β×503 bp cDNA sequence (as described in Ybot-Gonzalez et al. (1995)). Subsequent cDNA clones were isolated by nested PCR directly from a human placenta cDNA library packaged in lambda-gt11 (Clontech, Palo Alto, Calif.) or by nested PCR directly from human placenta Marathon-Ready cDNA (Clontech, Palo Alto, Calif.). The 5' end of the cDNA was cloned using the 5'-RACE technique from human placenta total RNA. The Expanded Long Template PCR System (Boehringer Mannheim Biochemicals, Indianapolis, Ind.) was used for all PCR reactions. The PCR products were ligated into the pCR2.1 vector (Invitrogen, San Diego, Calif.) and recombinant plasmids purified for sequencing using the QIAprep™ kit (Qiagen). The DNA sequence was determined using either the Sequenase version 2.0 DNA Sequencing Kit (Amersham) and $^{35}$S-dATP or the Thermo Sequenase Radiolabeled Terminator Cycle Sequencing kit (Amersham) and $^{33}$P-ddNTPs. At least two independent cDNA subclones were sequenced to rule out Taq polymerase-generated nucleotide substitutions. In some cases, PCR product bands were sequenced directly by cycle sequencing after excision from a TAE-EtBr agarose gel and purification using QIAquick Gel Extraction kit (Qiagen).

Structural Analysis of DNA Encoding β4

The human cDNA encoding a long form β4, which is approximately 5.87 kb, encodes a protein having an estimated molecular weight of approximately 200 kDa and which is approximately 1761 amino acid residues in length. The human β4 protein retains the highest amino acid sequence identity with domains VI and V, which can be found, for example, from about amino acids 221–262 and about 263–535 of SEQ ID NO:1. In addition, a short form, splice variant of β4, which is approximately 3.84 kb and an estimated molecular weight of 120 kDa, was also isolated. The splice variant has 132 nucleotide sequence identical to the long form of β4, with the sequence diverging at nucleotide 3375 and spliced into a unique 3' untranslated region. The short form cDNA encodes a truncated β4 subunit which contains only the short arm of the β4 subunit and is missing the domains necessary for heterodimerization. The β4 amino acid sequence and the nucleotide sequence encoding human laminin β4 is shown in SEQ ID NO:1 and SEQ ID NO:2, respectively.

Northern analysis was performed using total RNA prepared from JAR cell, cultured human keratinocytes and human placenta using either Trizol (Gibco BRL, Bethesda, Md.) or RNeaSy™ (Qiagen) which was denatured, separated on a formaldehyde agarose gel and blotted onto nitrocellulose according to standard protocols (Sambrook, et al., 1989). In addition, a human multiple tissue northern blot (Clontech, Palo Alto, Calif.) and Human Northern Territory normal tissue blots and custom fetal skin northern blot (Invitrogen, San Diego, Calif.) were used. Hybridization and washing were performed using NorthernMAX™ buffer system (Ambion) by manufacturer's recommended protocols. 32P-dCTP-labelled probes were generated from gel-purified restriction fragments using Rediprime™ random primer labeling kit (Amersham). 32P-UTP-labelled antisense RNA probes were generated using the RNA transcription kit (Stratagene, La Jolla, Calif.) from cDNAs subcloned into Bluescript II KS+ (Stratagene, La Jolla, Calif.).

Northern blotting showed that human laminin β4 is expressed in JAR cells, derived from undeveloped chronic villi and in placenta. By RT-PCR, it is also expressed in cultured keratinocytes. Using a northern blot of human fetal skin developmental progression, β4 subunit (long form) demonstrates strong expression at week twelve of fetal development and persists until birth, but expression is barely detectable in adult skin. The β4 splice variant, however, is expressed in various tissues including adult heart, brain, lung, liver, skeletal muscle, kidney, spleen, stomach, esophagus, intestine, colon, uterus, bladder, adipose tissue and pancreas. Chromosomal mapping with a β4 cDNA probe indicates that the human β4 subunit is located at locus 7q22–q31.2. The gene encoding β1 is located near, but not on, this position of chromosome 7. Statistical analysis of the mapping data using markers for β1 and β4 suggest that the gene encoding β1 is linked to both ends of the gene encoding β4. In addition, neonatal cutis laxa with manifold phenotype has been mapped near, but not in the same position, as the gene encoding β4.

In situ hybridization to wounded human skin grafted into nude mice suggests that laminin β x is expressed in the dermis underneath the migrating epidermal tongues during wound closure.

A GenBank™ search using the human nucleotide sequence encoding β4 as shown in SEQ ID NO:3 revealed an EST, which corresponds to nucleotides 4686–5870 of the human nucleotide sequence encoding β4 depicted in SEQ ID NO:3. Alignment of cDNA encoding β4 with the genes encoding human laminin β1 and laminin β2 shows 61% and 59% sequence identity, respectively, as shown in FIG. 5.

Production of a β4 Specific Antibody and Tissue Localization of β4

Antibodies were raised in rabbits against a 26 kDa bacterial fusion protein which corresponds to the 175 amino acid residues of domain VI (e.g., from about amino acid residues 221–262) of SEQ ID NO:1. Briefly the fusion protein was made by PCR amplification of nucleotides 302–785 of the cDNA encoding β4 using adapter primers and cloned in-frame into the NdeI and SacII sites of pET-15b (Novagen). The fusion protein construct was confirmed by restriction mapping and DNA sequencing. Expression of the fusion protein was induced and separated from *E. coli* proteins using reducing SDS-PAGE. Bands corresponding to the fusion protein were excised from the gel, equilibrated and homogenized using Freud's adjuvant. The same fusion protein was also western blotted on nitrocellulose, dissolved in DMSO and used to immunize mice for monoclonal antibody production.

The polyclonal antisera raised in mice against the fusion protein reacted well with β4, as well as, β3 and β32 polypeptides.

Structural Analysis of the β4 Subunit and the β4 Splice Variant

The β4 subunit contains six domains, and a interruption and a signal peptide. The signal peptide and domain VI can be found, for example, at about amino acid residues 1–262 of SEQ ID NO:1. Domain V can be found, for example, at about amino acid residues 263–535 of SEQ ID NO:1. Domains IV and III can be found, for example, at about amino acid residues 536–767 and 768–1178 of SEQ ID NO:1, respectively. Domain I can be found, for example, at about amino acid residues 1409–1761 of SEQ ID NO:1.

The β4 subunit (long form) is most similar in size and domain structure to laminin PI with an amino acid sequence identity of 42.5%. β4 retains the highest levels of amino acid identity with the other laminin β subunits in domains VI and V, and the lowest levels in domains I and II, as shown in FIG. 6. Using the MultiCoil™ program, it was determined that only domains I and II of β4 have a high probability of forming coiled coil structures. Domains I and II of β4 look most similar to human β3. Both β4 and β3 are epithelial and the coiled coil structures in domains I and II dictate the α and γ subunits with which the β subunits are associated. Thus, it is likely that β4 associates with α3 and γ2, as does the laminin β3 subunit.

The cDNA encoding the splice variant of β4 contains only the short arm of the β4 subunit, and is missing the EGF repeat of domain III, as shown in FIG. 5. Thus, the β4 polypeptide encoded by the β4 cDNA splice variant is missing the coiled coil structures in domains I and II, rendering the short subunit unable to associate into a laminin heterotirimer. PCR amplification of human genomic DNA suggest that the exon which encodes the alternative short form 3' untranslated region is located downstream from the carboxyl-most common exon, exon 23, and is splices out of the β4 subunit, long form, by exon skipping.

Analogs of γ3 and β4

Analogs can differ from naturally occurring γ3 or β4 in amino acid sequence or in ways that do not involve sequence, or both. Non-sequence modifications include in vivo or in vitro chemical derivatization of γ3 or β4. Non-sequence modifications include changes in acetylation, methylation, phosphorylation, carboxylation, or glycosylation.

Preferred analogs include γ3 or β4 (or biologically active fragments thereof) whose sequences differ from the wild-type sequence by one or more conservative amino acid substitutions or by one or more non-conservative amino acid substitutions, deletions, or insertions which do not abolish the γ3 or β4 biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Gene Therapy

The gene constructs of the invention can also be used as a part of a gene therapy protocol to deliver nucleic acids encoding either an agonistic or antagonistic form of a γ3 or β4 polypeptide. The invention features expression vectors for in vivo transfection and expression of a γ3 or β4 polypeptide in particular cell types so as to reconstitute the function of, or alternatively, antagonize the function of γ3 or β4 polypeptide in a cell in which that polypeptide is misexpressed. Expression constructs of γ3 or β4 polypeptides, may be administered in any biologically effective carrier, e.g. any formulation or composition capable of effectively delivering the γ3 or β4 gene to cells in vivo. Approaches include insertion of the subject gene in viral vectors including recombinant retroviruses, adenovirus, adeno-associated virus, and herpes simplex virus-l, or recombinant bacterial or eukaryotic plasmids. Viral vectors transfect cells directly; plasmid DNA can be delivered with the help of; for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a γ3 or β4 polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) Science 230:1395–1398; Danos and Mulligan (1988) Proc. Natl. Acad Sci. USA 85:6460–6464; Wilson et al. (1988) Proc. Natl. Acad Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad Sci. USA 89:7640–7644; Kay et al. (1992) Human Gene Therapy 3:641–647; Dai et al. (1992) Proc. Natl. Acad Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a γ3 or β4 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject γ3 or β4 gene by the targeted cell. Exemplary gene delivery systems of this type include liposomal derived systems, poly-lysine conjugates, and artificial viral envelopes.

In a representative embodiment, a gene encoding a γ3 or β4 polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic γ3 or β4 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Transpenic Animals

The invention includes transgenic animals which include cells (of that animal) which contain a γ3 or β4 transgene and which preferably (though optionally) express (or misexpress) an endogenous or exogenous γ3 or β4 gene in one or more cells in the animal. The γ3 or β4 transgene can encode the wild-type form of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns, e.g., to restrict production to the milk or other secreted product of the animal.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). Tllis technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1 983) *Nucleic Acid Res*. 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-mediated Mutagenesis

Oligonucleotide-mediated mutagenesis is a useful method for preparing substitution, deletion, and insertion variants of DNA, see, e.g., Adelman et al., (DNA 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-through-put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to other laminin subunits, assembly into a trimeric laminin molecules, binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays such as the system described above (as with the other screening methods described herein), can be used to identify fragments or analogs. These may include agonists, superagonists, and aentagonists. (The subject protein and a protein it interacts with are used as the bait protein and fish proteins.).

Display Libraries

In one approach to screening assays, the candidate peptides are displayed on the surface of a cell or viral particle, and the ability of particular cells or viral particles to bind an appropriate receptor protein via the displayed product is detected in a "panning assay". Foor example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamnentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech*. 6, 1080–1083). Surface proteins of other bacterial species have also served as peptide fusion partners. Examples include the Staphylococcus protein A and the outer membrane protease IgA of *Neisseria* (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysornes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject γ3 or β4 polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J. Med Chem* 29:295; and Ewenson et al. in *Pepltides: Structure and Function* (Proceedings of the 9th American Peptide Symposium) Pierce Chemical Co. Rockland, Ill., 1985), β-turn dipeptide cores (Nagai et al. (1985) *Tetrahedron Lett*26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Antibodies

The invention also includes antibodies specifically reactive with a subject γ3 or β4 polypeptides. Anti-protein/anti-peptide antisera or monoclonal antibodies can be made by standard protocols (See, for example, *Antibodies: A Laboratory Manual* ed. by Harlow and Lane (Cold Spring Harbor Press: 1988)).

Antibodies which specifically bind γ3 or β4 epitopes can also be used in immunohistochemical staining of tissue samples in order to evaluate the abundance and pattern of expression of γ3 or β4. Anti γ3 or β4 antibodies can be used diagnostically in immuno-precipitation and immuno-blotting to detect and evaluate γ3 or β4 levels in tissue or bodily fluid as part of a clinical testing procedure.

Another application of antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

Other Embodiments

Included in the invention are: allelic variations; natural mutants; induced mutants; proteins encoded by DNA that hybridizes under high or low stringency conditions to a nucleic acid which encodes a polypeptide of SEQ ID NO:1 or SEQ ID NO:3 (for definitions of high and low stringency see Current Protocols in Molecular Biology, John Wiley & Sons, New York, 1989, 6.3.1–6.3.6, hereby incorporated by reference); and, polypeptides specifically bound by antisera to γ3 or β4. High stringency conditions for aqueous hybridization can be conducted at 65° C., using the high stringency wash buffer, 1 mM Na$_2$EDTA; 40mM NaHPO$_4$, pH 7.2; and 1% SDS, and include multiple quick washes (5–8) and immerse in a final wash for 20 minutes. (Current Protocols in Molecular Biology, John Wiley & Sons, New York, 1989, 6.3.1–6.3.6).

Nucleic acids and polypeptides of the invention includes those that differ from the sequences discolosed herein by virtue of sequencing errors in the disclosed sequences.

The invention also includes fragments, preferably biologically active fragments, or analogs of γ3 or β4. A biologically active fragment or analog is one having any in vivo or in vitro activity which is characteristic of the γ3 or β4 shown in SEQ ID NO:3 and SEQ ID NO:1, respectively, or of other naturally occurring γ3 or β4, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Particularly preferred fragments are fragments, e.g., active fragments, which are generated by proteolytic cleavage or alternative splicing events.

Other embodiments are within the following claims.

What is claimed is:

1. An isolated laminin 12 comprising an α-2 subunit that comprises the sequence of SEQ ID NO:7; a β1 subunit that comprises the sequence of SEQ ID NO:9; and a γ3 subunit that comprises the sequence of SEQ ID NO:3.

2. An isolated laminin 12 comprising an α2 subunit, a β1 subunit and a γ3 subunit, wherein:
   (a) the α2 subunit consists of the sequence of SEQ ID NO:7,
   (b) the β1 subunit consists of the sequence of SEQ ID NO:9, and
   (c) the γ3 subunit consists of the sequence of SEQ ID NO:3.

3. An isolated laminin 12 comprising an α2 subunit, a β1 subunit and a γ3 subunit; wherein:
   (a) the α2 subunit is encoded by a nucleic acid molecule which hybridizes under high stringency conditions to the nucleic acid sequence of SEQ ID NO:8, and is about 205 kDa in mass as determined by gel electrophoresis under reducing conditions;
   (b) the β1 subunit is encoded by a nucleic acid molecule which hybridizes under high stringency conditions to the nucleic acid sequence of SEQ ID NO:10, and is about 185 kDa in mass as determined by gel electrophoresis under reducing conditions; and
   (c) the γ3 subunit is encoded by a nucleic acid molecule which hybridizes under high stringency conditions to the nucleic acid sequence of SEQ ID NO:4, and is about 170 kDa in mass as determined by gel electrophoresis under reducing conditions;
   the high stringency conditions comprising a temperature of 65° C. and a high stringency wash buffer of 1 mM Na2EDTA, 40 mM NaHPO4, pH 7.2, and 1% SDS,
   wherein the laminin 12 promotes adhesion of a first tissue element to a second tissue element.

4. The isolated laminin-12 of claim 1, wherein the laminin-12 is isolated from a tissue.

5. The isolated laminin-12 of claim 1, wherein the laminin-12 is recombinantly produced.

6. The isolated laminin 12 of claim 1, wherein the α2, β1, or γ3 subunit is a fusion protein comprising a heterologous polypeptide sequence wherein said heterologous polypeptide sequence is glutathione-S-transferase.

7. The isolated laminin 12 of claim 3, wherein the laminin 12 is isolated from a tissue.

8. The isolated laminin 12 of claim 3, wherein the laminin 12 is recombinantly produced.

9. The isolated laminin 12 of claim 3, wherein the α2, β1, or γ3 subunit is a fusion protein comprising a heterologous polypeptide sequence wherein said heterologous polypeptide sequence is glutathione-S-transferase.

* * * * *